United States Patent [19]
Boeshore et al.

[11] Patent Number: 6,160,201
[45] Date of Patent: Dec. 12, 2000

[54] LETTUCE INFECTIOUS YELLOWS VIRUS GENES

[75] Inventors: Maury L. Boeshore, Waukegon, Ill.; Kim J. Carney, Richland, Mich.; Vicki Klaassen; Bryce W. Falk, both of Davis, Calif.

[73] Assignees: Seminis Vegetable Seeds, Inc., Saticoy; The Regents of the University of California, Oakland, both of Calif.

[21] Appl. No.: 08/591,468

[22] PCT Filed: Jun. 13, 1994

[86] PCT No.: PCT/US94/06430

§ 371 Date: Aug. 2, 1996

§ 102(e) Date: Aug. 2, 1996

[87] PCT Pub. No.: WO95/02056

PCT Pub. Date: Jan. 19, 1995

Related U.S. Application Data

[63] Continuation of application No. 08/090,532, Jul. 9, 1993, abandoned, application No. 08/138,138, Oct. 15, 1993, abandoned, and application No. 08/146,780, Nov. 1, 1993, abandoned.

[51] Int. Cl.$^7$ .............................. A01H 5/00; A01H 5/10; C12N 5/04; C12N 15/82

[52] U.S. Cl. ..................... 800/250; 800/205; 435/69.1; 435/172.3; 435/320.1; 435/419; 435/252.3; 536/23.72

[58] Field of Search ................................... 800/205, 250; 435/69.1, 172.3, 320.1, 419, 252.3; 536/23.72

[56] References Cited

U.S. PATENT DOCUMENTS

| | | | |
|---|---|---|---|
| 4,774,182 | 9/1988 | Szybalski | 435/68 |
| 4,940,838 | 7/1990 | Schilperoort et al. | 800/205 |
| 4,970,168 | 11/1990 | Tumer | 435/317.1 |

FOREIGN PATENT DOCUMENTS

| | | |
|---|---|---|
| 71951/91 | 3/1992 | Australia . |
| 0 426 195 | 5/1991 | European Pat. Off. . |
| 0 536 106 | 4/1993 | European Pat. Off. . |
| 0 223 452 | 4/1996 | European Pat. Off. . |
| WO 89/05858 | 6/1989 | WIPO . |
| WO 89/05859 | 6/1989 | WIPO . |
| WO 90/02184 | 3/1990 | WIPO . |
| WO 90/02185 | 3/1990 | WIPO . |
| WO 90/02189 | 3/1990 | WIPO . |
| WO 91/13542 | 9/1991 | WIPO . |
| WO 92/03539 | 3/1992 | WIPO . |

OTHER PUBLICATIONS

T. Michael A. Wilson, *Proc. Natl. Acad. Sci. USA*, vol. 90, pp. 3134–3141 (Apr. 1993).

Woudt, L.P., et al. Sequence Analysis of the RNA Genome of Cucumber Chlorotic Spot Virus (CCSV), A Whitefly Transmitted Closterovirus, 9th International Congress of Virology, Glasgow, Scotland, Aug. 8–13, 1993. (Abstract No. P60–26).

J.K. Brown and B.T. Poulos, *Journal Rio Grande Valley Horticultural Society*, vol. 42, pp. 13–18 (1989).

Klaassen, V.A., et al. "Molecular Characterization of Lettuce Infectious Yellows Virus," Annual Meeting of the American Phytopathological Society, Portland, Oregon, USA, Aug. 8–12, 1992 (Abstract No. A459).

Agranovsky et al., "Putative 65 kDa Protein of Beet Yellows Closterovirus Is a Homologue of HSP70 Heat Shock Proteins," *J. Mol. Biol.*, vol. 217, 1991, pp. 603–610.

Agranovsky et al., "Nucleotide sequence of the 3'–terminal half of beet yellows closterovirus RNA genome: unique arrangement of eight virus genes", *Journal of General Virology*, vol. 72, 1991, pp. 15–23.

Amasino, "Acceleration of Nucleic Acid Hybridization Rate by Polyethylene Glycol", *Analytical Biochemistry*, vol. 152, 1986, pp. 304–307.

Anderson et al., "A defective replicase gene induces resistance to cucumber mosaic virus in transgenic tobacco plants", *Proc. Natl. Acad. Sci. USA*, vol. 89, 1992, pp. 8759–8763.

Baltimore, "Purification and Properties of Poliovirus Double–stranded Ribonucleic Acid", *J. Mol. Biol.*, vol. 18, 1966, pp. 421–428.

Beachy et al., "Coat Protein–Mediated Resistance Against Virus Infection", *Annu. Rev. Phytopathol.*, vol. 28, 1990, pp. 451–474.

Bejarano et al., "Prospects for engineering virus resistance in plants with antisense RNA", *Tibtech*, vol. 10, 1992, pp. 383–388.

Birnboim et al., "A rapid alkaline extraction procedure for screening recombinant plasmid DNA", *Nucleic Acids Research*, vol. 7, No. 6, 1979, pp. 1513–1523.

Boyko et al., "Coat protein gene duplication in a filamentous RNA virus of plants", *Proc. Natl. Acad. Sci. USA*, vol. 89, 1992, pp. 9156–9160.

Braun et al., "Expression of Amino–Terminal Portions or Full–Length Viral Replicase Genes in Transgenic Plants Confers Resistance to Potato Virus X Infection", *The Plant Cell*, vol. 4, 1992, pp. 735–744.

Brunstedt et al., "Nucleotide Sequence of Beet Yellows Virus and Expression of the Coat Protein Gene in *E. Coli* and in Plants", *Program & Abstracts*, International Soc. for Plant Molecular Biology, Third International Congress, Tucson, AZ, Oct. 6–11, 1991.

(List continued on next page.)

*Primary Examiner*—Elizabeth F. McElwain
*Attorney, Agent, or Firm*—Rockey, Milnamow & Katz, Ltd.

[57] ABSTRACT

The present invention provides an isolated nucleic acid which contains a nucleotide sequence which encodes at least one of five LIYV proteins: the coat protein, the heat shock protein-70, RNA polymerase, the protein encoded by the gene positioned at ORF 3 of LIYV RNA1, and the protein encoded by the gene positioned at ORF 6 of LIYV RNA2 where at least a portion of the nucleotide sequence for at least one of these proteins, either in the sense or the antisense orientation, is operably linked to genetic regulatory sequences necessary for gene expression to form plant transformation vectors. These vectors are then used to prepare transgenic seeds and plants.

46 Claims, 36 Drawing Sheets

OTHER PUBLICATIONS

Bruenn, "Relationships among the positive strand and double-strand RNA viruses as viewed through their RNA-dependent RNA polymerases", *Nucleic Acids Research*, vol. 19, No. 2, 1991, pp. 217–226.

Burnette, "Western Blotting: Electrophoretic Transfer of Proteins from Sodium Dodecyl Sulfate–Polyacrylamide Gels to Unmodified Nitrocellulose and Radiographic Detection with Antibody and Radioiodinated Protein A", *Analytical Biochemistry*, vol. 112, 1981, pp. 195–203.

Carr et al., "Resistance to Tobacco Mosaic Virus Induced by the 54–kDa Gene Sequence Requires Expression of the 54–kDa Protein" *Molecular Plant–Microbe Interactions*, vol. 5, No. 5, 1992, pp. 397–404.

Carr et al., "Resistance in Transgenic Tobacco Plants Expressing a Nonstructural Gene Sequence of Tobacco Mosaic Virus is a Consequence of Markedly Reduced Virus Replication", *Molecular Plant–Microbe Interactions*, vol. 4, No. 6, 1991, pp. 579–585.

Chee et al., "Transfer and Expression of Cucumber Mosaic Virus Coat Protein Gene in the Genome of *Cucumis sativus*", *J. Amer. Soc. Hort. Sci.*, vol. 116(6), 1991, pp. 1098–1102.

Cuozzo et al., "Viral Protection in Transgenic Tobacco Plants Expressing the Cucumber Mosaic Virus Coat Protein or Its Antisense RNA", *Bio/Technology*, vol. 6, 1988, pp. 549–557.

Dawson et al., "Tobacco Mosaic Virus Protein Synthesis is Correlated with Double–Stranded RNA Synthesis and Not Single–Stranded RNA Synthesis", *Virology*, vol. 125, 1983, pp. 314–323.

Day et al., "Expression of an antisense viral gene in transgenic tobacco confers resistance to the DNA virus tomato golden mosaic virus", *Proc. Natl. Acad. Sci. USA*, vol. 88, 1991, pp. 6721–6725.

Donson et al., "Tobacco plants transgenic for non–structural genes of tobacco mosaic virus (TMV) are resistant to infection by TMV and other tobamoviruses", *Phytopathology*, vol. 82, 1992, p. 1071 (abstr).

Duffus et al., "Lettuce Infectious Yellows—A New Whitefly Transmitted Virus of the Desert Southwest," *Phytopathology*, vol. 72, No. 7, 1982, p. 963 (abstr).

Duffus et al., "Lettuce Infectious Yellows Virus—A New Type of Whitefly–Transmitted Virus", *Phytopathology*, vol. 76, No. 1, 1986, pp. 97–100.

Enomoto et al., "Induced expression of a chimeric gene construct in transgenic lettuce plants using tobacco pathogenesis–related protein gene promoter region", *Plant Cell Reports*, vol. 9, 1990, pp. 6–9.

Golemboski et al., "Plants transformed with a tobacco mosaic virus nonstructural gene sequence are resistant to the virus", *Proc. Natl. Acad. Sci. USA*, vol. 87, 1990, pp. 6311–6315.

Gonsalves et al., "Comparison of Coat Protein–Mediated and Genetically–Derived Resistance in Cucumbers To Infection by Cucumber Mosaic Virus Under Field Conditions with Natural Challenge Inoculations by Vectors", *Bio/Technology*, vol. 10, 1992, pp. 1562–1570.

Gumpf et al., "Purification of Citrus Tristeza Virus (CTV) on Sucrose–Cesium Sulphate Cushion Gradients and Estimation of its RNA Size", *Phytopathology*, p. 878.

Habili et al., "Evolutionary relationship between luteoviruses and other RNA plant viruses based on sequence motifs in their putative RNA polymerases and nucleic acid helicases", *Nucleic Acids Research*, vol. 17, No. 23, 1989, pp. 9543–9555.

Halliwell et al., "Lettuce Infectious Yellows Infecting Watermelon, Cantaloupe, Honey Dew Melon, Squash, and Cushaw in Texas", *Plant Disease*, Jun. 1992, p. 643.

Hemenway et al., "Analysis of the mechanism of Protection in transgenic plants expressing the potato virus X coat protein or its antisense RNA", *Plant Molecular Biology*, pp. 1273–1280.

Kamer et al., "Primary structural comparison of RNA–dependent polymerases from plant, animal and bacterial viruses", *Nucleic Acids Research*, vol. 12, No. 18, 1984, pp. 7269–7283.

Klaassen et al., "Molecular Characterization of Lettuce Infectious Yellows Virus", *Phytopathology*, vol. 82, No. 10, 1992, p. 1111.

Klaassen et al., "Molecular Characterization of the Lettuce Infectious Yellows Genome", *American Society of Virology meetings*, A43, 1993, 19–8 (abstract).

Klaassen et al., "Partial characterization of the lettuce infectious yellows virus genomic RNAs, identification of the coat protein gene and comparison of its amino acid sequence with those of other filamentous RNA plant viruses", *Journal of General Virology*, vol. 75, 1994, pp. 1525–1533.

Koonin, "The phylogeny of RNA–dependent RNA polymerases of positive–strand RNA viruses", *Journal of General Virology*, vol. 72, 1991, pp. 2197–2206.

Ling et al., "Protection Against Detrimental Effects of Potyvirus Infection in Transgenic Tobacco Plants Expressing the Papaya Ringspot Virus Coat Protein Gene", *Bio/Technology*, vol. 9, 1991, pp. 752–758.

Lockhart et al., "Partial Purification and Serology of Sugarcane Mild Mosaic Virus, A Mealybug–Transmitted Closterolike Virus", *Phytopathology*, vol. 82, No. 6, 1992, pp. 691–695.

Longstaff et al., "Extreme resistance to potato virus X infection in plants expressing a modified component of the putative viral replicase", *The Sainsbury Laboratory*, pp. 379–386.

MacFarlane et al., "Plants transformed with a region of the 201–kilodalton replicase gene from pea early browning virus RNA1 are resistant to virus infection", *Proc. Natl. Acad. Sci. USA*, vol. 89, 1992, pp. 5829–5833.

Maiti et al., "Plants that express a potyvirus proteinase gene are resistant to virus infection", *Proc. Natl. Acad. Sci. USA*, vol. 90, 1993, pp. 6110–6114.

McCreight et al., "Lettuce Infectious Yellows Tolerance in Lettuce", *J. Amer. Soc. Hort. Sci.*, vol. 111(5), 1986, pp. 788–792.

Murashige et al., "A revised Medium for Rapid Growth and Bio Assays with Tobacco Tissue Cultures", *Physiologia Plantarum*, vol. 15, 1962, pp. 473–497.

Pappu et al., "Citrus Tristeza Virus Potentially Encodes HSP70 and HSP90–Like Proteins", *American Society for Virology Meeting*, Davis, California, Jul. 11–14, 1993, A43, 19–7 (abstract).

Abel et al., "Delay of Disease Development in Transgenic Plants that Express the Tobacco Mosaic Virus Coat Protein Gene", *Science*, vol. 232, 1986, pp. 738–743.

Quemada et al., "Expression of Coat Protein Gene from Cucumber Mosaic Virus Strain C in Tobacco: Protection Against Infections by CMV Strains Transmitted Mechanically or by Aphids", *Phytopathology*, vol. 81, No. 7, 1991, pp. 7954–802.

Sekiya et al., "Molecular cloning and nucleotide sequencing of the coat protein gene of citrus tristeza virus", *Journal of General Virology*, vol. 72, 1991, pp. 1013–1020.

Slightom, "Custom polymerase–chain–reaction engineering of a plant expression vector", *Gene* 03961, 1991, pp. 251–255.

Szybalski, "Protection of plants against viral disease by cloned viral genes and anti–genes", *Gene*, vol. 107, 1991, pp. 177–179.

Tumer et al., "Expression of alfalfa mosaic virus coat protein gene confers cross–protection in transgenic tobacco and tomato plants", *Plant Molecular Biology*, pp. 1181–1188.

Michael et al., "Strategies to protect crop plants against viruses: Pathogen–derived resistance blossoms", *Proc. Natl. Acad. Sci. USA*, vol. 90, 1993, pp. 3134–3141.

FIGURE 1A

LIYV COAT PROTEIN ENGINEERING

```
                    Eco RI   Nco I                              SEQ ID NO:3
RMM 306     TCAAAATTTATAGAATTCGCCATGGATACAG
SEQ ID NO:5 1 TCAAAATTTATATTTAAGATATACAGATGGAGATAATGATGTGTT            50
SEQ ID NO:2                     M  D  T  D  G  D  N  D  V  F

51        TGGATCGGGAAACGATACCAGGAATAATGATGATAAGAAGAAAGAGGAAA       100
             G  S  G  N  D  T  R  N  N  D  D  K  K  K  E  E  M

101        TGAAACAAAACATTCTGACAATTCTCAAATCATATCAACCAGGATCAT         150
             K  Q  N  I  S  D  N  S  Q  I  I  S  T  R  D  H

151        GAAGCTGACATCATTGGAAGTATATCGAAAGAGGATTTGTCAAAATCGT        200
             E  A  D  I  I  G  S  I  S  K  E  D  L  S  K  I  V

201        TGTACGCGTCGACAGGCACGATGCTCTGAGTGCTAATGATGTTCAAAGTT       250
             V  R  V  D  R  H  D  A  L  S  A  N  D  V  Q  S  F

251        TTAGAGAAGCTATGATAAACTTCATGCGAGACAAAGACCCCAACAGAAAT       300
             R  E  A  M  I  N  F  M  R  D  K  D  P  N  R  N

301        CAACCTAGTGACAAATTGATTATTGCTATGGAAGTTGGAGTTTATCAAAT       350
             Q  P  S  D  K  L  I  I  A  M  E  V  G  V  Y  Q  M

351        GGTCATAAATTTGGGCACTTCGGCTAAATTGGGTAATGCTAACAATTAG        400
             V  I  N  L  G  T  S  A  K  L  G  N  A  N  N  L  E

401        AATTTACGATAGCTTACGACCAGGAAACTAGGACATATAAGGTCGCAGAT       450
             F  T  I  A  Y  D  Q  E  T  R  T  Y  K  V  A  D

451        TTTGTGAATTATATGCAGTCTAGAATGAGGAACAGTCCAAATGTTGTTAG       500
             F  V  N  Y  M  Q  S  R  M  R  N  S  P  N  V  V  R
```

FIGURE 1B

```
501  GCAATATGCAAGAGCAATGGAAAAGACAATTAACAACATAAGGAGTGCTG    550
      Q  Y  A  R  A  M  E  K  T  I  N  N  I  R  S  A  G

551  GAATCATAAACAGCAATGGAGTTTTGGCAGCGAAACATGGTGTGTTGGCA    600
      I  I  N  S  N  G  V  L  A  A  K  H  G  V  L  A

601  TCTTACAGAAACTCTTACAGCGACTTTGCTGTTGGTTTTGGTAACGACAC    650
      S  Y  R  N  S  Y  S  D  F  A  V  G  F  G  N  D  T

651  CACTGATGCTCAACTCACTTCGCTAATGTTAGCTAGAAAACAAGCATTAT    700
      T  D  A  Q  L  T  S  L  M  L  A  R  K  Q  A  L

701  GCAAAGGTGAAGGTGGTTCAGTCGAGCATTACAATACTATGCAGTTAGCT    750
      C  K  G  E  G  G  S  V  E  H  Y  N  T  M  Q  L  A

751  AACCTTAAACATCCATGTTAGAGGCGGAATGTGATGAAGTAGAACTAACC    800
                                                      GATTGG
      N  L  K  H  P  C  *

801  TCCAGAGATGTCGGAGTTATTGATGTTC  829        SEQ ID NO:4
     AGGTCGGTACCCCTAGGTAAACTACAAG  RMM 307
     Nco I  Bam HI
```

```
SEQ ID NO:1
TCAAAATTTA TATTTTAAGA TATGGATACA GATGGAGATA ATGATGTGTT TGGATCGGGA    60
AACGATACCA GGAATAATGA TGATAAGAAG AAAGAGGAAA TGAAACAAAA CATTTCTGAC   120
AATTCTCAAA TCATATCAAC CAGGGATCAT GAAGCTGACA TCATTGGAAG TATATCGAAA   180
GAGGATTTGT CCAAAATCGT TGTACGCGTC GACAGGCACG ATGCTCTGAG TGCTAATGAT   240
GTTCAAAGTT TTAGAGAAGC TATGATAAAC TTCATGCGAG ACAAAGACCC CAACAGAAAT   300
CAACCTAGTG ACAAATTGAT TATTGCTATG GAAGTTGGAG TTTATCAAAT GGTCATAAAT   360
TTGGGCACTT CGGCTAAATT GGGTAATGCT AACAATTTAG AATTTACGAT AGCTTACGAC   420
CAGGAAACTA GGACATATAA GGTCGCAGAT TTTGTGAATT ATATGCAGTC TAGAATGAGG   480
AACAGTCCAA ATGTTGTTAG GCAATATGCA AGAGCAATGG AAAAGACAAT TAACAACATA   540
AGGAGTGCTG GAATCATAAA CAGCAATGGA GTTTTGGCAG CGAAACATGG TGTGTTGGCA   600
TCTTACAGAA ACTCTTACAG CGACTTTGCT GTTGGTTTTG GTAACGACAC CACTGATGCT   660
CAACTCACTT CGCTAATGTT AGCTAGAAAA CAAGCATTAT GCAAAGGTGA AGGTGGTTCA   720
CAACTCACTT ACAATACTAT GCAGTTAGCT AACCTTAAAC ATCCATGTTA GAGGCGGAAT   780
GTGATGAAGT AGAACTAACC TCCAGAGATG TCGGAGTTAT TTGATGTTC              829
```

FIGURE 4

SEQ ID NO:2

Met Asp Thr Asp Gly Asp Asn Asp Val Phe Gly Ser Gly Asn Asp Thr
1               5                       10                      15

Arg Asn Asn Asp Asp Lys Lys Lys Glu Glu Met Lys Gln Asn Ile Ser
            20                      25                  30

Asp Asn Ser Gln Ile Ile Ser Thr Arg Asp His Glu Ala Asp Ile Ile
            35                  40                  45

Gly Ser Ile Ser Lys Glu Asp Leu Ser Lys Ile Val Val Arg Val Asp
    50                      55                  60

Arg His Asp Ala Leu Ser Ala Asn Asp Val Gln Ser Phe Arg Glu Ala
65                      70                  75                  80

Met Ile Asn Phe Met Arg Asp Lys Asp Pro Asn Arg Asn Gln Pro Ser
                85                  90                  95

Asp Lys Leu Ile Ile Ala Met Glu Val Gly Val Tyr Gln Met Val Ile
            100                 105                 110

Asn Leu Gly Thr Ser Ala Lys Leu Gly Asn Ala Asn Asn Leu Glu Phe
        115                 120                 125

Thr Ile Ala Tyr Asp Gln Glu Thr Arg Thr Tyr Lys Val Ala Asp Phe
    130                 135                 140

Val Asn Tyr Met Gln Ser Arg Met Arg Asn Ser Pro Asn Val Val Arg
145                 150                 155                 160

Gln Tyr Ala Arg Ala Met Glu Lys Thr Ile Asn Asn Ile Arg Ser Ala
                165                 170                 175

Gly Ile Ile Asn Ser Asn Gly Val Leu Ala Ala Lys His Gly Val Leu
            180                 185                 190

Ala Ser Tyr Arg Asn Ser Tyr Ser Asp Phe Ala Val Gly Phe Gly Asn
        195                 200                 205

Asp Thr Thr Asp Ala Gln Leu Thr Ser Leu Met Leu Ala Arg Lys Gln
    210                 215                 220

Ala Leu Cys Lys Gly Glu Gly Gly Ser Val Glu His Tyr Asn Thr Met
225                 230                 235                 240

Gln Leu Ala Asn Leu Lys His Pro Cys
            245

FIGURE 6B
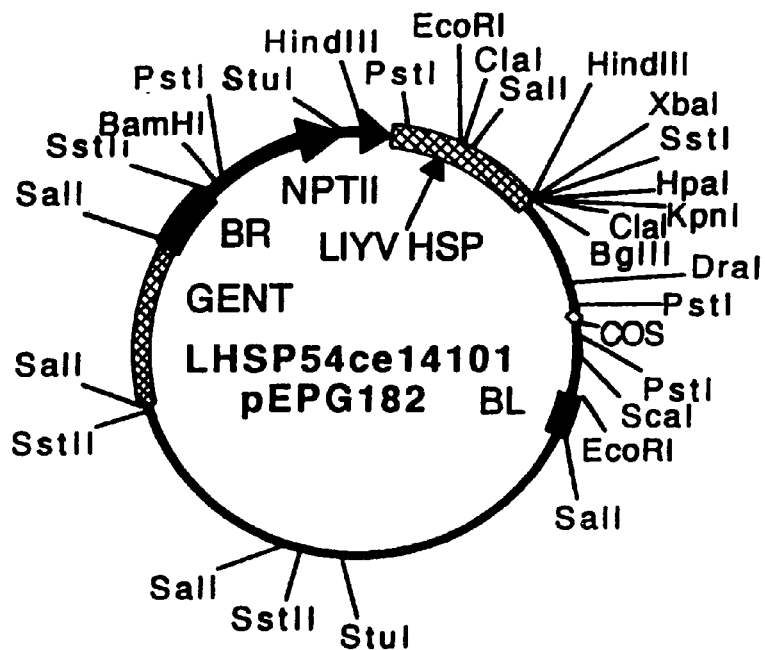
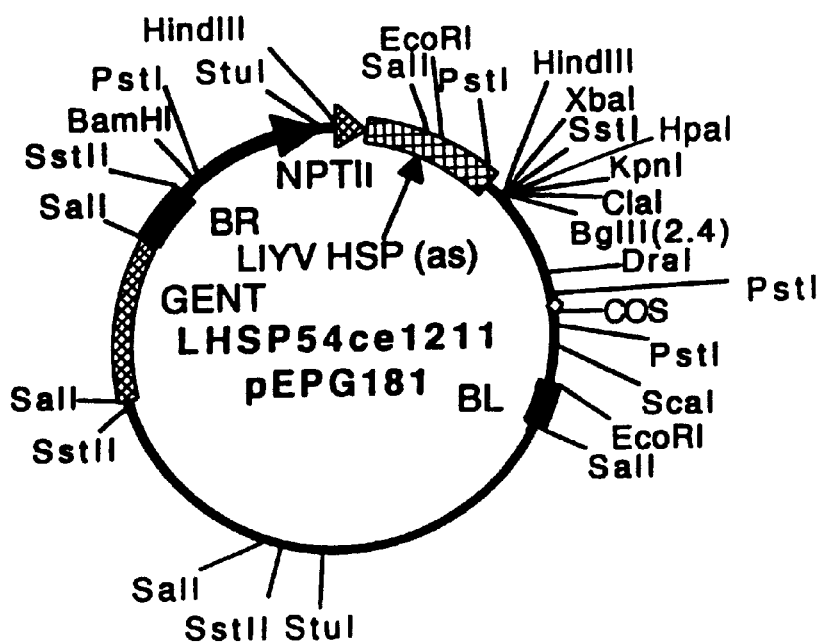

FIGURE 7A

```
SEQ ID NO:10                  Eco RI  Nco I
SEQ ID NO:7    RMM_308  GTTTCGAATTCACCATGGAGGAGATTGTAAGG                                                                                  SEQ ID NO:8
                   663  GTTTCAAATTCAAAATGAGAGAGATTGTAAGGTAGGCTTAGATTCGGTACTACTTTTAGTACTGTTAGTACTCTTGTGAATAACAGTATGTATGTGTGAG  762
                          M  R  D  C  K  V  G  L  D  F  G  T  T  F  S  T  V  S  T  L  V  N  N  S  H  Y  V  L  R

763  ATTAGGTGATTCGGCTTACATACCAACGTGTATTGTGCTATCACACCTGGAGGTGAGGCCATCATAGAGGTGCTGCAGAGTACTTCGGAGATGATACA   862
                          L  G  D  S  A  Y  I  P  T  C  I  A  I  T  P  G  G  E  A  I  I  G  G  A  A  E  V  L  S  G  D  D  T

863  CCTCACTGCTTTTCCTTTCTATGATTGAAGAGGTGGGTGTTGATGACAATACATTCAAATTGCTATGAATAAATTAGACCAATACGTAGCAGAGT       962
                          P  H  C  F  F  Y  D  L  K  R  W  V  G  V  D  D  N  T  F  K  F  A  H  N  K  I  R  P  K  Y  V  A  E  L

963  TGGTTGAAGGTGAGGTTTATTAACCGGCATCAATAAAGGATTTTCTATAAGCTGTCTGTTAAGCAATAATAATAAGGCTTATATAGAAACTATTGTTAG  1062
                          V  E  G  E  V  Y  L  T  G  I  N  K  G  F  S  I  K  L  S  V  K  Q  L  I  K  A  Y  I  E  T  I  V  R

1063  GTGTAGCCAGCTCATATTCTTGAGAGTCATAGATTAAATCAGTCGTGTCCGGCCGATTATAAGAATGCCAGAGAATGCTGCAAGATCGGTGTTG        1162
                          L  L  A  S  S  Y  S  L  R  V  I  D  L  N  Q  S  V  P  A  D  Y  K  N  A  Q  R  L  A  A  R  S  V  L

1163  AAAGGCTTATCATTCCTGTGTAGAATATAAATGAACCATCAGCAGCAGCAGTATCCAATTATATAACTATTTCTAGTT                         1262
                          K  A  L  S  F  P  C  R  R  I  I  N  E  P  S  A  A  A  V  Y  C  V  S  R  Y  P  N  Y  N  Y  F  L  V

1263  ATGATTTGAGGAGGTACCTTTGATGTGTCGCTAAGTAGTCTATGTCACTGTTATATACCGAAGGAGACTGCGTCTTAGGCGTAG                   1362
                          D  F  G  G  G  T  F  D  V  S  L  I  G  K  Y  K  S  Y  T  V  I  D  T  E  G  D  S  F  L  G  G  R

1363  AGATATGACAAGACAAGAGTATAGAAGACTATCCAGTGTGGGCAAATATAATAATAAAGAAGTCATTCCAGCTACTTATTAGCTTTAATAAAGAAGAGTAAT  1462
                          D  I  D  K  S  I  E  D  Y  L  V  G  K  Y  N  I  K  K  V  I  P  A  T  Y  L  A  L  I  K  E  E  C  N

1463  AATACCAATAAGAGTATTTTTACGATACTCGTTTGATGACGGATCGTCAGTGTGGAATCTCTAAGAGTGAATAGAAAATGCGTTCGTCCATTTG         1562
                          N  T  N  K  S  I  F  T  I  L  F  D  D  G  S  V  Q  V  V  E  F  S  K  S  E  L  E  K  C  V  R  P  F  V

1563  TCGAAAGATCGATCAAACTATAAAATGATTGGTGTACGAAACAAGTTGACATCGGAGTCATTTATATGGTTGAGTTCATCTCTATTACACCAGT          1662
                          E  R  S  I  K  L  I  N  D  V  V  R  N  K  L  T  S  G  V  I  Y  H  V  G  G  S  S  L  L  Q  P  V

1663  ACAAGATATGGTGAGTCTTACGGTGAGATCGTTTATATAGGATTAACCTAGTTGCAATTGCAATCGTTAAGCGTTCTTCTTAGGTTGTTCGGTTGCAT     1762
                          Q  D  M  V  R  S  Y  A  S  T  K  G  L  T  L  V  A  D  Q  D  M  R  S  A  V  S  Y  G  C  S  V  L  H

1763  AAGTTGGAAGTCAATAAGGAGATCGTTTATATAGAAATTGTCAATTGCAATCCGTTATGCATCCGTCATCAGAACCATCATCACAGAAAAC           1862
                          K  L  E  V  N  K  E  I  V  I  I  D  C  N  S  H  P  L  S  D  I  S  F  N  C  D  P  E  P  I  I  R  K  P

1863  CGATGTCAATACCTACCTGATAAGATGCGACATGCGACACCGTCGACGACCGCGACATGAATAAAACGATGCGAATATATATGAAGGATCAAATCTCTCATCCTGA  1962
                          M  S  I  P  Y  T  H  T  V  K  M  R  H  D  R  P  L  K  T  I  V  N  I  Y  E  G  S  N  L  F  M  P  E

1963  AAATGATTGGTTGATATCTTCCAATAATCAATACAACAGATTTGCTAAAGTAGGAGAAGAGTATAGTAAGGTCTACGAATATGATATTGACGTATCATA    2062
                          N  D  W  L  I  S  S  N  I  N  T  T  D  F  A  K  V  G  E  E  Y  S  K  V  Y  E  Y  D  I  D  G  I  I

2063  ACCCTAAAAATAAGGAATGGAAGTCACTGGAAAATGTCACATTACCGAACTCGTTACTGAGTGTAACATAACCATCGTTAATTAACTC                2162
                          T  L  K  I  R  N  E  V  T  G  K  M  F  T  L  P  N  S  F  T  K  S  D  N  I  K  P  I  T  F  K  L  T  Q
```

FIGURE 7B

```
2163  AATTGTCAAACACTGATGACTTAGCGACGTTGACGTCTCCTAGGTTATCACGACAAAAACTTGAGAGGTTTACGGGTTATTAATGTTCCAACAAT  2262
       L  S  N  T  D  D  L  A  T  L  T  S  L  L  G  Y  H  D  K  N  F  E  R  F  Y  G  L  F  N  V  P  T  I

2263  ATTGATCAAGGAAATAGACAAATTGGGCGGATTTAAACTTGTATCGTCTCAAAAGTGCTAATTTAAAGAAGTCTAATTTTAAAGGAGTTGTTTCGTTAGAG  2362
       L  I  K  E  I  D  K  L  G  G  F  K  T  L  Y  R  R  L  K  S  H  N  A  N  F  *  R  R  R  L  F  S  L  E

2363  TCAATTTAATTTAAAGTGAGAAGATCAGTTAAAGAAACATAACACCAAAAGTCAGTTGAATGTTGATGACAGAATTGCTGTAACATGC  2462
       S  I  *  F  K  V  R  R  S  V  K  R  N  S  T  N  I  T  P  K  V  S  *  RMH 309               Nco I

2463  TTTCAAACGC   2472                                              CTGTCTTAACGACATGGTACC
      TAGGTTTGCG                                                                           Nco I
      BamHI

SEQ ID NO:9
```

FIGURE 8A

Sequence I.D. No. 6

```
ATGAGAGATT GTAAGGTAGG CTTAGATTTC GGTACTACTT TTAGTACTGT TAGTACTCTT    60
GTGAATAACA GTATGTATGT GTTGAGATTA GGTGATTCGG CTTACATACC AACGTGTATT   120
GCTATCACAC CTGGAGGTGA GGCCATCATA GGAGGTGCTG CAGAAGTACT TTCGGGAGAT   180
GATACACCTC ACTGCTTTTT CTATGATTTG AAGAGGTGGG TTGGTGTTGA TGACAATACA   240
TTCAAATTTG CTATGAATAA AATTAGACCC AAATACGTAG CAGAGTTGGT TGAAGGTGAG   300
GTTTATTTAA CCGGCATCAA TAAAGGATTT TCTATAAAGC TGTCTGTTAA GCAATTAATA   360
AAGGCTTATA TAGAAACTAT TGTTAGGTTG TTAGCCAGCT CATATTCTTT GAGAGTCATA   420
GATTAAAATC AGTCTGTTCC GGCCGATTAT AAGAATGCTC AGAGATTAGC TGCAAGATCG   480
GTGTTGAAAG CGTTATCATT TCCTTGTCGT AGGATTATAA ATGAACCATC AGCAGCAGCA   540
GTCTACTGTG TGTCAAGGTA TCCTAATTAT AACTATTTCT TAGTTTATGA TTTTGGAGGA   600
GGTACCTTTG ATGTGTCGCT CATAGTAAAA TATAAGTCTT ATGTCACTGT TATAGATACC   660
GAAGGAGACT CGTTCTTAGG CGGTAGAGAT ATAGACAAGA GTATAGAAGA CTATCTAGTG   720
GGCAAATATA ATATAAAGAA AGTCATTCCA GCTACTTATT TAGCTTTAAT AAAAGAAGAG   780
TGTAATAATA CCAATAAGAG TATTTTTACG ATACTGTTTG ATGACGGATC TGTTCAAGTT   840
GTGGAATTCT CTAAGAGTGA ATTAGAGAAA TGCGTTCGTC CATTGTCGA AAGATCGATC   900
AAACTTATAA ATGATGTGGT GGTACGAAAC AAGTTGACAT CGGGAGTCAT TTATATGGTT   960
```

FIGURE 8B

```
GGAGGTTCAT CTCTATTACA ACCAGTACAA GATATGGTGA GGTCTTACGC GTCGACTAAG    1020
GGATTAACCT TAGTTGCAGA TCAAGATATG AGAAGCGCAG TGTCTTACGG TTGTTCGGTT    1080
TTGCATAAGT TGGAAGTCAA TAAGGAGATC GTTTATATAG ATTGCAATTC GCATCCGTTA    1140
TCGGACATCT CGTTCAATTG TGATCCAGAA CCCATCATAC GAAAACCGAT GTCAATACCT    1200
TACACTCACA CCGTTAAGAT GCGACATGAC CGTCCTTTAA AAACGATAGT GAATATATAT    1260
GAAGGATCAA ATCTCTTCAT GCCTGAAAAT GATTGGTTGA TATCTTCCAA TATCAATACA    1320
ACAGATTTTG CTAAAGTAGG AGAAGAGTAT AGTAAGGTCT ACGAATATGA TATTGACGGT    1380
ATCATAACCC TAAAAATAAG GAATGAAGTC ACTGGGAAAA TGTTCACATT ACCGAACTCG    1440
TTCACTAAGA GTGATAACAT AAAACCCATC ACTTTTAAAT TAACTCAATT GTCAAACACT    1500
GATGACTTAG CGACGTTGAC GTCTCTCCTA GGTTATCACG ACAAAAAACTT TGAGAGGTTT    1560
TACGGGTTAT TTAATGTTCC AACAATATTG ATCAAGGAAA TAGACAAATT GGGCGGATTT    1620
AAAACTTTGT ATCGTCGTCT CAAAAGTATG AATGCTAATT TTTAA                    1665
```

FIGURE 9A

Sequence I.D. No. 7

```
Met Arg Asp Cys Lys Val Gly Leu Asp Phe Gly Thr Thr Phe Ser Thr
1             5                   10                  15
Val Ser Thr Leu Val Asn Asn Ser Met Tyr Val Leu Arg Leu Gly Asp
             20                  25                  30
Ser Ala Tyr Ile Pro Thr Cys Ile Ala Ile Thr Pro Gly Gly Glu Ala
         35                  40                  45
Ile Ile Gly Gly Ala Ala Glu Val Leu Ser Gly Asp Asp Thr Pro His
     50                  55                  60
Cys Phe Phe Tyr Asp Leu Lys Arg Trp Val Gly Val Asp Asp Asn Thr
65                  70                  75                  80
Phe Lys Phe Ala Met Asn Lys Ile Arg Pro Lys Tyr Val Ala Glu Leu
                 85                  90                  95
Val Glu Gly Glu Val Tyr Leu Thr Gly Ile Asn Lys Gly Phe Ser Ile
             100                 105                 110
Lys Leu Ser Val Lys Gln Leu Ile Lys Ala Tyr Ile Glu Thr Ile Val
         115                 120                 125
Arg Leu Leu Ala Ser Ser Tyr Ser Leu Arg Val Ile Asp Leu Asn Gln
    130                 135                 140
Ser Val Pro Ala Asp Tyr Lys Asn Ala Gln Arg Leu Ala Ala Arg Ser
145                 150                 155                 160
Val Leu Lys Ala Leu Ser Phe Pro Cys Arg Arg Ile Ile Asn Glu Pro
                165                 170                 175
Ser Ala Ala Ala Val Tyr Cys Val Ser Arg Tyr Pro Asn Tyr Asn Tyr
            180                 185                 190
Phe Leu Val Tyr Asp Phe Gly Gly Gly Thr Phe Asp Val Ser Leu Ile
        195                 200                 205
Gly Lys Tyr Lys Ser Tyr Val Thr Val Ile Asp Thr Glu Gly Asp Ser
    210                 215                 220
Phe Leu Gly Gly Arg Asp Ile Asp Lys Ser Ile Glu Asp Tyr Leu Val
225                 230                 235                 240
Gly Lys Tyr Asn Ile Lys Lys Val Ile Pro Ala Thr Tyr Leu Ala Leu
                245                 250                 255
Ile Lys Glu Glu Cys Asn Asn Thr Asn Lys Ser Ile Phe Thr Ile Leu
            260                 265                 270
Phe Asp Asp Gly Ser Val Gln Val Val Glu Phe Ser Lys Ser Glu Leu
        275                 280                 285
```

FIGURE 9B

Glu Lys Cys Val Arg Pro Phe Val Glu Arg Ser Ile Lys Leu Ile Asn
    290                        295                     300

Asp Val Val Val Arg Asn Lys Leu Thr Ser Gly Val Ile Tyr Met Val
305                310                     315                  320

Gly Gly Ser Ser Leu Leu Gln Pro Val Gln Asp Met Val Arg Ser Tyr
                325                   330                335

Ala Ser Thr Lys Gly Leu Thr Leu Val Ala Asp Gln Asp Met Arg Ser
           340                 345                350

Ala Val Ser Tyr Gly Cys Ser Val Leu His Lys Leu Glu Val Asn Lys
      355               360                365

Glu Ile Val Tyr Ile Asp Cys Asn Ser His Pro Leu Ser Asp Ile Ser
    370                375               380

Phe Asn Cys Asp Pro Glu Pro Ile Ile Arg Lys Pro Met Ser Ile Pro
385                390                 395               400

Tyr Thr His Thr Val Lys Met Arg His Asp Arg Pro Leu Lys Thr Ile
           405                 410               415

Val Asn Ile Tyr Glu Gly Ser Asn Leu Phe Met Pro Glu Asn Asp Trp
          420              425               430

Leu Ile Ser Ser Asn Ile Asn Thr Thr Asp Phe Ala Lys Val Gly Glu
      435               440              445

Glu Tyr Ser Lys Val Tyr Glu Tyr Asp Ile Asp Gly Ile Ile Thr Leu
    450                455               460

Lys Ile Arg Asn Glu Val Thr Gly Lys Met Phe Thr Leu Pro Asn Ser
465                470                 475              480

Phe Thr Lys Ser Asp Asn Ile Lys Pro Ile Thr Phe Lys Leu Thr Gln
           485                 490                495

Leu Ser Asn Thr Asp Asp Leu Ala Thr Leu Thr Ser Leu Leu Gly Tyr
          500                 505                510

His Asp Lys Asn Phe Glu Arg Phe Tyr Gly Leu Phe Asn Val Pro Thr
      515               520               525

Ile Leu Ile Lys Glu Ile Asp Lys Leu Gly Gly Phe Lys Thr Leu Tyr
    530                535               540

Arg Arg Leu Lys Ser Met Asn Ala Asn Phe
545                550

FIGURE 10A

```
                    Eco RI  Nco I
SEQ ID NO:13  RMM 301 TATGAGAGCATAGAATTCCCCATGGACATA
SEQ ID NO:15    1 TATGAGAGCATAATAGACCTGATGGACATAATATCACCAGGGTGGCCTTTACAATTATTTACACAGGACGTTGATTTTGAATACTCAGATTACTACT  100
SEQ ID NO:12         M  D  I  I  S  P  G  V  A  F  Y  N  Y  L  H  R  T  L  I  F  E  Y  S  D  Y  Y  L

101 TACCTCCATGTGAAGATTTGAGAATAACTTTGAGCAAGTCCAAACCATACCCCTGGAGCTATGTGTCTCGAAAATTCTCGGGAAGGGAGAAAGAAA  200
           P  P  C  E  D  L  R  I  T  L  S  K  S  K  P  Y  H  P  G  A  Y  V  V  V  S  K  I  L  G  K  G  E  R  N

201 CAGACCGAACACTTGGAAACAAGTTATTCAGTCACTATCCACAGAATTTTAATGGCCAATTATCAATTATCACAAGTAGATGTTAAAGAAGCGCACAA  300
           R  P  N  T  W  K  Q  V  I  Q  S  L  S  H  R  N  F  N  A  P  I  I  N  H  K  L  D  V  K  R  S  A  Q

301 ATACTATATGACTCGGTGGTGAAATCGTTAAGACAGACAGGTTGACTGAGTGTATGAACCTATTTACCTGACCTTTTCAAAATCGGTAAGTGGTTGG  400
           I  L  Y  D  S  V  V  K  S  L  R  Q  D  R  L  T  E  W  Y  E  P  I  L  P  D  L  F  K  I  G  K  W  L  D

401 ATGATAGAGATGTAGCAAATATCGTATGTTGAACCGTAGACTTTGCCAGTTTAGCAGACAAGTTCAAACTCTCAACCTCATGGTTAAGGGTGA  500
           D  R  D  G  S  K  Y  R  M  L  N  R  R  L  D  F  A  S  L  A  D  K  F  K  T  L  N  L  M  V  K  G  E

501 GACCAAGCCCAAGATGGATCTTAGCACATACGACAGTTACAATGCTCCAGCTAATATAGTCGTTTATTACCAGCAGATAGTCAATTTGTATTTTCACCATG  600
           T  K  P  K  M  D  L  S  T  Y  D  S  Y  N  A  P  A  N  I  V  Y  Y  Q  Q  I  V  N  L  Y  F  S  P  M

601 TTTTTAGAGTGTTTCGCAAGGTTGACTTACTGTTAAGTGATAAAATCGTTCTATACAGGGCATGAACACAGACGTTCTAGCTGAGTTAATTGAAAGCA  700
           F  L  E  C  F  A  R  L  T  Y  C  L  S  D  K  I  V  L  Y  S  G  M  N  T  D  V  L  A  E  L  I  E  S  K

701 AACTACCATTAGGTCTTAACGCATATCACGCTTGAGATAGATTTCAGCAAATTTGATAAGTCTCAAGGCACATGCTTCAAATTATATGAAGAAATGAT  800
           L  P  L  G  L  N  A  Y  H  T  L  E  I  D  F  S  K  F  D  K  S  Q  G  T  C  F  K  L  Y  E  E  M  M
```

FIGURE 10B

```
 801  GTATAAGATGTTTGGATTTTCTCCTGAGTGTACGATCAGACTTCAAATACACGGAGTACTTCTGTAGAGGAAAGCAACTTGTGGAGTGGATCCGAG   900
       Y  K  M  F  G  F  S  P  E  L  Y  D  R  D  F  K  Y  T  E  Y  F  C  R  A  K  A  T  C  G  V  D  L  E

901  TTAGGAACACGGCAGAACTGGATCTCCAAACACTTGGTTGTCTAACACTCTAGTTACTTTAGGTATGATGTTATCATCTTACGACATTGATGATATAG  1000
       L  G  T  Q  R  R  T  G  S  P  N  T  W  L  S  N  T  L  V  T  L  G  M  M  L  S  S  Y  D  I  D  D  I  D

1001  ACCTACTCCTTGTTAGCGGGGATGACAGTTTAATTTTTTCCAGGAAACATCTACCGAATAAAACCCAAGAGATAAACAAAAACTTTGGGATGGAGGCCAA  1100
       L  L  L  V  S  G  D  D  S  L  I  F  S  R  K  H  L  P  N  K  T  Q  E  I  N  K  N  F  G  M  E  A  K

1101  GTATATAGAGAAATCATCTCCATACTTCTGCTCCAAATTCATAGTGTGAGTTAAATGGTAAGTTGAAAGTCATACCTGATCCAATACGATTCTTGAAAAA  1200
       Y  I  E  K  S  S  P  Y  F  C  S  K  F  I  V  E  L  N  G  K  L  K  V  I  P  D  P  I  R  F  F  E  K

1201  TTGTCAATTCCAAATTAGACAAGAAGATTCGTAAACGGAAGCGTTCATATCATTCAAAGATTTGATGAAAGATATGATAATGATG  1300
       L  S  I  P  I  R  Q  E  D  F  V  N  G  S  V  V  K  E  R  F  I  S  F  K  D  L  M  K  E  Y  D  N  D  V

1301  TCGCCGTTATACGCATTGACGAAGCAGTGTGTTATAGATACAGCATACCGGTTGCTGTTCCTACGCAGCATTGTGCTATATACACTGTTGCATGTCGAA  1400
       A  V  I  R  I  D  E  A  V  C  Y  R  Y  S  I  P  V  G  C  S  Y  A  A  L  C  Y  I  H  C  C  M  S  N

1401  TTTTGTTTCTTTCCGTAGGATTATGACAATTGTGTGAAATTGTGGATTAAGATGACACTTCAAGTTTTATCGCCTCGATTGAAAAAGACAATTTGAT  1500
       F  V  S  F  R  R  I  Y  D  N  C  E  I  V  W  I  *
                                                                                              CTGTTAAGGTA
                                                                                              Nco I

1501  GGATTGCTTGATCAG        1515
      CCTTAAGAACTAGTC        RMM 302
      Eco RI
```

SEQ ID NO:12

SEQ ID NO:15
SEQ ID NO:14

FIGURE 12A

Sequence I.D. No. 11

| | | | | | |
|---|---|---|---|---|---|
| ATGGACATAA | TATCACCAGG | GGTGGCCTTT | TACAATTATT | TACACAGGAC | GTTGATTTTT | 60 |
| GAATACTCAG | ATTACTACTT | ACCTCCATGT | GAAGATTTGA | GAATAACTTT | GAGCAAGTCC | 120 |
| AAACCATACC | ACCCTGGAGC | TTATGTTGTC | TCGAAAATTC | TCGGGAAGGG | AGAAAGAAAC | 180 |
| AGACCGAACA | CTTGGAAACA | AGTTATTCAG | TCACTATCTC | ACAGGAATTT | TAATGCGCCA | 240 |
| ATTATCAATC | ACAAGTTAGA | TGTTAAAAGA | AGCGCACAAA | TACTATATGA | CTCGGTGGTG | 300 |
| AAATCGTTAA | GACAAGACAG | GTTGACTGAG | TGGTATGAAC | CTATTTTACC | TGACCTTTTC | 360 |
| AAAATCGGTA | AGTGGTTGGA | TGATAGAGAT | GGTAGCAAAT | ATCGTATGTT | GAACCGTAGA | 420 |
| CTAGACTTTG | CCAGTTTAGC | AGACAAGTTC | AAAACTCTCA | ACCTCATGGT | TAAGGGTGAG | 480 |
| ACCAAGCCCA | AGATGGATCT | TAGCACATAC | GACAGTTACA | ATGCTCCAGC | TAATATAGTC | 540 |
| TATTACCAGC | AGATAGTCAA | TTTGTATTTT | TCACCCATGT | TTTTAGAGTG | TTTCGCAAGG | 600 |
| TTGACTTACT | GTTAAGTGA | TAAAATCGTT | CTATACAGCG | GCATGAACAC | AGACGTTCTA | 660 |
| GCTGAGTTAA | TTGAAAGCAA | ACTACCATTA | GGTCTTAACG | CATATCACAC | GCTTGAGATA | 720 |
| GATTTCAGCA | AATTTGATAA | GTCTCAAGGC | ACATGCTTCA | AATTATATGA | AGAAATGATG | 780 |
| TATAAGATGT | TTGGATTTTC | TCCTGAGTTG | TACGATCGAG | ACTTCAAATA | CACGGAGTAC | 840 |
| TTCTGTAGAG | CGAAAGCAAC | TTGTGGAGTG | GATCTCGAGT | TAGGAACACA | GCGCAGAACT | 900 |

FIGURE 12B

```
GGATCTCCAA ACACTTGGTT GTCTAACACT CTAGTTACTT TAGGTATGAT GTTATCATCT   960
TACGACATTG ATGATATAGA CCTACTCCTT GTTAGCGGGG ATGACAGTTT AATTTTTTCC  1020
AGGAAACATC TACCGAATAA AACCCAAGAG ATAAACAAAA ACTTTGGGAT GGAGGCCAAG  1080
TATATAGAGA AATCATCTCC ATACTTCTGC TCCAAATTCA TAGTTGAGTT AAATGGTAAG  1140
TTGAAAGTCA TACCTGATCC AATACGATTC TTTGAAAAAT TGTCAATTCC AATTAGACAA  1200
GAAGATTTCG TAAACGGAAG CGTAGTCAAA GAACGGTTCA TATCATTCAA AGATTTGATG  1260
AAAGAATATG ATAATGATGT CGCCGTTATA CGCATTGACG AAGCAGTGTG TTATAGATAC  1320
AGCATACCGG TTGGCTGTTC CTACGCAGCA TTGTGCTATA TACACTGTTG CATGTCGAAT  1380
TTTGTTTCTT TCCGTAGGAT TTATGACAAT TGTGAAATTG TGTGGATT              1428
```

FIGURE 13A

Sequence I.D. No. 12

```
Met Asp Ile Ile Ser Pro Gly Val Ala Phe Tyr Asn Tyr Leu His Arg
1               5                   10                  15

Thr Leu Ile Phe Glu Tyr Ser Asp Tyr Tyr Leu Pro Pro Cys Glu Asp
            20                  25                  30

Leu Arg Ile Thr Leu Ser Lys Ser Lys Pro Tyr His Pro Gly Ala Tyr
        35                  40                  45

Val Val Ser Lys Ile Leu Gly Lys Gly Glu Arg Asn Arg Pro Asn Thr
    50                  55                  60

Trp Lys Gln Val Ile Gln Ser Leu Ser His Arg Asn Phe Asn Ala Pro
65                  70                  75                  80

Ile Ile Asn His Lys Leu Asp Val Lys Arg Ser Ala Gln Ile Leu Tyr
                85                  90                  95

Asp Ser Val Val Lys Ser Leu Arg Gln Asp Arg Leu Thr Glu Trp Tyr
            100                 105                 110

Glu Pro Ile Leu Pro Asp Leu Phe Lys Ile Gly Lys Trp Leu Asp Asp
        115                 120                 125

Arg Asp Gly Ser Lys Tyr Arg Met Leu Asn Arg Arg Leu Asp Phe Ala
    130                 135                 140

Ser Leu Ala Asp Lys Phe Lys Thr Leu Asn Leu Met Val Lys Gly Glu
145                 150                 155                 160

Thr Lys Pro Lys Met Asp Leu Ser Thr Tyr Asp Ser Tyr Asn Ala Pro
                165                 170                 175

Ala Asn Ile Val Tyr Tyr Gln Gln Ile Val Asn Leu Tyr Phe Ser Pro
            180                 185                 190

Met Phe Leu Glu Cys Phe Ala Arg Leu Thr Tyr Cys Leu Ser Asp Lys
        195                 200                 205

Ile Val Leu Tyr Ser Gly Met Asn Thr Asp Val Leu Ala Glu Leu Ile
    210                 215                 220

Glu Ser Lys Leu Pro Leu Gly Leu Asn Ala Tyr His Thr Leu Glu Ile
225                 230                 235                 240

Asp Phe Ser Lys Phe Asp Lys Ser Gln Gly Thr Cys Phe Lys Leu Tyr
                245                 250                 255

Glu Glu Met Met Tyr Lys Met Phe Gly Phe Ser Pro Glu Leu Tyr Asp
        260                 265                 270

Arg Asp Phe Lys Tyr Thr Glu Tyr Phe Cys Arg Ala Lys Ala Thr Cys
    275                 280                 285
```

FIGURE 13B

Gly Val Asp Leu Glu Leu Gly Thr Gln Arg Arg Thr Gly Ser Pro Asn
    290                   295                   300

Thr Trp Leu Ser Asn Thr Leu Val Thr Leu Gly Met Met Leu Ser Ser
305                    310               315              320

Tyr Asp Ile Asp Asp Ile Asp Leu Leu Val Ser Gly Asp Asp Ser
                325             330              335

Leu Ile Phe Ser Arg Lys His Leu Pro Asn Lys Thr Gln Glu Ile Asn
           340             345             350

Lys Asn Phe Gly Met Glu Ala Lys Tyr Ile Glu Lys Ser Ser Pro Tyr
       355            360             365

Phe Cys Ser Lys Phe Ile Val Glu Leu Asn Gly Lys Leu Lys Val Ile
    370              375             380

Pro Asp Pro Ile Arg Phe Phe Glu Lys Leu Ser Ile Pro Ile Arg Gln
385                    390             395             400

Glu Asp Phe Val Asn Gly Ser Val Val Lys Glu Arg Phe Ile Ser Phe
            405            410             415

Lys Asp Leu Met Lys Glu Tyr Asp Asn Asp Val Ala Val Ile Arg Ile
         420             425            430

Asp Glu Ala Val Cys Tyr Arg Tyr Ser Ile Pro Val Gly Cys Ser Tyr
       435            440            445

Ala Ala Leu Cys Tyr Ile His Cys Cys Met Ser Asn Phe Val Ser Phe
   450                455              460

Arg Arg Ile Tyr Asp Asn Cys Glu Ile Val Trp Ile
465                  470             475

FIGURE 14

```
SEQ ID NO:18  RMM 398          Eco RI  Nco I
SEQ ID NO:20          GATGGAATTCCATGGTAATGATGTCGCCG
SEQ ID NO:17  RMM   1 GATGAAAGAATATGATAATGATGTCGCCGTTATACGCCGTTATGAGAAGCAGTGTGTTATAGATACAGCATACCGGTTGGCTGTTCCTACGCAGCATTGTGC  100
                       M  I  M  S  P  L  Y  A  L  T  K  Q  C  V  I  D  T  A  Y  R  L  A  V  P  T  Q  H  C  A

101 TATATACTGTTGCATGTCGAATTTGTTCTTCCGTAGGATTATGACAATTGTGAAATTGTGAATTAAGATGGACACTTCAAGTTTATCGCC  200
                 I  Y  T  V  A  C  R  I  L  F  L  S  V  G  F  M  T  I  V  K  L  C  G  F  K  M  D  T  S  F  I  A

201 TCGATTGAAAAGACAATTTGATGGATTGCTTGATCAGTTAGTGAGATGAGAGATCGTCTTAGTGTGCAACGATTGTCCAATATTGAATTATGGAG  300
                 S  I  E  K  D  N  L  M  D  C  L  I  S  L  V  E  M  R  D  R  L  R  L  C  N  D  F  P  I  L  N  Y  G  V

301 TTAACATTTTAGAATTACTAGATAGGCAAAAGTTGAATAAATTAATAATTAAAGAATTGTATGTAATTAGAGAACTAATAACAATAAATATAAGTAA  400
                 N  I  L  E  L  L  I  G  K  R  L  N  K  I  N  N  L  K  N  C  Y  V  I  R  E  L  I  T  I  N  I  S  K

401 GGAGTGGGTTGGAAAGCAAGCTCTAAAAGTTGGCTTACATGTCCTCTAAATCTATCTCAAGCCGAAAGCAGACATGTCAAGTATCTTTGAGCGACAAA  500
                 E  W  V  G  K  Q  A  L  K  V  G  L  H  C  F  L  N  L  S  Q  A  E  S  R  H  V  K  Y  L  L  S  D  K

501 GAGTCCTTAAATAAGATGAACTTCTCTAGATACTATGTCCCCAAAGTGTAACAGATTTGTATTAGATGTGATTGGGGTGTTATACGTGAATACAGAT  600
                 E  S  L  N  K  M  N  F  S  R  Y  Y  V  P  K  V  V  T  D  L  Y  L  D  L  I  G  V  L  Y  V  N  T  G  Y

601 ACAACATAGATTAGTAGAAAAATTTATTTCGATAAATTAGAATTCAGTTTATGATGGAGGAGGGTTCAAAAGTCCACAGGTTGAATACAATGA  700
                 N  I  D  L  V  E  K  F  I  F  D  K  L  E  E  F  L  V  Y  D  G  E  E  G  F  K  S  P  Q  V  E  Y  N  D

701 CATATGTACGGTCCTACAATTGAAACCAATAATAAATACAATCGTTGCCACACAGATGTTCTATAGTTGACGTGGTGACGTATAGAAAAGGT  800
                 I  C  T  V  Y  N  L  K  P  I  I  K  Y  N  R  W  H  T  D  G  S  I  V  I  E  C  G  D  V  I  G  K  G

801 ATTATAAAACAAAGAAAAAAATTGCAATAAATGATGCCAAAGCGGAGTTCGTAAAGAACTTCAAGAACTTCAAAAAATAAAGAATAGGGTGTTTG  900
                 I  N  K  T  K  K  K  I  C  N  K  *
                                              RMM 399  CCCACAAAGG

SEQ ID NO:19  901 ATAGTAGTTCCCCCC  915
                  TACCACTAGGGGGG
                  NcoI  BamHI
```

FIGURE 16

```
SEQUENCE ID NO 16:

ATGATAATGA TGTCGCCGTT ATACGCATTG ACGAAGCAGT GTGTTATAGA TACAGCATAC    60
CGGTTGGCTG TTCCTACGCA GCATTGTGCT ATATACACTG TTGCATGTCG AATTTTGTTT   120
CTTTCCGTAG GATTATGAC AATTGTGAAA TTGTGTGGAT TTAAGATGGA CACTTCAAGT   180
TTTATCGCCT CGATTGAAAA AGACAATTTG ATGGATTGCT TGATCAGTTT AGTTGAGATG   240
AGAGATCGTC TTAGGTTGTG CAACGATTTC CCAATATTGA ATTATGGAGT TAACATTTTA   300
GAATTACTAA TAGGCAAAAG GTTGAATAAA ATTAATAATT TAAAGAATTG TTATGTAATT   360
AGAGAACTAA TAACAATAAA TATAAGTAAG GAGTGGGTTG GAAAGCAAGC TCTAAAAGTT   420
GGCTTACATT GCTTCTTAAA TCTATCTCAA GCCGAAAGCA GACATGTCAA GTATCTTTTG   480
AGCGACAAAG AGTCCTTAAA TAAGATGAAC TTCTCTAGAT ACTATGTCCC CAAAGTGGTA   540
ACAGATTTGT ATTAGATTT GATTGGGGTG TTATACGTGA ATACAGGATA CAACATAGAT   600
TTAGTAGAAA AATTTATTTT CGATAAATTA GAATTTCTAG TTTATGATGG AGAGGAGGGT   660
TTCAAAAGTC CACAGGTTGA ATACAATGAC ATATGTACGG TCTACAATTT GAAACCAATA   720
ATAAAATACA ATCGTTGGCA CACAGATGGT TCTATAGTTA TAGAGTGTGG TGACGTAATA   780
GGAAAAGGTA TTAATAAAAC AAAGAAAAAA ATTTGCAATA AA                      822
```

FIGURE 17

SEQUENCE ID NO 17:

```
Met Ile Met Met Ser Pro Leu Tyr Ala Leu Thr Lys Gln Cys Val Ile
1               5                   10                  15

Asp Thr Ala Tyr Arg Leu Ala Val Pro Thr Gln His Cys Ala Ile Tyr
            20                  25                  30

Thr Val Ala Cys Arg Ile Leu Phe Leu Ser Val Gly Phe Met Thr Ile
        35                  40                  45

Val Lys Leu Cys Gly Phe Lys Met Asp Thr Ser Ser Phe Ile Ala Ser
    50                  55                  60

Ile Glu Lys Asp Asn Leu Met Asp Cys Leu Ile Ser Leu Val Glu Met
65                  70                  75                  80

Arg Asp Arg Leu Arg Leu Cys Asn Asp Phe Pro Ile Leu Asn Tyr Gly
                85                  90                  95

Val Asn Ile Leu Glu Leu Leu Ile Gly Lys Arg Leu Asn Lys Ile Asn
            100                 105                 110

Asn Leu Lys Asn Cys Tyr Val Ile Arg Glu Leu Ile Thr Ile Asn Ile
        115                 120                 125

Ser Lys Glu Trp Val Gly Lys Gln Ala Leu Lys Val Gly Leu His Cys
    130                 135                 140

Phe Leu Asn Leu Ser Gln Ala Glu Ser Arg His Val Lys Tyr Leu Leu
145                 150                 155                 160

Ser Asp Lys Glu Ser Leu Asn Lys Met Asn Phe Ser Arg Tyr Tyr Val
                165                 170                 175

Pro Lys Val Val Thr Asp Leu Tyr Leu Asp Leu Ile Gly Val Leu Tyr
            180                 185                 190

Val Asn Thr Gly Tyr Asn Ile Asp Leu Val Glu Lys Phe Ile Phe Asp
            195                 200                 205

Lys Leu Glu Phe Leu Val Tyr Asp Gly Glu Glu Gly Phe Lys Ser Pro
    210                 215                 220

Gln Val Glu Tyr Asn Asp Ile Cys Thr Val Tyr Asn Leu Lys Pro Ile
225                 230                 235                 240

Ile Lys Tyr Asn Arg Trp His Thr Asp Gly Ser Ile Val Ile Glu Cys
            245                 250                 255

Gly Asp Val Ile Gly Lys Gly Ile Asn Lys Thr Lys Lys Ile Cys
            260                 265                 270

Asn Lys
```

FIGURE 18

```
           EcoRI  NcoI
       CGGAATTCCATGGTCAAAACGAG<----RMM415
     1 ATGGTCAAAACGAGAATAACCGATAATTCACTGGAGATTAACCTTGAATAATAAACACCTTGAACTTAATCAAATTCAAAACTTGTAGTTCTTTATAT  100
       M  V  K  T  R  I  T  D  N  F  T  G  D  L  T  L  N  I  N  T  S  N  L  I  K  F  K  T  C  S  F  F  I  C

101 GTTATGGAGACGACAAGGATAGTGATGAATTGGGTTGGACTTCAACATCTAGAAGTATTTTCAACATTATAAGGATGGTAAATACATTCGAGA         200
       Y  G  D  D  K  D  R  Y  E  L  G  W  T  S  T  S  R  S  I  F  Q  H  Y  K  D  G  K  Y  I  R  D

201 TTTTAGAATACAAGATCCATTTCCAATTCTATCAGTTCTCAACATTTCCAGTAGTGATTCTAAAATAATAGCAATAGGGAATGAGTTGCCTTTCGTATGAGTAGA  300
       F  R  I  Q  D  P  F  P  I  L  S  G  S  T  F  P  V  V  I  S  K  I  I  A  N  R  V  A  F  R  M  S  R

301 AGATTAAATAATGTTATTGTTGATAAGCTTAAGAATAACATTATAGAGTTTCTATTGTAGTATATTAGATGTGGATACTGGGAAGATTAAACCAAACA         400
       R  L  N  N  V  I  V  D  K  L  K  N  N  I  E  F  L  F  V  V  Y  L  D  V  D  T  G  K  I  K  P  N  T

401 CAATACTCAAAAATTAGATTGTCCAGTCTTTTTATCGTTTTCAGTAACAACGGAAACAATAATCAATTACCATATGAGATAGAGCTACAGACTAA         500
       I  L  K  N  L  D  L  S  S  L  F  I  V  F  S  N  N  G  N  N  K  I  N  L  P  Y  E  I  E  L  Q  T  K

501 AGATAGAGGCATTGTTTACACAAAAATGGGTAATCCTATATCTTACAACTCTCAATAGTTTGAAGATTTATTAGACATAGAAACCAAAGGTGTCGAT         600
       D  R  G  I  V  Y  T  K  M  G  N  P  I  S  Y  N  L  F  N  K  F  E  D  L  L  D  I  E  T  K  G  V  D

601 AAACCCGAAGACAAACCAAACTGTGTTTGACAAGACGTCCTCCTGTTGACAATGCAAGCCCGACATAAGCAAAC         700
       K  P  E  D  K  P  K  P  V  F  D  D  K  G  K  Q  P  T  D  T  V  P  P  V  D  N  G  K  P  D  I  S  K  P
                                                                      RMM416--->CGGGCTGTATTCGTTTG

701 CTGGTGA  707
       W
       GTACCCTCTTGTCCCTAGGTATCT<---RMM416
        NcoI      BamHI
```

SEQ ID NO:23
SEQ ID NO:25
SEQ ID NO:26

SEQ ID NO:24

FIGURE 20

SEQUENCE ID NO 21:

```
ATGTTAGAGG CGGAATGTGA TGAAGTAGAA CTAACCTCCA GAGATGTCGG AGATTATTTG    60
ATGTTCAAAA CGAGAATAAC CGATAATTTC ACTGGAGATT TAACCTTGAA TATAAACACC   120
TCGAACTTAA TCAAATTCAA AACTTGTAGT TTCTTTATAT GTTATGGAGA CGACAAGGAT   180
AGGTATGAAT TGGGTTGGAC TTCAACATCT ACATCTAGAA GTATTTTCA ACATTATAAG    240
GATGGTAAAT ACATTCGAGA TTTTAGAATA CAAGATCCAT TCCAATTCT ATCAGGTTCA    300
ACATTCCAG TAGTGATTTC TAAAATAATA GCGAATAGAG TTGCCTTTCG TATGAGTAGA    360
AGATTAAATA ATGTTATTGT TGATAAGCTT AAGAATAACA TTATAGAGTT TCTATTGTA    420
GTATATTTAG ATGTGGATAC TGGGAAGATT AAACCAAACA CAATACTCAA AAATTTAGAT   480
TTGTCCAGTC TTTTTATCGT TTTCAGTAAC AACGGAAACA ATAAAATCAA TCTACCATAT   540
GAGATAGAGC TACAGACTAA AGATAGAGGC ATTGTTTACA CAAAAATGGG TAATCCTATA   600
TCTTACAACC TCTTCAATAA GTTTGAAGAT TTATTAGACA TAGAAACCAA AGTGTCGAT    660
AAACCCGAAG ACAAACCCAA ACCTGTGTTT GACGACAAAG GCAAGCAACC CACGGATACG   720
GTTCCTCCTG TTGACAATGG CAAGCCCGAC ATAAGCAAAC CTGGTGAGAA ACAGGGAGAC   780
ATAGATATTG CTAGCAAGTT TAATAATATA GTCATGGCAA AATTGAAAGC TCAATCTTCA   840
TCAGATCCAT TGACGAAAAA GCAATGTGAT CAATTGATGT TGAGTCTAAT CAAATGGTTT   900
GAAAAATTTG GAATCACAA AGACAATGCC CGATTGCTGA TATTTCAATT TGGTATATCT   960
TTTTCGACTT CAAAAGAAAA TCTTAACAAT ATCACTAACA ATATTGTTGT AGAGAATGAC  1020
AAAGGTGGGT TTGTAAAAAT TTTAAAAATA GATTACTTGA ACAAACTGTA CGGTTCGATT  1080
CCTGAGTCGC ATACTCACAA TTTAGAAAGA GTTCTACTAA GACATTATGC TCAAGAAATC  1140
TTAATATTAC TAAGAAGCAA AGTGTTAGAA TGGCCTAGGA AATTAGCAAG AAATAAGGGC  1200
ATTTTCGAAC AATATGCCTA CATGGCCTGT GACTTTTTCG ACACCGCAGA ATTAGAATTG  1260
ACGGAGGCTG AGACCACAGC TTTGACGACG GTAAAGTCTT GGACTATGAA CCATTATAAG  1320
AAGAAAAGAC AGATAGTTAA TAGTTCACAA TTAGAATGA                         1359
```

FIGURE 21A

SEQUENCE ID NO 22:

```
Met Leu Glu Ala Glu Cys Asp Glu Val Glu Leu Thr Ser Arg Asp Val
1             5                   10                  15

Gly Asp Tyr Leu Met Phe Lys Thr Arg Ile Thr Asp Asn Phe Thr Gly
            20                  25                  30

Asp Leu Thr Leu Asn Ile Asn Thr Ser Asn Leu Ile Lys Phe Lys Thr
            35                  40                  45

Cys Ser Phe Phe Ile Cys Tyr Gly Asp Asp Lys Asp Arg Tyr Glu Leu
    50                  55                  60

Gly Trp Thr Ser Thr Ser Thr Ser Arg Ser Ile Phe Gln His Tyr Lys
65                      70                  75                  80

Asp Gly Lys Tyr Ile Arg Asp Phe Arg Ile Gln Asp Pro Phe Pro Ile
                85                  90                  95

Leu Ser Gly Ser Thr Phe Pro Val Val Ile Ser Lys Ile Ile Ala Asn
            100                 105                 110

Arg Val Ala Phe Arg Met Ser Arg Arg Leu Asn Asn Val Ile Val Asp
        115                 120                 125

Lys Leu Lys Asn Asn Ile Ile Glu Phe Leu Phe Val Val Tyr Leu Asp
    130                 135                 140

Val Asp Thr Gly Lys Ile Lys Pro Asn Thr Ile Leu Lys Asn Leu Asp
145                 150                 155                 160

Leu Ser Ser Leu Phe Ile Val Phe Ser Asn Asn Gly Asn Asn Lys Ile
                165                 170                 175

Asn Leu Pro Tyr Glu Ile Glu Leu Gln Thr Lys Asp Arg Gly Ile Val
            180                 185                 190

Tyr Thr Lys Met Gly Asn Pro Ile Ser Tyr Asn Leu Phe Asn Lys Phe
        195                 200                 205

Glu Asp Leu Leu Asp Ile Glu Thr Lys Gly Val Asp Lys Pro Glu Asp
    210                 215                 220

Lys Pro Lys Pro Val Phe Asp Asp Lys Gly Lys Gln Pro Thr Asp Thr
225                 230                 235                 240

Val Pro Pro Val Asp Asn Gly Lys Pro Asp Ile Ser Lys Pro Gly Glu
                245                 250                 255

Lys Gln Gly Asp Ile Asp Ile Ala Ser Lys Phe Asn Asn Ile Val Met
            260                 265                 270

Ala Lys Leu Lys Ala Gln Ser Ser Ser Asp Pro Leu Thr Lys Lys Gln
        275                 280                 285
```

FIGURE 21B

Cys Asp Gln Leu Met Leu Ser Leu Ile Lys Trp Phe Glu Lys Phe Gly
    290             295             300

Ile Thr Lys Asp Asn Ala Arg Leu Leu Ile Phe Gln Phe Gly Ile Ser
305             310             315             320

Phe Ser Thr Ser Lys Glu Asn Leu Asn Asn Ile Thr Asn Asn Ile Val
            325             330             335

Val Glu Asn Asp Lys Gly Gly Phe Val Lys Ile Leu Lys Ile Asp Tyr
            340             345             350

Leu Asn Lys Leu Tyr Gly Ser Ile Pro Glu Ser His Thr His Asn Leu
        355             360             365

Glu Arg Val Leu Leu Arg His Tyr Ala Gln Glu Ile Leu Ile Leu Leu
    370             375             380

Arg Ser Lys Val Leu Glu Trp Pro Arg Lys Leu Ala Arg Asn Lys Gly
385             390             395             400

Ile Phe Glu Gln Tyr Ala Tyr Met Ala Cys Asp Phe Phe Asp Thr Ala
            405             410             415

Glu Leu Glu Leu Thr Glu Ala Glu Thr Thr Ala Leu Thr Thr Val Lys
            420             425             430

Ser Trp Thr Met Asn His Tyr Lys Lys Arg Gln Ile Val Asn Ser
        435             440             445

Ser Gln Leu Glu
    450

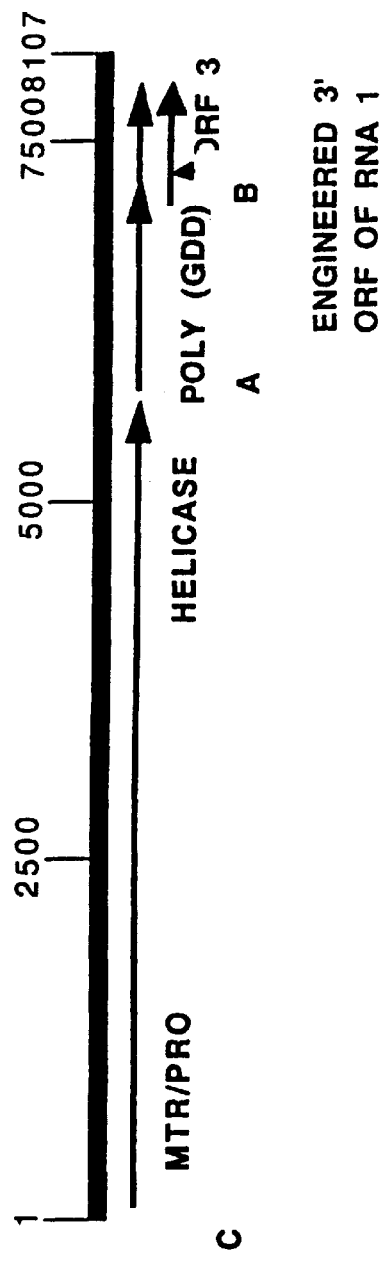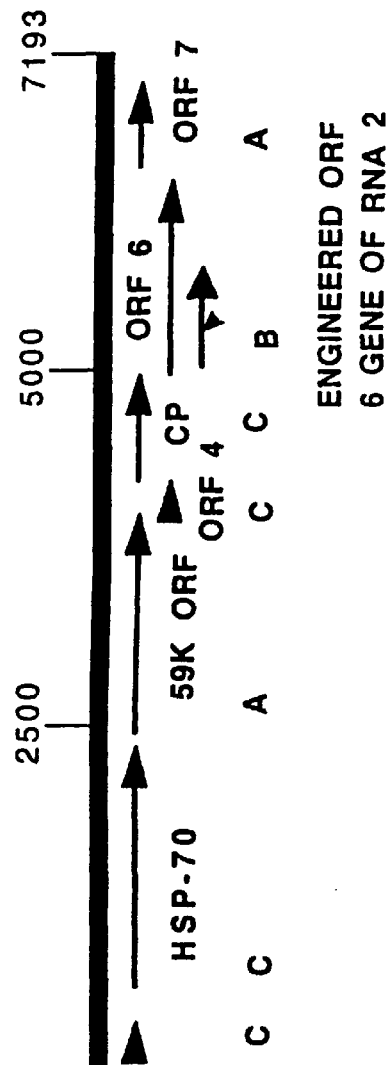
FIGURE 22 ial

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 747 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGGATACAG ATGGAGATAA TGATGTGTTT GGATCGGGAA ACGATACCAG GAATAATGAT    60

GATAAGAAGA AAGAGGAAAT GAAACAAAAC ATTTCTGACA ATTCTCAAAT CATATCAACC   120

AGGGATCATG AAGCTGACAT CATTGGAAGT ATATCGAAAG AGGATTTGTC CAAAATCGTT   180

GTACGCGTCG ACAGGCACGA TGCTCTGAGT GCTAATGATG TTCAAAGTTT TAGAGAAGCT   240

ATGATAAACT TCATGCGAGA CAAAGACCCC AACAGAAATC AACCTAGTGA CAAATTGATT   300

ATTGCTATGG AAGTTGGAGT TTATCAAATG GTCATAAATT TGGGCACTTC GGCTAAATTG   360

GGTAATGCTA ACAATTTAGA ATTTACGATA GCTTACGACC AGGAAACTAG GACATATAAG   420

GTCGCAGATT TTGTGAATTA TATGCAGTCT AGAATGAGGA ACAGTCCAAA TGTTGTTAGG   480

CAATATGCAA GAGCAATGGA AAAGACAATT AACAACATAA GGAGTGCTGG AATCATAAAC   540

AGCAATGGAG TTTTGGCAGC GAAACATGGT GTGTTGGCAT CTTACAGAAA CTCTTACAGC   600

GACTTTGCTG TTGGTTTTGG TAACGACACC ACTGATGCTC AACTCACTTC GCTAATGTTA   660

GCTAGAAAAC AAGCATTATG CAAAGGTGAA GGTGGTTCAG TCGAGCATTA CAATACTATG   720

CAGTTAGCTA ACCTTAAACA TCCATGT                                     747
```

(2) INFORMATION FOR SEQ ID NO:2:

(i) SEQUENCE CHARACTERISTICS:
      (A) LENGTH: 249 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Met Asp Thr Asp Gly Asp Asn Asp Val Phe Gly Ser Gly Asn Asp Thr
1               5                   10                  15

Arg Asn Asn Asp Asp Lys Lys Lys Glu Glu Met Lys Gln Asn Ile Ser
                20                  25                  30

Asp Asn Ser Gln Ile Ile Ser Thr Arg Asp His Glu Ala Asp Ile Ile
            35                  40                  45
```

```
Gly Ser Ile Ser Lys Glu Asp Leu Ser Lys Ile Val Arg Val Asp
         50                  55                  60

Arg His Asp Ala Leu Ser Ala Asn Asp Val Gln Ser Phe Arg Glu Ala
 65                  70                  75                  80

Met Ile Asn Phe Met Arg Asp Lys Asp Pro Asn Arg Asn Gln Pro Ser
                 85                  90                  95

Asp Lys Leu Ile Ile Ala Met Glu Val Gly Val Tyr Gln Met Val Ile
            100                 105                 110

Asn Leu Gly Thr Ser Ala Lys Leu Gly Asn Ala Asn Asn Leu Gly Phe
            115                 120                 125

Thr Ile Ala Tyr Asp Gln Glu Thr Arg Thr Tyr Lys Val Ala Asp Phe
        130                 135                 140

Val Asn Tyr Met Gln Ser Arg Met Arg Asn Ser Pro Asn Val Val Arg
145                 150                 155                 160

Gln Tyr Ala Arg Ala Met Glu Lys Thr Ile Asn Asn Ile Arg Ser Ala
                165                 170                 175

Gly Ile Ile Asn Ser Asn Gly Val Leu Ala Ala Lys His Gly Val Leu
                180                 185                 190

Ala Ser Tyr Arg Asn Ser Tyr Ser Asp Phe Ala Val Gly Phe Gly Asn
            195                 200                 205

Asp Thr Thr Asp Ala Gln Leu Thr Ser Leu Met Leu Ala Arg Lys Gln
        210                 215                 220

Ala Leu Cys Lys Gly Glu Gly Gly Ser Val Glu His Tyr Asn Thr Met
225                 230                 235                 240

Gln Leu Ala Asn Leu Lys His Pro Cys
                245

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TCAAAATTTA TAGAATTCGC CATGGATACA G                                    31

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AGGTCGGTAC CCCCTAGGTA AACTACAAG                                       29

(2) INFORMATION FOR SEQ ID NO:5:

(i) SEQUENCE CHARACTERISTICS:
        (A) LENGTH: 829 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:5:

```
TCAAAATTTA TATTTTAAGA TATGGATACA GATGGAGATA ATGATGTGTT TGGATCGGGA      60

AACGATACCA GGAATAATGA TGATAAGAAG AAAGAGGAAA TGAAACAAAA CATTTCTGAC     120

AATTCTCAAA TCATATCAAC CAGGGATCAT GAAGCTGACA TCATTGGAAG TATATCGAAA     180

GAGGATTTGT CCAAAATCGT TGTACGCGTC GACAGGCACG ATGCTCTGAG TGCTAATGAT     240

GTTCAAAGTT TTAGAGAAGC TATGATAAAC TTCATGCGAG ACAAAGACCC CAACAGAAAT     300

CAACCTAGTG ACAAATTGAT TATTGCTATG GAAGTTGGAG TTTATCAAAT GGTCATAAAT     360

TTGGGCACTT CGGCTAAATT GGGTAATGCT AACAATTTAG AATTTACGAT AGCTTACGAC     420

CAGGAAACTA GGACATATAA GGTCGCAGAT TTTGTGAATT ATATGCAGTC TAGAATGAGG     480

AACAGTCCAA ATGTTGTTAG GCAATATGCA AGAGCAATGG AAAAGACAAT TAACAACATA     540

AGGAGTGCTG GAATCATAAA CAGCAATGGA GTTTTGGCAG CGAAACATGG TGTGTTGGCA     600

TCTTACAGAA ACTCTTACAG CGACTTTGCT GTTGGTTTTG GTAACGACAC CACTGATGCT     660

CAACTCACTT CGCTAATGTT AGCTAGAAAA CAAGCATTAT GCAAAGGTGA AGGTGGTTCA     720

GTCGAGCATT ACAATACTAT GCAGTTAGCT AACCTTAAAC ATCCATGTTA GAGGCGGAAT     780

GTGATGAAGT AGAACTAACC TCCAGAGATG TCGGAGTTAT TTGATGTTC                 829
```

(2) INFORMATION FOR SEQ ID NO:6:

(i) SEQUENCE CHARACTERISTICS:
        (A) LENGTH: 1665 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
ATGAGAGATT GTAAGGTAGG CTTAGATTTC GGTACTACTT TTAGTACTGT TAGTACTCTT      60

GTGAATAACA GTATGTATGT GTTGAGATTA GGTGATTCGG CTTACATACC AACGTGTATT     120

GCTATCACAC CTGGAGGTGA GGCCATCATA GGAGGTGCTG CAGAAGTACT TCGGGAGAT     180

GATACACCTC ACTGCTTTTT CTATGATTTG AAGAGGTGGG TTGGTGTTGA TGACAATACA     240

TTCAAATTTG CTATGAATAA AATTAGACCC AAATACGTAG CAGAGTTGGT TGAAGGTGAG     300

GTTTATTTAA CCGGCATCAA TAAAGGATTT TCTATAAAGC TGTCTGTTAA GCAATTAATA     360

AAGGCTTATA TAGAAACTAT TGTTAGGTTG TTAGCCAGCT CATATTCTTT GAGAGTCATA     420

GATTTAAATC AGTCTGTTCC GGCCGATTAT AAGAATGCTC AGAGATTAGC TGCAAGATCG     480

GTGTTGAAAG CGTTATCATT TCCTTGTCGT AGGATTATAA ATGAACCATC AGCAGCAGCA     540

GTCTACTGTG TGTCAAGGTA TCCTAATTAT AACTATTTCT TAGTTTATGA TTTTGGAGGA     600

GGTACCTTTG ATGTGTCGCT CATAGGTAAA TATAAGTCTT ATGTCACTGT TATAGATACC     660

GAAGGAGACT CGTTCTTAGG CGGTAGAGAT ATAGACAAGA GTATAGAAGA CTATCTAGTG     720

GGCAAATATA ATATAAAGAA AGTCATTCCA GCTACTTATT TAGCTTTAAT AAAAGAAGAG     780

TGTAATAATA CCAATAAGAG TATTTTTACG ATACTGTTTG ATGACGGATC TGTTCAAGTT     840

GTGGAATTCT CTAAGAGTGA ATTAGAGAAA TGCGTTCGTC CATTTGTCGA AGATCGATC     900

AAACTTATAA ATGATGTGGT GGTACGAAAC AAGTTGACAT CGGGAGTCAT TTATATGGTT     960

GGAGGTTCAT CTCTATTACA ACCAGTACAA GATATGGTGA GGTCTTACGC GTCGACTAAG    1020

GGATTAACCT TAGTTGCAGA TCAAGATATG AGAAGCGCAG TGTCTTACGG TTGTTCGGTT    1080
```

-continued

```
TTGCATAAGT TGGAAGTCAA TAAGGAGATC GTTTATATAG ATTGCAATTC GCATCCGTTA   1140

TCGGACATCT CGTTCAATTG TGATCCAGAA CCCATCATAC GAAAACCGAT GTCAATACCT   1200

TACACTCACA CCGTTAAGAT GCGACATGAC CGTCCTTTAA AAACGATAGT GAATATATAT   1260

GAAGGATCAA ATCTCTTCAT GCCTGAAAAT GATTGGTTGA TATCTTCCAA TATCAATACA   1320

ACAGATTTTG CTAAAGTAGG AGAAGAGTAT AGTAAGGTCT ACGAATATGA TATTGACGGT   1380

ATCATAACCC TAAAAATAAG GAATGAAGTC ACTGGGAAAA TGTTCACATT ACCGAACTCG   1440

TTCACTAAGA GTGATAACAT AAAACCCATC ACTTTTAAAT TAACTCAATT GTCAAACACT   1500

GATGACTTAG CGACGTTGAC GTCTCTCCTA GGTTATCACG ACAAAACTT TGAGAGGTTT    1560

TACGGGTTAT TTAATGTTCC AACAATATTG ATCAAGGAAA TAGACAAATT GGGCGGATTT   1620

AAAACTTTGT ATCGTCGTCT CAAAAGTATG AATGCTAATT TTTAA                   1665
```

(2) INFORMATION FOR SEQ ID NO:7:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Arg Asp Cys Lys Val Gly Leu Asp Phe Gly Thr Thr Phe Ser Thr
1               5                  10                  15

Val Ser Thr Leu Val Asn Asn Ser Met Tyr Val Leu Arg Leu Gly Asp
            20                  25                  30

Ser Ala Tyr Ile Pro Thr Cys Ile Ala Ile Thr Pro Gly Gly Glu Ala
        35                  40                  45

Ile Ile Gly Gly Ala Ala Glu Val Leu Ser Gly Asp Asp Thr Pro His
    50                  55                  60

Cys Phe Phe Tyr Asp Leu Lys Arg Trp Val Gly Val Asp Asp Asn Thr
65                  70                  75                  80

Phe Lys Phe Ala Met Asn Lys Ile Arg Pro Lys Tyr Val Ala Glu Leu
                85                  90                  95

Val Glu Gly Glu Val Tyr Leu Thr Gly Ile Asn Lys Gly Phe Ser Ile
            100                 105                 110

Lys Leu Ser Val Lys Gln Leu Ile Lys Ala Tyr Ile Glu Thr Ile Val
        115                 120                 125

Arg Leu Leu Ala Ser Ser Tyr Ser Leu Arg Val Ile Asp Leu Asn Gln
    130                 135                 140

Ser Val Pro Ala Asp Tyr Lys Asn Ala Gln Arg Leu Ala Ala Arg Ser
145                 150                 155                 160

Val Leu Lys Ala Leu Ser Phe Pro Cys Arg Arg Ile Ile Asn Glu Pro
                165                 170                 175

Ser Ala Ala Ala Val Tyr Cys Val Ser Arg Tyr Pro Asn Tyr Asn Tyr
            180                 185                 190

Phe Leu Val Tyr Asp Phe Gly Gly Thr Phe Asp Val Ser Leu Ile
        195                 200                 205

Gly Lys Tyr Lys Ser Tyr Val Thr Val Ile Asp Thr Glu Gly Asp Ser
    210                 215                 220

Phe Leu Gly Gly Arg Asp Ile Asp Lys Ser Ile Glu Asp Tyr Leu Val
225                 230                 235                 240
```

```
Gly Lys Tyr Asn Ile Lys Lys Val Ile Pro Ala Thr Tyr Leu Ala Leu
                245                 250                 255

Ile Lys Glu Glu Cys Asn Asn Thr Asn Lys Ser Ile Phe Thr Ile Leu
            260                 265                 270

Phe Asp Asp Gly Ser Val Gln Val Val Glu Phe Ser Lys Ser Glu Leu
        275                 280                 285

Glu Lys Cys Val Arg Pro Phe Val Glu Arg Ser Ile Lys Leu Ile Asn
    290                 295                 300

Asp Val Val Arg Asn Lys Leu Thr Ser Gly Val Ile Tyr Met Val
305                 310                 315                 320

Gly Gly Ser Ser Leu Leu Gln Pro Val Gln Asp Met Val Arg Ser Tyr
                325                 330                 335

Ala Ser Thr Lys Gly Leu Thr Leu Val Ala Asp Gln Asp Met Arg Ser
                340                 345                 350

Ala Val Ser Tyr Gly Cys Ser Val Leu His Lys Leu Glu Val Asn Lys
                355                 360                 365

Gly Ile Val Tyr Ile Asp Cys Asn Ser His Pro Leu Ser Asp Ile Ser
            370                 375                 380

Phe Asn Cys Asp Pro Glu Pro Ile Ile Arg Lys Pro Met Ser Ile Pro
385                 390                 395                 400

Tyr Thr His Thr Val Lys Met Arg His Asp Arg Pro Leu Lys Thr Ile
                405                 410                 415

Val Asn Ile Tyr Glu Gly Ser Asn Leu Phe Met Pro Glu Asn Asp Trp
            420                 425                 430

Leu Ile Ser Ser Asn Ile Asn Thr Thr Asp Phe Ala Lys Val Gly Glu
                435                 440                 445

Glu Tyr Ser Lys Val Tyr Glu Tyr Asp Ile Asp Gly Ile Ile Thr Leu
        450                 455                 460

Lys Ile Arg Asn Glu Val Thr Gly Lys Met Phe Thr Leu Pro Asn Ser
465                 470                 475                 480

Phe Thr Lys Ser Asp Asn Ile Lys Pro Ile Thr Phe Lys Leu Thr Gln
                485                 490                 495

Leu Ser Asn Thr Asp Asp Leu Ala Thr Leu Thr Ser Leu Leu Gly Tyr
            500                 505                 510

His Asp Lys Asn Phe Glu Arg Phe Tyr Gly Leu Phe Asn Val Pro Thr
        515                 520                 525

Ile Leu Ile Lys Glu Ile Asp Lys Leu Gly Gly Phe Lys Thr Leu Tyr
    530                 535                 540

Arg Arg Leu Lys Ser Met Asn Ala Asn Phe
545                 550

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GTTTCGAATT CACCATGGGA GATTGTAAGG                                          30

(2) INFORMATION FOR SEQ ID NO:9:

(i) SEQUENCE CHARACTERISTICS:
```

(A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CTGTCTTAAC GACATGGTAC CTAGGTTTGC G                                31

(2) INFORMATION FOR SEQ ID NO:10:

(i) SEQUENCE CHARACTERISTICS:
        (A) LENGTH: 1810 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTTTCAAATT CAAAATGAGA GATTGTAAGG TAGGCTTAGA TTTCGGTACT ACTTTTAGTA        60

CTGTTAGTAC TCTTGTGAAT AACAGTATGT ATGTGTTGAG ATTAGGTGAT TCGGCTTACA       120

TACCAACGTG TATTGCTATC ACACCTGGAG GTGAGGCCAT CATAGGAGGT GCTGCAGAAG       180

TACTTTCGGG AGATGATACA CCTCACTGCT TTTTCTATGA TTTGAAGAGG TGGGTTGGTG       240

TTGATGACAA TACATTCAAA TTTGCTATGA ATAAAATTAG ACCCAAATAC GTAGCAGAGT       300

TGGTTGAAGG TGAGGTTTAT TTAACCGGCA TCAATAAAGG ATTTTCTATA AAGCTGTCTG       360

TTAAGCAATT AATAAAGGCT TATATAGAAA CTATTGTTAG GTTGTTAGCC AGCTCATATT       420

CTTTGAGAGT CATAGATTTA AATCAGTCTG TTCCGGCCGA TTATAAGAAT GCTCAGAGAT       480

TAGCTGCAAG ATCGGTGTTG AAAGCGTTAT CATTTCCTTG TCGTAGGATT ATAAATGAAC       540

CATCAGCAGC AGCAGTCTAC TGTGTGTCAA GGTATCCTAA TTATAACTAT TTCTTAGTTT       600

ATGATTTTGG AGGAGGTACC TTTGATGTGT CGCTCATAGG TAAATATAAG TCTTATGTCA       660

CTGTTATAGA TACCGAAGGA GACTCGTTCT TAGGCGGTAG AGATATAGAC AAGAGTATAG       720

AAGACTATCT AGTGGGCAAA TATAATATAA AGAAAGTCAT TCCAGCTACT TATTTAGCTT       780

TAATAAAAGA AGAGTGTAAT AATACCAATA AGAGTATTTT TACGATACTG TTTGATGACG       840

GATCTGTTCA AGTTGTGGAA TTCTCTAAGA GTGAATTAGA GAAATGCGTT CGTCCATTTG       900

TCGAAAGATC GATCAAACTT ATAAATGATG TGGTGGTACG AAACAAGTTG ACATCGGGAG       960

TCATTTATAT GGTTGGAGGT TCATCTCTAT TACAACCAGT ACAAGATATG GTGAGGTCTT      1020

ACGCGTCGAC TAAGGGATTA ACCTTAGTTG CAGATCAAGA TATGAGAAGC GCAGTGTCTT      1080

ACGGTTGTTC GGTTTTGCAT AAGTTGGAAG TCAATAAGGA GATCGTTTAT ATAGATTGCA      1140

ATTCGCATCC GTTATCGGAC ATCTCGTTCA ATTGTGATCC AGAACCCATC ATACGAAAAC      1200

CGATGTCAAT ACCTTACACT CACACCGTTA AGATGCGACA TGACCGTCCT TTAAAAACGA      1260

TAGTGAATAT ATATGAAGGA TCAAATCTCT TCATGCCTGA AAATGATTGG TTGATATCTT      1320

CCAATATCAA TACAACAGAT TTTGCTAAAG TAGGAGAAGA GTATAGTAAG GTCTACGAAT      1380

ATGATATTGA CGGTATCATA ACCCTAAAAA TAAGGAATGA AGTCACTGGG AAAATGTTCA      1440

CATTACCGAA CTCGTTCACT AAGAGTGATA ACATAAAACC CATCACTTTT AAATTAACTC      1500

AATTGTCAAA CACTGATGAC TTAGCGACGT TGACGTCTCT CCTAGGTTAT CACGACAAAA      1560

ACTTTGAGAG GTTTTACGGG TTATTTAATG TTCCAACAAT ATTGATCAAG GAAATAGACA      1620

AATTGGGCGG ATTTAAAACT TTGTATCGTC GTCTCAAAAG TATGAATGCT AATTTTTAAA      1680

```
GGAGGTTGTT TTCGTTAGAG TCAATTTAAT TTAAAGTGAG AAGATCAGTT AAAAGAAACT    1740

CGACAAACAT AACACCAAAA GTCAGTTAAA ATGTTGAATG ACAGAATTGC TGTAACATGC    1800

TTTCAAACGC                                                          1810
```

(2) INFORMATION FOR SEQ ID NO:11:

(i) SEQUENCE CHARACTERISTICS:
        (A) LENGTH: 1428 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
ATGGACATAA TATCACCAGG GGTGGCCTTT TACAATTATT TACACAGGAC GTTGATTTTT      60

GAATACTCAG ATTACTACTT ACCTCCATGT GAAGATTTGA GAATAACTTT GAGCAAGTCC     120

AAACCATACC ACCCTGGAGC TTATGTTGTC TCGAAAATTC TCGGGAAGGG AGAAAGAAAC     180

AGACCGAACA CTTGGAAACA AGTTATTCAG TCACTATCTC ACAGGAATTT TAATGCGCCA     240

ATTATCAATC ACAAGTTAGA TGTTAAAAGA AGCGCACAAA TACTATATGA CTCGGTGGTG     300

AAATCGTTAA GACAAGACAG GTTGACTGAG TGGTATGAAC CTATTTTACC TGACCTTTTC     360

AAAATCGGTA AGTGGTTGGA TGATAGAGAT GGTAGCAAAT ATCGTATGTT GAACCGTAGA     420

CTAGACTTTG CCAGTTTAGC AGACAAGTTC AAAACTCTCA ACCTCATGGT TAAGGGTGAG     480

ACCAAGCCCA AGATGGATCT TAGCACATAC GACAGTTACA ATGCTCCAGC TAATATAGTC     540

TATTACCAGC AGATAGTCAA TTTGTATTTT TCACCCATGT TTTTAGAGTG TTTCGCAAGG     600

TTGACTTACT GTTTAAGTGA TAAAATCGTT CTATACAGCG GCATGAACAC AGACGTTCTA     660

GCTGAGTTAA TTGAAAGCAA ACTACCATTA GGTCTTAACG CATATCACAC GCTTGAGATA     720

GATTTCAGCA AATTTGATAA GTCTCAAGGC ACATGCTTCA AATTATATGA AGAAATGATG     780

TATAAGATGT TTGGATTTTC TCCTGAGTTG TACGATCGAG ACTTCAAATA CACGGAGTAC     840

TTCTGTAGAG CGAAAGCAAC TTGTGGAGTG GATCTCGAGT TAGGAACACA GCGCAGAACT     900

GGATCTCCAA ACACTTGGTT GTCTAACACT CTAGTTACTT TAGGTATGAT GTTATCATCT     960

TACGACATTG ATGATATAGA CCTACTCCTT GTTAGCGGGG ATGACAGTTT AATTTTTTCC    1020

AGGAAACATC TACCGAATAA AACCCAAGAG ATAAACAAAA ACTTTGGGAT GGAGGCCAAG    1080

TATATAGAGA AATCATCTCC ATACTTCTGC TCCAAATTCA TAGTTGAGTT AAATGGTAAG    1140

TTGAAAGTCA TACCTGATCC AATACGATTC TTTGAAAAAT TGTCAATTCC AATTAGACAA    1200

GAAGATTTCG TAAACGGAAG CGTAGTCAAA GAACGGTTCA TATCATTCAA AGATTTGATG    1260

AAAGAATATG ATAATGATGT CGCCGTTATA CGCATTGACG AAGCAGTGTG TTATAGATAC    1320

AGCATACCGG TTGGCTGTTC CTACGCAGCA TTGTGCTATA TACACTGTTG CATGTCGAAT    1380

TTTGTTTCTT TCCGTAGGAT TTATGACAAT TGTGAAATTG TGTGGATT                 1428
```

(2) INFORMATION FOR SEQ ID NO:12:

(i) SEQUENCE CHARACTERISTICS:
        (A) LENGTH: 476 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:12:

```
Met Asp Ile Ile Ser Pro Gly Val Ala Phe Tyr Asn Tyr Leu His Arg
1               5                   10                  15

Thr Leu Ile Phe Glu Tyr Ser Asp Tyr Tyr Leu Pro Pro Cys Glu Asp
                20                  25                  30

Leu Arg Ile Thr Leu Ser Lys Ser Lys Pro Tyr His Pro Gly Ala Tyr
            35                  40                  45

Val Val Ser Lys Ile Leu Gly Lys Gly Glu Arg Asn Arg Pro Asn Thr
        50                  55                  60

Trp Lys Gln Val Ile Gln Ser Leu Ser His Arg Asn Phe Asn Ala Pro
65                  70                  75                  80

Ile Ile Asn His Lys Leu Asp Val Lys Arg Ser Ala Gln Ile Leu Tyr
                85                  90                  95

Asp Ser Val Lys Ser Leu Arg Gln Asp Arg Leu Thr Glu Trp Tyr
                100                 105                 110

Glu Pro Ile Leu Pro Asp Leu Phe Lys Ile Gly Lys Trp Leu Asp Asp
            115                 120                 125

Arg Asp Gly Ser Lys Tyr Arg Met Leu Asn Arg Leu Asp Phe Ala
        130                 135                 140

Ser Leu Ala Asp Lys Phe Lys Thr Leu Asn Leu Met Val Lys Gly Glu
145                 150                 155                 160

Thr Lys Pro Lys Met Asp Leu Ser Thr Tyr Asp Ser Tyr Asn Ala Pro
                165                 170                 175

Ala Asn Ile Val Tyr Tyr Gln Gln Ile Val Asn Leu Tyr Phe Ser Pro
                180                 185                 190

Met Phe Leu Glu Cys Phe Ala Arg Leu Thr Tyr Cys Leu Ser Asp Lys
            195                 200                 205

Ile Val Leu Tyr Ser Gly Met Asn Thr Asp Val Glu Ala Glu Leu Ile
210                 215                 220

Glu Ser Lys Leu Pro Leu Gly Leu Asn Ala Tyr His Thr Leu Glu Ile
225                 230                 235                 240

Asp Phe Ser Lys Phe Asp Lys Ser Gln Gly Thr Cys Phe Lys Leu Tyr
                245                 250                 255

Glu Glu Met Met Tyr Lys Met Phe Gly Phe Ser Pro Glu Leu Tyr Asp
            260                 265                 270

Arg Asp Phe Lys Tyr Thr Glu Tyr Phe Cys Arg Ala Lys Ala Thr Cys
        275                 280                 285

Gly Val Asp Leu Glu Leu Gly Thr Gln Arg Arg Thr Gly Ser Pro Asn
        290                 295                 300

Thr Trp Leu Ser Asn Thr Leu Val Thr Leu Gly Met Met Leu Ser Ser
305                 310                 315                 320

Tyr Asp Ile Asp Asp Ile Asp Leu Leu Val Ser Gly Asp Ser
                325                 330                 335

Leu Ile Phe Ser Arg Lys His Leu Pro Asn Lys Thr Gln Glu Ile Asn
            340                 345                 350

Lys Asn Phe Gly Met Glu Ala Lys Tyr Ile Glu Lys Ser Ser Pro Tyr
        355                 360                 365

Phe Cys Ser Lys Phe Ile Val Glu Leu Asn Gly Lys Leu Lys Val Ile
    370                 375                 380

Pro Asp Pro Ile Arg Phe Phe Glu Lys Leu Ser Ile Pro Ile Arg Gln
385                 390                 395                 400

Glu Asp Phe Val Asn Gly Ser Val Val Lys Glu Arg Phe Ile Ser Phe
                405                 410                 415
```

```
Lys Asp Leu Met Lys Glu Tyr Asp Asn Asp Val Ala Val Ile Arg Ile
            420                 425                 430

Asp Glu Ala Val Cys Tyr Arg Tyr Ser Ile Pro Val Gly Cys Ser Tyr
        435                 440                 445

Ala Ala Leu Cys Tyr Ile His Cys Cys Met Ser Asn Phe Val Ser Phe
    450                 455                 460

Arg Arg Ile Tyr Asp Asn Cys Glu Ile Val Trp Ile
465                 470                 475

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TATGAGAGCA TAGAATTCCC CATGGACATA                               30

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CTGTTAAGGT ACCTTAAGAA CTAGTC                                   26

(2) INFORMATION FOR SEQ ID NO:15:

(i) SEQUENCE CHARACTERISTICS:
        (A) LENGTH: 1515 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TATGAGAGCA TAATAGACCT GATGGACATA ATATCACCAG GGGTGGCCTT TTACAATTAT    60

TTACACAGGA CGTTGATTTT TGAATACTCA GATTACTACT TACCTCCATG TGAAGATTTG   120

AGAATAACTT TGAGCAAGTC CAAACCATAC CACCCTGGAG CTTATGTTGT CTCGAAAATT   180

CTCGGGAAGG GAGAAAGAAA CAGACCGAAC ACTTGGAAAC AAGTTATTCA GTCACTATCT   240

CACAGGAATT TTAATGCGCC AATTATCAAT CACAAGTTAG ATGTTAAAAG AAGCGCACAA   300

ATACTATATG ACTCGGTGGT GAAATCGTTA AGACAAGACA GGTTGACTGA GTGGTATGAA   360

CCTATTTTAC CTGACCTTTT CAAAATCGGT AAGTGGTTGG ATGATAGAGA TGGTAGCAAA   420

TATCGTATGT TGAACCGTAG ACTAGACTTT GCCAGTTTAG CAGACAAGTT CAAAACTCTC   480

AACCTCATGG TTAAGGGTGA GACCAAGCCC AAGATGGATC TTAGCACATA CGACAGTTAC   540

AATGCTCCAG CTAATATAGT CTATTACCAG CAGATAGTCA ATTTGTATTT TTCACCCATG   600

TTTTTAGAGT GTTTCGCAAG GTTGACTTAC TGTTTAAGTG ATAAAATCGT TCTATACAGC   660

GGCATGAACA CAGACGTTCT AGCTGAGTTA ATTGAAAGCA AACTACCATT AGGTCTTAAC   720
```

```
GCATATCACA CGCTTGAGAT AGATTTCAGC AAATTTGATA AGTCTCAAGG CACATGCTTC       780

AAATTATATG AAGAAATGAT GTATAAGATG TTTGGATTTT CTCCTGAGTT GTACGATCGA       840

GACTTCAAAT ACACGGAGTA CTTCTGTAGA GCGAAAGCAA CTTGTGGAGT GGATCTCGAG       900

TTAGGAACAC AGCGCAGAAC TGGATCTCCA AACACTTGGT TGTCTAACAC TCTAGTTACT       960

TTAGGTATGA TGTTATCATC TTACGACATT GATGATATAG ACCTACTCCT TGTTAGCGGG      1020

GATGACAGTT TAATTTTTC CAGGAAACAT CTACCGAATA AAACCCAAGA GATAAACAAA       1080

AACTTTGGGA TGGAGGCCAA GTATATAGAG AAATCATCTC CATACTTCTG CTCCAAATTC      1140

ATAGTTGAGT TAAATGGTAA GTTGAAAGTC ATACCTGATC CAATACGATT CTTTGAAAAA      1200

TTGTCAATTC CAATTAGACA AGAAGATTTC GTAAACGGAA GCGTAGTCAA AGAACGGTTC      1260

ATATCATTCA AAGATTTGAT GAAAGAATAT GATAATGATG TCGCCGTTAT ACGCATTGAC      1320

GAAGCAGTGT GTTATAGATA CAGCATACCG GTTGGCTGTT CCTACGCAGC ATTGTGCTAT      1380

ATACACTGTT GCATGTCGAA TTTTGTTTCT TTCCGTAGGA TTTATGACAA TTGTGAAATT      1440

GTGTGGATTT AAGATGGACA CTTCAAGTTT TATCGCCTCG ATTGAAAAAG ACAATTTGAT      1500

GGATTGCTTG ATCAG                                                      1515

(2) INFORMATION FOR SEQ ID NO:16:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

ATGATAATGA TGTCGCCGTT ATACGCATTG ACGAAGCAGT GTGTTATAGA TACAGCATAC        60

CGGTTGGCTG TTCCTACGCA GCATTGTGCT ATATACACTG TTGCATGTCG AATTTTGTTT       120

CTTTCCGTAG GATTTATGAC AATTGTGAAA TTGTGTGGAT TTAAGATGGA CACTTCAAGT       180

TTTATCGCCT CGATTGAAAA AGACAATTTG ATGGATTGCT TGATCAGTTT AGTTGAGATG       240

AGAGATCGTC TTAGGTTGTG CAACGATTTC CCAATATTGA ATTATGGAGT TAACATTTTA       300

GAATTACTAA TAGGCAAAAG GTTGAATAAA ATTAATAATT TAAAGAATTG TTATGTAATT       360

AGAGAACTAA TAACAATAAA TATAAGTAAG GAGTGGGTTG AAAGCAAGC TCTAAAAGTT       420

GGCTTACATT GCTTCTTAAA TCTATCTCAA GCCGAAAGCA GACATGTCAA GTATCTTTTG       480

AGCGACAAAG AGTCCTTAAA TAAGATGAAC TTCTCTAGAT ACTATGTCCC CAAAGTGGTA       540

ACAGATTTGT ATTTAGATTT GATTGGGGTG TTATACGTGA ATACAGGATA CAACATAGAT       600

TTAGTAGAAA AATTTATTTT CGATAAATTA GAATTTCTAG TTTATGATGG AGAGGAGGGT       660

TTCAAAAGTC CACAGGTTGA ATACAATGAC ATATGTACGG TCTACAATTT GAAACCAATA       720

ATAAAATACA ATCGTTGGCA CACAGATGGT TCTATAGTTA TAGAGTGTGG TGACGTAATA       780

GGAAAAGGTA TTAATAAAAC AAAGAAAAAA ATTTGCAATA AA                         822

(2) INFORMATION FOR SEQ ID NO:17:

(i) SEQUENCE CHARACTERISTICS:
        (A) LENGTH: 274 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:17:

Met Ile Met Met Ser Pro Leu Tyr Ala Leu Thr Lys Gln Cys Val Ile
1               5                   10                  15

Asp Thr Ala Tyr Arg Leu Ala Val Pro Thr Gln His Cys Ala Ile Tyr
            20                  25                  30

Thr Val Ala Cys Arg Ile Leu Phe Leu Ser Val Gly Phe Met Thr Ile
        35                  40                  45

Val Lys Leu Cys Gly Phe Lys Met Asp Thr Ser Ser Phe Ile Ala Ser
    50                  55                  60

Ile Glu Lys Asp Asn Leu Met Asp Cys Leu Ile Ser Leu Val Glu Met
65                  70                  75                  80

Arg Asp Arg Leu Arg Leu Cys Asn Asp Phe Pro Ile Leu Asn Tyr Gly
                85                  90                  95

Val Asn Ile Leu Glu Leu Leu Ile Gly Lys Arg Leu Asn Lys Ile Asn
            100                 105                 110

Asn Leu Lys Asn Cys Tyr Val Ile Arg Glu Leu Ile Thr Ile Asn Ile
        115                 120                 125

Ser Lys Glu Trp Val Gly Lys Gln Ala Leu Lys Val Gly Leu His Cys
    130                 135                 140

Phe Leu Asn Leu Ser Gln Ala Glu Ser Arg His Val Lys Tyr Leu Leu
145                 150                 155                 160

Ser Asp Lys Glu Ser Leu Asn Lys Met Asn Phe Ser Arg Tyr Tyr Val
                165                 170                 175

Pro Lys Val Val Thr Asp Leu Tyr Leu Asp Leu Ile Gly Val Leu Tyr
            180                 185                 190

Val Asn Thr Gly Tyr Asn Ile Asp Leu Val Glu Lys Phe Ile Phe Asp
        195                 200                 205

Lys Leu Glu Phe Leu Val Tyr Asp Gly Glu Gly Phe Lys Ser Pro
210                 215                 220

Glu Val Glu Tyr Asn Asp Ile Cys Thr Val Tyr Asn Leu Lys Pro Ile
225                 230                 235                 240

Ile Lys Tyr Asn Arg Trp His Thr Asp Gly Ser Ile Val Ile Glu Cys
                245                 250                 255

Gly Asp Val Ile Gly Lys Gly Ile Asn Lys Thr Lys Lys Lys Ile Cys
            260                 265                 270

Asn Lys (2) INFORMATION FOR SEQ ID NO:18:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:18:

GATGGAATTC CATGGTAATG ATGTCGCCG                                              29

(2) INFORMATION FOR SEQ ID NO:19:

(i) SEQUENCE CHARACTERISTICS:
             (A) LENGTH: 25 base pairs
             (B) TYPE: nucleic acid
             (C) STRANDEDNESS: single (D) TOPOLOGY: linear (ii) MOLECULE TYPE: cDNA (xi) SEQUENCE DESCRIPTION: SEQ ID NO:19:

CCCACAAAGG TACCACCTAG GGGGG                                        25

(2) INFORMATION FOR SEQ ID NO:20:

(i) SEQUENCE CHARACTERISTICS:
        (A) LENGTH: 932 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GATGAAAGAA TATGATAATG ATGTCGCCGT TATACGCATT GACGAAGCAG TGTGTTATAG    60

ATACAGCATA CCGGTTGGCT GTTCCTACGC AGCATTGTGC TATATACACT GTTGCATGTC   120

GAATTTTGTT TCTTTCCGTA GGATTTATGA CAATTGTGAA ATTGTGTGGA TTTAAGATGG   180

ACACTTCAAG TTTTATCGCC TCGATTGAAA AAGACAATTT GATGGATTGC TTGATCAGTT   240

TAGTTGAGAT GAGAGATCGT CTTAGGTTGT GCAACGATTT CCCAATATTG AATTATGGAG   300

TTAACATTTT AGAATTACTA ATAGGCAAAA GGTTGAATAA AATTAATAAT TTAAAGAATT   360

GTTATGTAAT TAGAGAACTA ATAACAATAA ATATAAGTAA GGAGTGGGTT GGAAAGCAAG   420

CTCTAAAAGT TGGCTTACAT TGCTTCTTAA ATCTATCTCA AGCCGAAAGC AGACATGTCA   480

AGTATCTTTT GAGCGACAAA GAGTCCTTAA ATAAGATGAA CTTCTCTAGA TACTATGTCC   540

CCAAAGTGGT AACAGATTTG TATTTAGATT TGATTGGGGT GTTATACGTG AATACAGGAT   600

ACAACATAGA TTTAGTAGAA AAATTTATTT TCGATAAATT AGAATTTCTA GTTTATGATG   660

GAGAGGAGGG TTTCAAAAGT CCACAGGTTG AATACAATGA CATATGTACG GTCTACAATT   720

TGAAACCAAT AATAAAATAC AATCGTTGGC ACACAGATGG TTCTATAGTT ATAGAGTGTG   780

GTGACGTAAT AGGAAAAGGT ATTAATAAAA CAAAGAAAAA AATTTGCAAT AAATGATGCC   840

AAAGCGGAGT TCGTAAAGAA CTTCAAAGCA AAAATAAAA ATAACGAATA GGGTGTTTTG   900

ATAGTAGTTC CCCCCGCTAA ACCTTCCTAA GA                                932

(2) INFORMATION FOR SEQ ID NO:21:

(i) SEQUENCE CHARACTERISTICS:
        (A) LENGTH: 1359 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

ATGTTAGAGG CGGAATGTGA TGAAGTAGAA CTAACCTCCA GAGATGTCGG AGATTATTTG    60

ATGTTCAAAA CGAGAATAAC CGATAATTTC ACTGGAGATT TAACCTTGAA TATAAACACC   120

TCGAACTTAA TCAAATTCAA AACTTGTAGT TTCTTTATAT GTTATGGAGA CGACAAGGAT   180

AGGTATGAAT TGGGTTGGAC TTCAACATCT ACATCTAGAA GTATTTTTCA ACATTATAAG   240

GATGGTAAAT ACATTCGAGA TTTTAGAATA CAAGATCCAT TTCCAATTCT ATCAGGTTCA   300

ACATTTCCAG TAGTGATTTC TAAAATAATA GCGAATAGAG TTGCCTTTCG TATGAGTAGA   360

AGATTAAATA ATGTTATTGT TGATAAGCTT AAGAATAACA TTATAGAGTT CTATTTGTA    420

```
GTATATTTAG ATGTGGATAC TGGGAAGATT AAACCAAACA CAATACTCAA AAATTTAGAT      480

TTGTCCAGTC TTTTTATCGT TTTCAGTAAC AACGGAAACA ATAAAATCAA TCTACCATAT      540

GAGATAGAGC TACAGACTAA AGATAGAGGC ATTGTTTACA CAAAAATGGG TAATCCTATA      600

TCTTACAACC TCTTCAATAA GTTTGAAGAT TTATTAGACA TAGAAACCAA AGGTGTCGAT      660

AAACCCGAAG ACAAACCCAA ACCTGTGTTT GACGACAAAG GCAAGCAACC CACGGATACG      720

GTTCCTCCTG TTGACAATGG CAAGCCCGAC ATAAGCAAAC CTGGTGAGAA ACAGGGAGAC      780

ATAGATATTG CTAGCAAGTT TAATAATATA GTCATGGCAA AATTGAAAGC TCAATCTTCA      840

TCAGATCCAT TGACGAAAAA GCAATGTGAT CAATTGATGT TGAGTCTAAT CAAATGGTTT      900

GAAAAATTTG GAATCACAAA AGACAATGCC CGATTGCTGA TATTTCAATT TGGTATATCT      960

TTTTCGACTT CAAAAGAAAA TCTTAACAAT ATCACTAACA ATATTGTTGT AGAGAATGAC     1020

AAAGGTGGGT TTGTAAAAAT TTTAAAAATA GATTACTTGA ACAAACTGTA CGGTTCGATT     1080

CCTGAGTCGC ATACTCACAA TTTAGAAAGA GTTCTACTAA GACATTATGC TCAAGAAATC     1140

TTAATATTAC TAAGAAGCAA AGTGTTAGAA TGGCCTAGGA AATTAGCAAG AAATAAGGGC     1200

ATTTTCGAAC AATATGCCTA CATGGCCTGT GACTTTTTCG ACACCGCAGA ATTAGAATTG     1260

ACGGAGGCTG AGACCACAGC TTTGACGACG GTAAAGTCTT GGACTATGAA CCATTATAAG     1320

AAGAAAAGAC AGATAGTTAA TAGTTCACAA TTAGAATGA                            1359
```

(2) INFORMATION FOR SEQ ID NO:22:

(i) SEQUENCE CHARACTERISTICS:
        (A) LENGTH: 452 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Met Leu Glu Ala Glu Cys Asp Glu Val Glu Leu Thr Ser Arg Asp Val
1               5                  10                  15

Gly Asp Tyr Leu Met Phe Lys Thr Arg Ile Thr Asp Asn Phe Thr Gly
            20                  25                  30

Asp Leu Thr Leu Asn Ile Asn Thr Ser Asn Leu Ile Lys Phe Lys Thr
        35                  40                  45

Cys Ser Phe Phe Ile Cys Tyr Gly Asp Asp Lys Asp Arg Tyr Glu Leu
    50                  55                  60

Gly Trp Thr Ser Thr Ser Thr Ser Arg Ser Ile Phe Gln His Tyr Lys
65                  70                  75                  80

Asp Gly Lys Tyr Ile Arg Asp Phe Arg Ile Gln Asp Pro Phe Pro Ile
                85                  90                  95

Leu Ser Gly Ser Thr Phe Pro Val Val Ile Ser Lys Ile Ile Ala Asn
            100                 105                 110

Arg Val Ala Phe Arg Met Ser Arg Arg Leu Asn Asn Val Ile Val Asp
        115                 120                 125

Lys Leu Lys Asn Asn Ile Ile Glu Phe Leu Phe Val Val Tyr Leu Asp
    130                 135                 140

Val Asp Thr Gly Lys Ile Lys Pro Asn Thr Ile Leu Lys Asn Leu Asp
145                 150                 155                 160

Leu Ser Ser Leu Phe Ile Val Phe Ser Asn Asn Gly Asn Asn Lys Ile
                165                 170                 175
```

```
Asn Leu Pro Tyr Glu Ile Glu Leu Gln Thr Lys Asp Arg Gly Ile Val
            180                 185                 190

Tyr Thr Lys Met Gly Asn Pro Ile Ser Tyr Asn Leu Phe Asn Lys Phe
        195                 200                 205

Glu Asp Leu Leu Asp Ile Glu Thr Lys Gly Val Asp Lys Pro Glu Asp
        210                 215                 220

Lys Pro Lys Pro Val Phe Asp Asp Lys Gly Lys Gln Pro Thr Asp Thr
225                 230                 235                 240

Val Pro Pro Val Asp Asn Gly Lys Pro Asp Ile Ser Lys Pro Gly Glu
                245                 250                 255

Lys Gln Gly Asp Ile Asp Ile Ala Ser Lys Phe Asn Asn Ile Val Met
            260                 265                 270

Ala Lys Leu Lys Ala Gln Ser Ser Ser Asp Pro Leu Thr Lys Lys Gln
        275                 280                 285

Cys Asp Gln Leu Met Leu Ser Leu Ile Lys Trp Phe Glu Lys Phe Gly
        290                 295                 300

Ile Thr Lys Asp Asn Ala Arg Leu Leu Ile Phe Gln Phe Gly Ile Ser
305                 310                 315                 320

Phe Ser Thr Ser Lys Glu Asn Leu Asn Asn Ile Thr Asn Asn Ile Val
                325                 330                 335

Val Glu Asn Asp Lys Gly Gly Phe Val Lys Ile Leu Lys Ile Asp Tyr
            340                 345                 350

Leu Asn Lys Leu Tyr Gly Ser Ile Pro Glu Ser His Thr His Asn Leu
        355                 360                 365

Glu Arg Val Leu Leu Arg His Tyr Ala Gln Glu Ile Leu Ile Leu Leu
        370                 375                 380

Arg Ser Lys Val Leu Glu Trp Pro Arg Lys Leu Ala Arg Asn Lys Gly
385                 390                 395                 400

Ile Phe Glu Gln Tyr Ala Tyr Met Ala Cys Asp Phe Phe Asp Thr Ala
                405                 410                 415

Glu Leu Glu Leu Thr Glu Ala Glu Thr Thr Ala Leu Thr Thr Val Lys
            420                 425                 430

Ser Trp Thr Met Asn His Tyr Lys Lys Arg Gln Ile Val Asn Ser
        435                 440                 445

Ser Gln Leu Glu
    450

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CGGAATTCCA TGGTCAAAAC GAG                                    23

(2) INFORMATION FOR SEQ ID NO:24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA
```

-continued (xi) SEQUENCE DESCRIPTION: SEQ ID NO:24:

CGGGCTGTAT TCGTTTGGTA CCCTCTTTGT CCCTAGGTAT CT          42

(2) INFORMATION FOR SEQ ID NO:25:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

ATGTTCAAAA CGAGAATAAC CGATAATTTC ACTGGAGATT TAACCTTGAA TATAAACACC          60

TCGAACTTAA TCAAATTCAA AACTTGTAGT TTCTTTATAT GTTATGGAGA CGACAAGGAT         120

AGGTATGAAT TGGGTTGGAC TTCAACATCT ACATCTAGAA GTATTTTTCA ACATTATAAG         180

GATGGTAAAT ACATTCGAGA TTTTAGAATA CAAGATCCAT TTCCAATTCT ATCAGGTTCA         240

ACATTTCCAG TAGTGATTTC TAAAATAATA GCGAATAGAG TTGCCTTTCG TATGAGTAGA         300

AGATTAAATA ATGTTATTGT TGATAAGCTT AAGAATAACA TTATAGAGTT TCTATTTGTA         360

GTATATTTAG ATGTGGATAC TGGGAAGATT AAACCAAACA CAATACTCAA AAATTTAGAT         420

TTGTCCAGTC TTTTTATCGT TTTCAGTAAC AACGGAAACA ATAAAATCAA TCTACCATAT         480

GAGATAGAGC TACAGACTAA AGATAGAGGC ATTGTTTACA CAAAAATGGG TAATCCTATA         540

TCTTACAACC TCTTCAATAA GTTTGAAGAT TTATTAGACA TAGAAACCAA AGGTGTCGAT         600

AAACCCGAAG ACAAACCCAA ACCTGTGTTT GACGACAAAG GCAAGCAACC CACGGATACG         660

GTTCCTCCTG TTGACAATGG CAAGCCCGAC ATAAGCAAAC CTGGTGA                       707

LETTUCE INFECTIOUS YELLOWS VIRUS GENES

RELATED APPLICATIONS

This application is a national stage of PCT/US94/06430 filed Jun. 13, 1994, which is a continuation of Ser. No. 08/090,532 filed Jul. 9, 1993, now abandoned; and Ser. No. 08/138,138, filed Oct. 15, 1993, now abandoned; and Ser. No. 08/146,780, filed Nov. 1, 1993, now abandoned.

FIELD OF THE INVENTION

This invention relates to genes of the lettuce infectious yellows virus (LIYV) and, more specifically, to their incorporation into transfer vectors, and to the use of at least one of these genes to produce transformed plant cells and transformed plants which are resistant to LIYV infections.

BACKGROUND OF THE INVENTION

Lettuce infectious yellows virus (LIYV) was first identified by Duffus et al., 1982, when it occurred in epidemic proportions in the desert Southwest of the United States. Large losses occurred in lettuce, sugarbeets, cantaloupe, watermelon, other melons, and squash due to stunting of infected plants and leaf rolling, yellowing, and brittleness. It has also been reported that LIYV infects cucumbers in Europe.

LIYV virus particles are flexuous and filamentous measuring approximately 1800–2000 nm in length. The LIYV genome is single-stranded RNA and includes about 15,700 nucleotides in positive (+, coding, or sense) polarity. Preliminary characterization of the RNA genome reveals that there may be two RNAs present in LIYV-infected plants and purified LIYV virions (Klaassen et al., 1992).

It has been shown for several viruses [tobacco mosaic virus (Powell-Abel et al., 1986), alfalfa mosaic virus (Tumer et al., 1987), cucumber mosaic virus (Cuozzo et al., 1988; Quemada et al., 1991), and potato virus X (Hemenway et al., 1988)] that expression of the coat protein gene in transgenic plants results in a plant which is resistant to infection by the respective virus. It has also been shown for tobacco vein mottle virus (TVMV) that expression of the protease gene (NIa) confers resistance to TVMV (Maiti et al., 1993). It has not been determined, however, whether this method for engineering resistance to infection will extend to different kinds of viruses such as LIYV. In addition, it has not been determined whether the expression of other viral proteins, such as the heat shock protein-70, in transgenic plants results in a plant which is resistant to infection by the respective virus.

The LIYV genes isolated from viral RNA do not contain the regulatory sequences needed for gene expression. For example, the LIYV coat protein gene does not contain the signals necessary for its expression once transferred and integrated into a plant genome. Therefore, the coat protein gene, like the RNA polymerase gene, the heat shock protein-70 gene, ORF 3 of LIYV RNA1 and ORF 6 of LIYV RNA2, must be engineered to contain a plant expressible promoter 5' to a translation initiation codon (ATG) and a plant functional poly(A) addition signal (AATAAA) 3' of a translation termination signal.

In a first embodiment of the present invention, the nucleotide sequence of the coat protein gene for LIYV, along with its putative amino acid sequence, has been determined. The gene has been inserted into expression vectors to supply it with the necessary genetic regulatory sequences so that the genes can be expressed when incorporated into a plant genome. Plant cells are transformed with the vector construct and the plant cells are induced to regenerate sexually mature plants. The resulting plants contain the coat protein gene and possess an increased resistance to infection by the virus from which the coat protein gene is derived.

In a second embodiment of the present invention, the nucleotide sequence of the heat shock protein-70 gene for LIYV, along with its putative amino acid sequence, has been determined. The gene has been inserted into expression vectors to supply it with the necessary genetic regulatory sequences so that the genes can be expressed when incorporated into a plant genome. Plant cells are transformed with the vector construct and the plant cells are induced to regenerate sexually mature plants. The resulting plants contain the heat shock protein-70 gene and possess an increased resistance to infection by the virus from which the heat shock protein-70 gene is derived.

In a third embodiment of the present invention, the nucleotide sequence of the RNA polymerase gene for LIYV, along with its putative amino acid sequence, has been determined. The gene has been inserted into expression vectors to supply it with the necessary genetic regulatory sequences so that the genes can be expressed when incorporated into a plant genome. Plant cells are transformed with the vector construct and the plant cells are induced to regenerate sexually mature plants. The resulting plants contain the RNA polymerase gene and possess an increased resistance to infection by the virus from which the RNA polymerase gene is derived.

In a fourth embodiment of the present invention, the nucleotide sequence of ORF 6 of LIYV RNA2, along with its putative amino acid sequence, has been determined. The gene has been inserted into expression vectors to supply it with the necessary genetic regulatory sequences so that the genes can be expressed when incorporated into a plant genome. Plant cells are transformed with the vector construct and the plant cells are induced to regenerate sexually mature plants. The resulting plants contain the LIYV RNA2 ORF 6 gene and possess an increased resistance to infection by the virus from which the LIYV RNA2 ORF 6 gene is derived.

In a fifth embodiment of the present invention, the nucleotide sequence of ORF 3 of LIYV RNA1, along with its putative amino acid sequence, has been determined. The gene has been inserted into expression vectors to supply it with the necessary genetic regulatory sequences so that the genes can be expressed when incorporated into a plant genome. Plant cells are transformed with the vector construct and the plant cells are induced to regenerate sexually mature plants. The resulting plants contain the LIYV RNA1 ORF 3 gene and possess an increased resistance to infection by the virus from which the LIYV RNA1 ORF 3 gene is derived.

INFORMATION DISCLOSURE

U.S. Pat. No. 4,774,182 to Szybalski discloses conferring immunity on a biological host by the insertion of partially defective foreign gene into the host.

U.S. Pat. No. 4,940,838 to Schilperoot et al. relates to a process for the incorporation of foreign DNA into the genome of dicotyledonous plants.

U.S. Pat. No. 4,970,168 to Tumer relates to transgenic plants which are resistant to virus infection by PVY and PVX.

European patent application 0 223 452, published Nov. 29, 1986, reports the production of plants resistant to viral infection by using a recombinant DNA molecule to give genetically transformed plants.

European patent application 0 426 195 reports recombinant DNA constructs containing a DNA sequence coding for a tospovirus protein. The DNA constructs can be introduced into plants to reduce their susceptibility to diseases induced by tospovirus e.g. tomato spotted wilt virus (TSWV).

European Patent Application 0 536 106, filed 2 Oct. 1992, entitled Plants resistant to infection by PVX, reports that the DNA sequence encoding potato virus X replicase can be used to transform potato and tomato plants to confer viral resistance.

Australian Patent Application No. 71951/91, filed 28 Feb. 1991, entitled Process for production of exogenous gene or its product in plant cells, reports the use of RNA replicase in a transgenic situation.

PCT Patent Publication WO89/05858, dated 29 Jun. 1989, entitled Cucumber Mosaic Virus Coat Protein Gene, discloses the coat protein gene from the C strain of cucumber mosaic virus and discloses the use of this gene to prepare plant transformation vectors and virus-resistant plants.

PCT Patent Publication WO89/05859, filed 29 Jun. 1989, entitled Agrobacterium Mediated Transformation of Germinating Plant, discloses the production of transgenic plants by incubating germinating seeds prior to differentiation with an Agrobacterium strain containing a transferable gene.

PCT Patent Publication WO90/02184, dated 8 Mar. 1990, entitled Potyvirus Coat protein Genes and Plants Transformed Therewith, discloses the potyvirus coat protein genes and discloses the use of these genes to produce transformed plants resistant to viral infection by potyvirus and related viruses.

PCT Patent Publication WO90/02185, dated 8 Mar. 1990, entitled Cucumber Mosaic Virus Coat Protein Gene discloses a recombinant DNA molecule containing the nucleotide sequence of the coat protein gene from the WL strain of cucumber mosaic virus (CMV). Plants transformed with the DNA molecule are resistant to CMV viral infection, esp. members of the curcurbitanceae (e.g. squash, cucumber) and solanaceae (e.g. peppers, tomatoes) families.

PCT Patent Publication WO/90/02189, dated 8 Mar. 1990, entitled Expression Cassette for Plants.

PCT Patent Publication WO92/03539, filed 22 Aug. 1991, entitled Virus Resistance in Plants, reports a recombinant plant genome having virus resistance and comprising a gene expressing a product which inhibits expression of or inhibits the catalytic activity of viral RNA-dependent RNA polymerase.

PCT Patent Publication WO 91/13542, entitled Transformation of Plants with Non-Structural Plant Virus Genes.

Agranovsky, A. A., Boyko, V. P., Karasev, A. V., Koonin, E. V. & Dolja, V. V. (1991). Putative 65 kDa Protein of Beet Yellows Closterovirus Is a Homologue of HSP70 Heat Shock Proteins. *J. Mol. Biol.* 217:603–610. By computer analysis, the authors compare beet yellows virus HSP-70 with other HSP-70 sequences in the literature. They reported that eight amino acid sequences are highly conserved in heat shock 70 proteins, including beet yellows virus heat shock protein.

Agranovsky, A. A., Boyko, V. P., Karasev, A. V., Lunina, N. A., Koonin, E. V. & Dolja, V. V. (1991). Nucleotide sequence of the 3'-terminal hair of beet yellows closterovirus RNA genome: unique arrangement of eight virus genes. *Journal of General Virology* 72: 15–23. The authors report that the sequence of 6746 bases of the 3' end of beet yellows virus has been determined. Eight open reading frames were identified, including RNA polymerase, heat shock protein and coat protein.

Amasino, R. M. (1986). Acceleration of nucleic acid hybridization rate by polyethylene glycol. *Analytical Biochemistry* 152: 304–307.

Anderson J. M., P. Palukaitis, and M. Zaitlin. 1992. A defective replicase gene induces resistance to cucumber mosaic virus in transgenic tobacco plants. *P.N.A.S. USA* 89:8759–8763. The replicase gene of cucumber mosaic virus encoded by RNA2 was modified by deleting a 94-base-pair region. Plants transgenic for this modified gene were resistant to virus disease when challenged with CMV virions or RNA.

Baltimore, D. (1966). Purification and properties of poliovirus double-stranded ribonucleic acid. *Journal of Molecular Biology* 18: 421–428.

Beachy, R. N., Loesch-Fries, S., and Turner, N. E. (1990). Coat protein mediated resistance against virus infection. *Annu. Rev. Phytopathol.,* 28:451–474. A thorough review of the literature regarding the observations and rationale surrounding engineered coat protein mediated resistance.

Bejarano E. R. and C. P. Lichtenstein. 1992. Prospects for engineering virus resistance in plants with antisense RNA. *TIBTECH* 10:383–388.

Bimboim, H. C. & Doly, J. (1979). A rapid alkaline extraction procedure for screening recombinant plasmid DNA. *Nucleic Acids Research* 7: 1513–1523.

Boyko, V. P., Karasev, A. V., Agranovsky, A. A., Koonin, E. V. & Dolja, V. V. (1992). Coat protein gene duplication in a filamentous RNA virus of plants. Proceedings of the *National Academy of Sciences U.S.A.* 89: 9156–9160.

Boyko, V. P., Karasev, A. V., Agranovsky, A. A., Koonin, E. V. and Dolja, V. V. (1992). Coat protein gene duplication in a filamentous RNA virus of plants. PNAS (USA) 89:9156–9160. The authors present evidence that amino acid sequence homologies between beet yellows virus coat protein and a beet yellows virus open reading share significant homology.

Braun, C. J. and C. L. Hemenway. 1992. Expression of Amino-Terminal Portions or Full-Length Viral Replicase Genes in Transgenic Plants Confers Resistance to Potato Virus X Infection. *The Plant Cell* 4:735–744. ORF 1 of potato virus X was transformed and expressed in tobacco. Transgenic lines are resistant to PVX infection when inoculated with either PVX or PVY RNA.

Brunstedt, J. and Hall, R. (1991). Nucleotide Sequence of Beet Yellows Virus and Expression of the Coat Protein Gene in *E. Coli* and in Plants. *Program & Abstracts,* International Soc. for Plant Molecular Biology, Third International Congress, Tucson, Ariz., Oct. 6–11, 1991. This abstract reports the cloning, sequencing, engineering and production of plants transgenic for the Beet Yellows Virus coat protein gene.

Bruen, J. A. (1991). Relationships among the positive strand and double-strand RNA viruses as viewed through their RNA-dependent RNA polymerases. *Nuc Acids Res* 19:217–226.

Burnette, W. N. (1981). "Western blotting": electrophoretic transfer of proteins from sodium dodecyl sulfate polyacrylamide gels to unmodified nitrocellulose and radiographic detection with antibody and radioiodinated Protein A. *Analytical Biochemistry* 112: 195–203.

Carr, J. P., L. E. Marsh, G. P. Lomonossoff, M. E. Seliya, and M. Zaitlin. 1992. Resistance to Tobacco Virus Induced by the 54-kDa Gene Sequence Requires Expression of the 54-kDa Protein. *Mol. Plant-Microbe Interactions* 5:397404. Transgenic plants expressing the 54-kDA putative replicase gene of TMV were resistant to systemic virus disease.

Carr, J. P. and M. Zaitlin. 1991. Resistance in Transgenic Tobacco Plants Expressing a Nonstructural Gene Sequence of Tobacco Mosaic Virus Is a Consequence of Markedly Reduced Virus Replication. *Molec Plant-Microbe Interactions* 4:579–585.

Chee, P. P. and Slightom, J. L. (1991). Transfer and expression of cucumber mosaic virus coat protein gene in the genome of *Cucumis sativis*. *J. Am. Soc. Hort. Sci.* 116:1098–1102. Reports the production of transgenic cucumber plants that include a CMV transgene.

Cuozzo M., O' Connell K., Kanjewski W., Fang R X, Chua N H, and Tumer N E (1988) Viral protection in transgenic tobacco plants expressing the cucumber mosaic virus coat protein or its antisense RNA. *Biotechnology* 6:549–557.

Dawson, W. O. (1983). Tobacco mosaic virus protein synthesis is correlated with double-stranded RNA synthesis and not single-stranded RNA synthesis. *Virology* 125: 314–323.

Day, A. G., E. R. Bejarano, K. W. Buck, M. Burrell, and C. P. Lichtenstein. 1991.

Expression of an antisense viral gene in transgenic tobacco confers resistance to the DNA virus tomato golden mosaic virus. *P.N.A.S. USA* 88:6721–6725. Gemini virus tomato golden mosaic virus AL1 gene antisense expression in transgenic tobacco confers resistance to the virus.

Donson, J., G. Kurath, T. Turpen, I. A. Khan, and W. O. Dawson. 1992. Tobacco plants transgenic for non-structural genes of tobacco mosaic virus (TMV) are resistant to infection by TMV and other tobamoviruses. *Phytopathology* 82:1071 (abstr).

Duffus, J. E., Mayhew, D. E. & Flock, R. A. (1982). Lettuce infectious yellows-a new whitefly-transmitted virus of the desert southwest. (Abstr.) *Phytopathology* 72: 963. Reports the first observation of LIYV in the desert Southwest.

Duffas, J. E., Larsen, R. C. & Liu, H. Y. (1986). Lettuce infectious yellows virus-A new type of whitefly-transmitted virus. *Phytopathology* 76: 97–100. Reports the host range, symptoms and morphology of LIYV.

Enomoto, S., Itoh, H., Ohshima, M., and Ohashi, Y. (1990). Induced expression of a chimeric gene construct in transgenic lettuce plants using tobacco pathogenesis-related protein gene promoter region. *Plant Cell Reports* 9:6–9. Reports the transformation of a stress-related gene from tobacco into lettuce with the use of an improved transformation method.

Golemboski, D. B., G. P. Lomonossoff, M. Zaitlin. 1990. Plants transformed with a tobacco mosaic virus nonstructural gene sequence are resistant to the virus. *P.N.A.S. USA* 87:6311–6315.

Gonsalves D., Chee P., Prowidenti R., Seem R., and Slightom JL (1992). Comparison of Coat Protein-Mediated and Genetically-Derived Resistance in Cucumbers to Infection by Cucumber Mosaic Virus Under Field Conditions with Natural Challenge Inoculations by Vectors. *Bio/Technology* 10:1562–1570. Reports a comparison between engineered plants with plants that have traditional genetic resistance.

Gumpf, D., Bar-Joseph, M. & Dodds, J. Allan (1981). Purification of citrus tristeza virus on sucrose-$Cs_2SO_4$ cushion gradients and estimation of its RNA size. *Phytopathology* 71: 878. Reports procedures useful for the establishment of an LIYV purification procedure.

Habili, N. and Symons, R. H. (1989). Evolutionary relationship between luteoviruses and other RNA plant viruses based on sequence motifs in their putative RNA polymerases and nucleic acid helicases. *Nuc Acids Res* 17:9543–9555.

Halliwell and Johnson, J. D. (1988). Lettuce Infectious Yellows Virus Infecting Watermelon, Cantaloupe, Honey Dew Melon, Squash and Cushaw in Texas. (Abstr.) *Plant Dis.* 76:643. Reports the first observation of LIYV infection in Texas.

Hemenway C, Fang R X, Kaniewski W K, Chua N H, and Turner N E (1988, Analysis of the Mechanism of Protection in Transgenic Plants Expressing the Potato Virus X Coat Protein or its Antisense RNA. *EMBOJ* 7:1273–1280.

Kamer, G. and Argos, P. (1984). Primary structural comparison of RNA-dependent polymerases from plant, animal, and bacterial viruses. *Nuc Acids Res* 12:7269–7283.

Klaassen V. A., Boeshore, M. L. & Falk, B. W. (1992). Molecular characterization of lettuce infectious yellows virus. (Abstr.) *Phytopathology* 82:1111. Reports that the LIYV genome consists of two single stranded positive sense RNA molecules.

Klaassen V. A., Boeshore, M. L. & Falk, B. W. (1993). Molecular Characterization of the lettuce infectious yellows genome. American Society of Virology Meetings, A43 (abstract). Reports cloning of the LIYV coat protein gene.

Klaassen V. A., Boeshore, M. L., Dolja, V., & Falk, B. W. (In press). Partial characterization of the lettuce infectious yellows virus genomic RNAs, identification of the coat protein gene, and comparison of its amino acid sequence with those of other filamentous RNA plant viruses. Journal of General Virology.

Koonin, E. V. 1991. The phylogeny of RNA-dependent RNA polymerases of positive-strand RNA viruses. *J. of Gen Virol* 72:2197–2206. Discusses the proposed evolutionary relationships among positive-stranded RNA viruses based on amino acid sequence analysis of viral RNA polymerases.

Ling K., Namba S., Gonsalves C., Slightom JL, and Gonsalves D (1991). Protection Against Detrimental Effects of Potyvirus Infection in Transgenic Tobacco Plants Expressing the Papaya Ringspot Virus Coat Protein Gene. *Bio/Technology* 9:752–758.

Lockhart, B. E. L., Autrey, L. J. C. & Comstock, J. C. (1992). Partial purification and serology of sugarcane mild mosaic virus, a mealbug-transmitted closterolike virus. *Phytopathology* 82: 691–695.

Longstaff, M., G. Brigneti, F. Boccard, S. Chapman, and D. Baulcomb. 1993. Extreme resistance to potato virus X infection in plants expressing a modified component of the putative viral replicase. *EMBO Journal* 12:379–386. The motif GDD of the PVX polymerase gene was substituted with ADD and transformed into tobacco. Two of four lines transformed with the ADD form of the motif displayed high resistance to PVX infection.

MacFarlane S. A. and J. W. Davies. 1992. Plants transformed with a region of the 201-kilodalton replicase gene from pea early browning virus RNA1 are resistant to virus infection. *P.N.A.S. USA* 89:5829–5833. The 3' end (54K ORF) of pea early browning virus (PEBV) 201-kDa putative replicase gene was transformed into tobacco. Plants transformed with the 54 k ORF of PEBV were resistant to infection by PEBV at inoculum doses of up to 1 mg/ml.

Maiti et al., 1993, *PNAS* 90:6110–6114. Expression of the protease gene (NIa) confers resistance to tobacco vein mottle virus (TVMV).

McCreight, J. D., Kishaba, A. N., Mayberry, K. S. (1986). Lettuce Infectious Yellows Tolerance in Lettuce. *J. Amer. Soc. Hort. Sci.* 111(5):788–792. Study assesses lettuce varieties for tolerance or resistance to LIYV under field conditions and reports that none appeared to give commercially acceptable levels of protection.

Murashige, T. and F. Skoog 1962 *Physiol Plantarum* 15:473–497. Discloses media formulations used in plant transformation procedures.

Pappu et al. American Society for Virology Meeting, Davis, Calif., Jul. 11–14, (1993) report finding a heat shock gene in citrus tristeza virus (CTV).

Powell-Abel, P., R. S. Nelson, B. De., N. Hoffman, S. G. Rogers, R. T. Fraley, R. N. Beachy, 1986. Delay of disease development in transgenic plants that express the tobacco mosaic virus coat protein gene. *Science* 232:738–743. Reports that plants can be protected from viral infection by transforming viral genes into plants.

Quemada et al. (1991). Expression of cucumber mosaic virus strain-c coat protein gene: analysis of protection gene: analysis of protection against infectious by CMV strains C, W L, or CHI using mechanical or aphid transmission vectors. *Phytopathology, Vol.* 81, pp. 794–802.

Sekiya, M. E., Lawrence, S. D., McCaffery, M. and Cline, K (1991). Molecular cloning and nucleotide sequencing of the coat protein gene of citrus tristeza virus. *Journal of General Virology* 72: 1013–1020. Reports that citrus tristeza virus appears to be closely related to lettuce infectious yellows virus at the molecular level.

Slightom, J. L., (1991). Custom PCR Engineering of a Plant Expression Vector. *Gene* 100:251–255. Reports the construction of the cpexpress plant expression cassette.

Szybalski, W. 1991. Editorial: Protection of plants against viral diseases by cloned viral genes and anti-genes. *Gene* 107:177–179.

Turner N E, O'Connell K M, Nelson R S, Sanders P R, Beachy R N, Fraley R T, and Shah D M (1987) Expression of Alfalfa Mosaic Virus Coat Protein Gene Coufers Cross Protection in Transgenic Tobacco and Tomato Plants. *EMBO J* 6:1181–1188. Reports that plants transformed with a virus coat protein gene possess protection against viral infection.

Wilson, T. M. A. (1993). Strategies to protect crop plants against viruses: Pathogen-derived resistance blossoms. *Proc. Natl. Acad. Sci. USA* 90: 3134–3141. A review of the literature on engineered virus protection in plants.

Woudt et al. (poster display at American Society for Virology Meeting, Davis, California, Jul. 11–14, 1993) reported finding a heat shock protein in cucumber chlorotic spot virus (CCSV).

SUMMARY OF THE INVENTION

The present invention relates to the following Lettuce Infectious Yellows Virus (LIYV) genes: the coat protein gene [SEQ ID NO: 1], the heat shock protein-70 gene [SEQ ID NO:6], the RNA polymerase gene [SEQ ID NO: 11], the gene encoding open reading frame 3 (ORF) of LIYV RNA1 [SEQ ID NO:16], and the gene encoding ORF 6 of LIYV RNA2 [SEQ ID NO:21].

More specifically, the present invention provides an isolated nucleic acid which contains a nucleotide sequence which encodes at least a portion of one of five LIYV proteins: the coat protein, the heat shock protein-70, RNA polymerase, the protein encoded by the gene positioned at ORF 3 of LIYV RNA1, and the protein encoded by the gene positioned at ORF 6 of LIYV RNA2. The nucleotide sequences for these proteins, either in the sense or the antisense orientation, are operably linked to genetic regulatory sequences necessary for gene expression to form plant transformation vectors. Specifically, an LIYV nucleotide sequence, or its antisense complement, is operably linked to and positioned downstream from a promoter and a polyadenylation signal is operably linked and positioned downstream from the nucleotide sequence.

Plant transformation vectors which contain a gene, or a portion of a gene, for a lettuce infectious yellows virus protein, such as the coat protein gene, the heat shock protein-70 gene, the RNA polymerase gene, the LIYV RNA1 ORF 3 gene, and a portion of the LIYV RNA2 ORF 6 gene and, additionally, the necessary genetic regulatory sequences needed for expression of a gene transferred into a plant, are used to transform bacterial or plant cells with the LIYV gene or genes present in the isolated nucleic acid. Furthermore, the present invention relates to transgenic plants which are produced from plant cells transformed with an isolated nucleic acid containing a nucleotide sequence or nucleotide sequence fragment from lettuce infectious yellows virus, the gene or fragment being selected from the group consisting of the coat protein gene, the heat shock protein-70 gene, the RNA polymerase gene, the LIYV RNA1 ORF 3 gene, and the LIYV RNA2 ORF 6 gene. In addition, the present invention relates to a process of producing transgenic plants which have increased resistance to viral infection.

BRIEF DESCRIPTION OF THE FIGURES

FIGS. 1A–1B illustrate the PCR oligomer reaction primers [SEQ ID NOS:3 and 4] and the novel restriction enzyme cloning sites for each of the primers used for the amplification of the DNA nucleotide sequence of the LIYV coat protein [SEQ ID NO: 1] from the portion of the LIYV genome [SEQ ID NO:5] containing the cDNA nucleotide sequence of the LIYV coat protein as well as the deduced amino acid sequence [SEQ ID NO:2] of the LIYV coat protein;

FIGS. 2A–2B illustrate the engineering steps used to install the LIYV coat protein gene coding sequences into the plant expression vector pUCcpexpress and the subsequent insertion of the LIYV coat protein expression cassette into pGA482G to yield LCP2115, genetic maps of LCP2115, LIYVCP13cpexpress and LCP1371 are also shown;

FIG. 3 illustrates the cDNA nucleotide sequence [SEQ ID NO: 1] of the LIYV coat protein;

FIG. 4 illustrates the deduced amino acid sequence [SEQ ID NO:2] of the LIYV coat protein;

FIGS. 6A–6B illustrate a detailed flow chart showing the genetic maps of some of the plasmids used to install the LIYV heat shock protein-70 gene coding sequences eventually into plants;

FIGS. 7A–7B illustrate the PCR oligomer reaction primers [SEQ ID NOS:8 and 9] and the novel restriction enzyme cloning sites for each of the primers used for the amplification of the cDNA nucleotide sequence [SEQ ID NO:6] of the LIYV heat shock protein-70 from the portion of the LIYV genome [SEQ ID NO:10] containing the cDNA nucleotide sequence of the LIYV heat shock protein-70 as well as the deduced amino acid sequence [SEQ ID NO:7] of the LIYV heat shock protein-70;

FIGS. 8A–8B illustrate the cDNA nucleotide sequence [SEQ ID NO:6] of the LIYV heat shock protein-70;

FIGS. 9A–9B illustrate the deduced amino acid sequence [SEQ ID NO:7] of the LIYV heat shock protein-70;

FIGS. 10A–10B illustrate the PCR oligomer reaction primers [SEQ ID NOS:13 and 14] and the novel restriction enzyme cloning sites for each of the primers used for the amplification of the cDNA nucleotide sequence [SEQ ID NO: 11] of the LIYV RNA polymerase from the portion of the LIYV genome [SEQ ID NO: 15] containing the cDNA nucleotide sequence of the LIYV RNA polymerase as well as the deduced amino acid [SEQ ID NO:12] sequence of the LIYV RNA polymerase;

FIGS. 12A–12B illustrate the cDNA nucleotide sequence of the LIYV RNA polymerase [SEQ ID NO: 11];

FIGS. 13A–13B illustrate the deduced amino acid sequence of the LIYV RNA polymerase protein [SEQ ID NO:12];

FIG. 14 illustrates the PCR oligomer reaction primers [SEQ ID NOS:18 and 19] and the novel restriction enzyme cloning sites for each of the primers used for the amplification of the cDNA nucleotide sequence [SEQ ID NO:16] of ORF 3 of LIYV RNA1 from the portion of the LIYV genome [SEQ ID NO:20] containing the cDNA nucleotide sequence of ORF 3 of LIYV RNA1 as well as the deduced amino acid [SEQ ID NO: 17] sequence of ORF 3 of LIYV RNA1;

FIG. 16 illustrates the cDNA nucleotide sequence of the LIYV RNA1 ORF 3 [SEQ ID NO: 16];

FIG. 17 illustrates the deduced amino acid sequence of the LIYV RNA1 ORF 3 protein [SEQ ID NO:17];

FIG. 18 illustrates the PCR oligomer reaction primers [SEQ ID NOS:23 and 24] and the novel restriction enzyme cloning sites for each of the primers used for the amplification of a portion of the cDNA nucleotide sequence [SEQ ID NO:25] from the LIYV genome containing the cDNA nucleotide sequence [SEQ ID NO:21] of LIYV RNA2 ORF 6 as well as the deduced amino acid [SEQ ID NO:22] sequence of LIYV RNA2 ORF 6;

FIG. 20 illustrates the cDNA nucleotide sequence of LIYV RNA2 ORF 6 [SEQ ID NO:21];

FIGS. 21A–21B illustrate the deduced amino acid sequence of the LIYV RNA2 ORF 6 protein [SEQ ID NO:22];

FIG. 22 illustrates a map of the LIYV genome; and

DESCRIPTION OF THE PREFERRED EMBODIMENT

Figure 23:
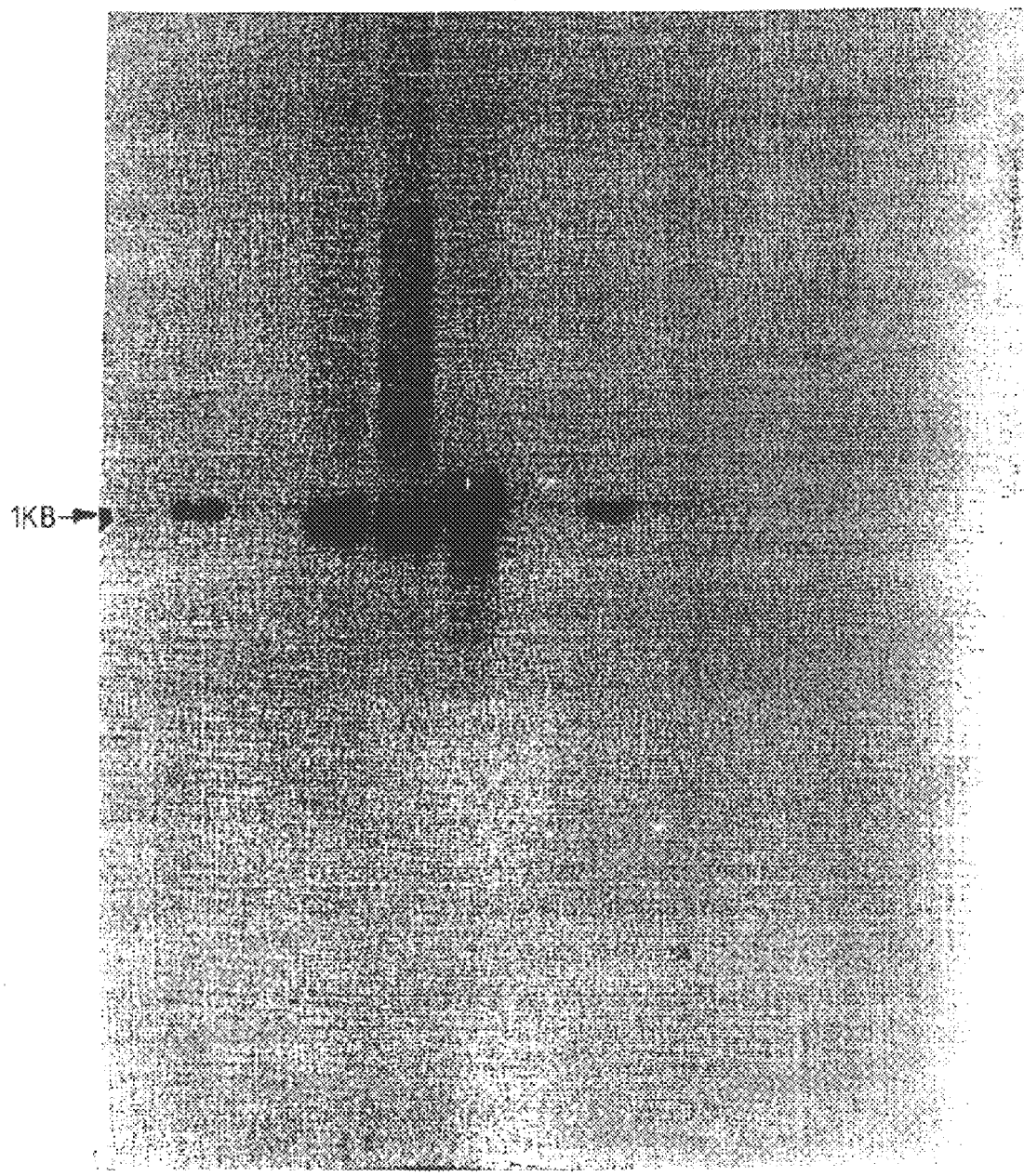
FIG. 23 illustrates RNA blot hybridization results obtained with two segregating lines (2115–57 and 2115–67) of LIYV CP transgenic lettuce.

FIGS. 1A–1B to 23 are set forth to illustrate the constructions of this invention. Certain conventions are used to illustrate plasmids and DNA fragments as follows:

(1) The single line figures represent both circular and linear double-stranded DNA.

(2) Asterisks (*) indicate that the molecule represented is circular. Lack of an asterisk indicates the molecule is linear.

(3) Junctions between natural boundaries of functional components are indicated by vertical lines along the horizontal lines.

(4) Genes or functional components are indicated.

(5) Restriction sites are indicated above the horizontal lines.

(6) Distances between genes and restriction sites are not to scale. The figures show the relative positions only unless indicated otherwise.

Most of the recombinant DNA methods employed in practicing the present invention are standard procedures; well known to those skilled in the art, and described in detail, for example, in European patent application EP-223452, published Nov. 29, 1986, which is incorporated herein by reference. Enzymes are obtained from commercial sources and are used according to the vendor's recommendations or other variations known to the art. Reagents, buffers, and culture conditions are also known to those in the art. General references containing such standard techniques include the following: R. Wu, ed. (1979) *Methods in Enzymology*, Vol.68; J. H. Miller (1972) *Experiments in Molecular Genetics;* T. Maniatis et al. (1982) *Molecular Cloning: A Laboratory Manual;* D. M. Glover, ed. (1985) *DNA Cloning*, Vol. II; and S. B. Gelvin and R. A. Schilperoort, eds. *Introduction, Expression, and Analysis of Gene Products in Plants,* all of which are incorporated by reference.

To practice the present invention, a gene of the LIYV virus must be isolated from the viral genome and inserted into a recombinant DNA vector containing the genetic regulatory sequences necessary to express the inserted gene. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct and possess increased resistance to viral infection as a result To practice the present invention, a quantity of virus is grown up and harvested using methods well known in the art. The viral RNA is then purified and a cDNA library is constructed using viral RNA. The methods followed to do this are well known in the art. Specifically, the viral RNA is treated with reverse transcriptase and a complementary DNA molecule is produced. A DNA complement of the complementary DNA molecule is produced and that sequence represents a DNA copy of the original viral RNA molecule. Thus, a double stranded DNA molecule is generated which contains the sequence information of the viral RNA. These DNA molecules can be cloned in E. coli plasmid vectors after the additions of restriction enzyme linker molecules by DNA ligase. The various fragments are inserted into cloning vectors which are then used to transform E. coli and create a cDNA library.

To identify an LIYV gene such as the coat protein gene, the LIYV cDNA clones are sequenced and nucleotide sequence analyses are performed using computer sequence analysis software. Nucleotide sequence analysis of LIYV virion cDNA clones reveals two clone linkage groups: LIYV105 and LIYV182. Purified LIYV coat protein is then subjected to amino acid sequence analysis to determine a partial amino acid sequence. This partial amino acid sequence is compared with the deduced amino acid sequence for LIYV ORFs to locate the position of the LIYV coat protein gene. Polymerase chain reaction (PCR) primers are then used to amplify the putative LIYV coat protein gene from the original cDNA clone template. In vitro transcription and translation analyses are then used to confirm the identity of the coat protein gene. Specifically, immunoblot analysis is used to confirm the identity of the coat protein gene.

Alternatively, LIYV genes can be identified by sequencing the LIYV cDNA clones and assembling them into linked groups based on nucleotide sequence content. Open reading frames (ORFs) are identified by computer mapping programs. The identity of the proteins encoded by the various ORFs is accomplished by a FASTA search of UWGCG amino acid sequence data bases. The search reveals that one ORF in the LIYV RNA potentially codes for the HSP70 heat shock protein and a second ORF potentially codes for RNA polymerase.

The heat shock protein-70 family is one of the most highly conserved groups in evolution (Gething, M. J. and Sambrook, J. (1992), *Nature,* 355:33–45). By computer analysis, Agranovsky et al. (1991), *J. Mol. Biol.* 217:603–610, compared beet yellow virus HSP-70 with other HSP-70 sequences in the literature. They reported that eight amino acid sequences are highly conserved in heat shock 70 proteins, including beet yellows virus heat shock protein. Agranovsky et al., *J. Gen. Virol.* 72: 15–23 (1991) also report that an open reading frame (ORF) coding for RNA polymerase, heat shock protein and coat protein had been identified in beet yellows closterovirus RNA genome. In addition, Woudt et al. recently reported finding a heat shock protein in cucumber chlorotic spot virus (CCSV) (poster display at American Society for Virology Meeting, Davis, Calif., Jul. 11–14, 1993). Pappu et al. (1993) also reported at the same meeting finding a heat shock gene in citrus tristeza virus (CTV). The role of heat shock proteins in the life cycle of beet yellows virus and lettuce infectious yellows virus is not known.

As to LIYV RNA polymerase, Koonin (1991) report that viral putative RNA-dependent RNA polymerases include eight distinct conserved amino acid sequence motifs. A large number of viral polymerases have been identified (Bruenn, (1991); Habili and Symons, (1989) and Kamer and Argos, (1984)). A search of amino acid sequence data bases has not identified the identity of the protein encoded by the gene positioned at ORF 3 of LIYV RNA1 or the protein encoded by the gene positioned at ORF 6 of LIYV RNA2 as of yet.

Having determined the nucleotide sequence of the LIYV coat protein, the LIYV heat shock protein-70, the LIYV RNA polymerase, the gene positioned at ORF 3 of LIYV RNA1, and the gene positioned at ORF 6 of LIYV RNA2, one or more of the genes are inserted into recombinant DNA expression vectors in either the sense, or the antisense, orientation. The expression vectors contain the necessary genetic regulatory sequences for expression of an inserted gene. The LIYV genes are inserted such that those regulatory sequences are functional so that the genes can be expressed when incorporated into a plant genome.

In order to express the viral gene, the necessary genetic regulatory sequences must be provided because the LIYV genes of the present invention isolated from viral RNA do not contain the genetic regulatory sequences needed for gene expression. The LIYV genes of the present invention do not contain the transcription and translation signals necessary for their expression once transferred and integrated into a plant genome. They must, therefore, be engineered to contain a plant expressible promoter, a translation initiation codon (ATG) and a plant functional poly(A) addition signal (AATAAA) 3' of its translation termination codon. In the present invention, at least one LIYV gene is selected from the group consisting of the coat protein gene, the heat shock protein-70 gene, the RNA polymerase gene, the gene positioned at ORF 3 of LIYV RNA1, and/or the gene positioned at ORF 6 of LIYV RNA2, is inserted into a vector which contains a cloning site for insertion 3' of the initiation codon and 5' of the poly(A) signal. The promoter is 5' of the initiation codon such that when a structural gene is inserted at the cloning site, a functional unit is formed in which the inserted gene is expressed under the control of the various genetic regulatory sequences.

In the preferred embodiment of the present invention, additional genetic regulatory sequences are provided. As described above, an expression vector must contain a promoter, an initiation codon and a poly(A) addition signal. The promoter used is one that is chosen for high level expression, such as Cauliflower mosaic virus CaMV 35S promoter. In addition to the CaMV 35S promoter, a number of other promoters which are active in plant cells have been described in the literature. These include the *Commelina Yellow Mottle Virus* promoter (Medberry et al., *The Plant Cell Vol.* 4, 185–192 (Feb. 1992) and Medberry et al., *Nucleic Acids Research,* Vol. 18, No. 18, 5505–5513), the nopaline synthase (NOS) and octopine synthase (OCS) promoters (which are carried on tumor inducing plasmids of *Agrobacterium tumefaciens*), the Cauliflower Mosaic Virus 19 S promoter, and the light-inducible promoter from the small subunit of ribulose bis-phosphate carboxylase (ssRUBISCO, a very abundant plant polypeptide). All of these promoters and others have been used to create various types of DNA constructs which have been expressed in plants.

Promoters which are known or are found to cause transcription of viral RNA in plant cells can be used in the present invention. Such promoters may be obtained from plants or viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of LIYV protein to render the plant substantially resistant to virus infection. The amount of LIYV protein needed to induce resistance may vary with the type of plant. Accordingly, while the CaMV35S promoter is preferred, it should be understood that this promoter may not be the optimal one for all embodiments of the present invention.

The promoters used in the recombinant DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. For purposes of this description, the phrase "CaMV35S" promoter thus includes variations of CaMV35S promoter, e.g., promoters derived by means of ligation with operator regions, random or controlled mutagenesis as well as tandem or multiple copies of enhancer elements, etc.

A coding sequence used in a DNA construct of this invention may be modified, if desired, to create mutants, using methods known to those skilled in the art. Such mutants and variants are therefore within the scope of the present invention. Accordingly, references to the coat protein, heat shock protein-70, RNA polymerase, the protein encoded by the gene positioned at ORF 3 of LIYV RNA1 or the protein encoded by the gene positioned at ORF 6 of LIYV RNA2 include truncated proteins and fusion proteins, as well as unmodified proteins.

While in most cases the DNA which is inserted into plant cells will contain separate genes which encode individually for the LIYV coat protein, heat shock protein-70, RNA polymerase, the protein encoded by the gene positioned at ORF 3 of LIYV RNA1 or the protein encoded by the gene positioned at ORF 6 of LIYV RNA2, such is not critical. In such cases, each gene would contain a 5' promoter region, a 5' non-translated region, a structural coding region which encodes either of the above named LIYV proteins as well as a 3' non-translated region containing a functional polyadenylation signal. Those skilled in the art will recognize that one may be able to produce a fusion polypeptide containing two or more of the above-named LIYV proteins from a single gene and obtain the attendant resistant to LIYV. Therefore, such a modified LIYV gene is considered to be within the scope of the present invention in addition to the other gene modifications described above.

A DNA construct of the present invention can be inserted into the genome of a plant by any suitable method. Suitable plant transformation vectors include those derived from a Ti plasmid of *Agrobacterium tumefaciens*, such as those disclosed by Schilperoort, et al. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electoporation, chemicals that increase free DNA uptake, and transformation viruses.

A DNA construct prepared in accordance with the present invention is preferably introduced, via a suitable vector as described above, into lettuce cells or protoplasts derived from lettuce plants. Regenerated plants which are tested for virus resistance are preferably exposed to the virus at a concentration that is in a range where the rate of disease development correlates linearly with virus concentration in the inoculum. This linear range can be determined empirically, using non-transformed plants. Methods for virus inoculation are well-known to those skilled in the art, and are reviewed by Kado & Agrawal (1972). One method involves abrading a leaf surface with an aqueous suspension (typically buffered at pH 7–8) containing an abrasive material, such as carborundum or diatomaceous earth, and the virus. While inoculation in this manner is often preferred, those skilled in the art will recognize that other approaches may be used such as simply swabbing the virus inoculum on to the leaf surface or inoculation by insect vectors, such as aphids.

Therefore, using methods well known to those skilled in the art, plant cells are transformed with the vector construct and the plant cells are induced to regenerate. The resulting plants contain the coat protein genes and produce the coat protein. The production of the protein confers upon the plant an increased resistance to infection by the virus form which the coat protein gene was derived.

Other features and advantages of the present invention will become apparent from the following description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

TRANSFORMATION OF LETTUCE PLANTS WITH LIYV COAT PROTEIN

EXAMPLE 1

Virion Purification and RNA Isolation

Lettuce infectious yellows virus was propagated in *Chenopodium murale* and *Nicotiana clevelandii* by standard methods such as described by Duffus et al. (1986). Three LIYV isolates were used during these studies. Isolates 87, 90 (kindly supplied by R. Creamer, University of California—Riverside) and 92 (kindly supplied by J. Duffus, USDA, Salinas, Calif.) were obtained from LIYV-infected *Lactuca sativa L.* in the Imperial Valley of California.

The procedures from several virion purification protocols for filamentous plant viruses (Duffus et al., 1986; Lockhart and Autrey, 1988) were combined and modified to purify LIYV virions. Specifically, 100 grams of fresh, LIYV-infected tissue was ground in liquid nitrogen using a mortar and pestle. The powder was stirred for 10 minutes in 500 ml 0.1M Tris-HCl, pH 7.4, containing 0.5% (w/v) Na2SO3 and 0.5% (v/v) 2-mercaptoethanol. The crude extract was strained through cheesecloth, Triton X-100 was added to a final concentration of 2% (v/v) and the extraction stirred at 4 degrees C. for 1 hour. The mixture was centrifuged in a Sorvall GSA rotor (DuPont Co.) at 7,800 rpm (10,000 g) for 10 minutes, and the pellet discarded.

The retained supernatant was layered over 6 ml of 20% (w/v) sucrose in TE (0.01M Tris-Hcl, pH 7.4, 1 mM EDTA), and centrifuged for 1 hour at 28,000 rpm (93,000 g max) in a Beckman 45 Ti rotor (Beckman Instruments). The pellets were resuspended overnight at 4 degrees C. in 5 ml TE, pH 7.4. Triton X-100 was then added to the suspension at a final concentration of 2% (v/v) and again stirred for 1–2 hours at 4 degrees C., followed by centrifugation in a Sorvall GSA rotor at 7,800 rpm (10,000 g) for 10 minutes, and the pellet discarded.

The retained supernatant was layered over 4 ml of 20% (w/v) sucrose in TE, pH 7.4, and centrifuged for 2 hours at 30,000 rpm (93,000 g max) in a Beckman 70 Ti rotor. The pellets were resuspended overnight in 3 ml TE, pH 7.4. The suspension was centrifuged in a Sorvall 55–34 rotor at 7,500 rpm (8,000 g) for 10 minutes, and the pellet discarded. The supernatant was layered on step gradients prepared as described by Gumpf et al. (1981). Gradients were centrifuged for 5 hours at 28,000 rpm (140,000 g max) in a Beckman SW 40 rotor, followed by fractionation using a Model 640 density gradient fractionator (ISCO, Inc.). Fractions containing LIYV virions were pooled and dialyzed at 4 degrees C. against several changes of TE, pH 7.4.

Virions were immediately extracted for RNA in 0.1M Tris-HCl, pH 8.0, 5 mM EDTA, 1.5% SDS, 200 units RNasin (Promega), and 100 micrograms/ml Proteinase K (Boerhinger Mannheim). After 30 minutes at 37 degrees C., the solution was extracted twice with phenol-chloroform and RNA was recovered by ethanol precipitation. RNA was resuspended in water and either analyzed on non-denaturing 0.8% agarose gels in TAE (40 mM Tris-HCl, pH 7.9, 2.5 mM NaC2H3O2, 0.5 mM EDTA), or denatured in glyoxal and DMSO (McMaster and Carmichael (1977) PNAS, 74:4835–4837) and analyzed on 1% agarose gels in 20 mM HEPES, 1 mM EDTA, pH 7.0. Total RNAs were extracted from healthy and LIYV-infected plants as described by Dawson, (1983) Virolog, 125:314–323. Single-stranded and double-stranded RNAs were separated by 2M LiCl fractionation (Baltimore (1966), Journal of Molecular Biology, 18:421–428. Total single-stranded RNAs were resuspended in water, aliquoted, and stored at −70 degrees C.

EXAMPLE 2

Complementary DNA (cDNA) Synthesis and Cloning

Virion RNA (approximately 1 microgram) was polyadenylated as described by Huiet et al. (1992). After phenol-chloroform extraction and ethanol precipitation, one half of the polyadenylated RNA was used for the construction of a cDNA library. The cDNA synthesis and subsequent cloning into the plasmid pSPORT were done according to instructions provided for the Superscript Plasmid System cDNA synthesis and cloning kit available from Bethesda Research Laboratories, Gaithersburg, Md. 20877.

EXAMPLE 3

Plasmid Analysis

Ampicillin-resistant colonies (approx. 200) were selected and recombinant plasmids were purified using the alkaline lysis method (Bimboim & Doly, 1979). Plasmids were analyzed by digestion with the restriction endonuclease Mu 1 (New England Biolabs), followed by electrophoresis in 0.8% agarose gels in TAE. Those colonies containing the plasmids with the largest cDNA inserts (approx. 2000–5000 bp) were selected for further study.

EXAMPLE 4

Confirmation of cDNA as Copy of Virion RNA

Total ssRNA was denatured, separated by gel-electrophoresis, and transferred to a nylon membrane such as HYBOND N+(available from Amersham) in 50 mM NaOH for 4 hours according to the manufacturer's protocol. Blots were rinsed in 2X SSC (0.3M NaCl, 30 mM trisodium citrate) and hybridized to 32P-labelled LIYV cDNA clones according to the procedure of Amasino (1986). Probes were synthesized using the Sequenase Random-primed DNA Labeling Kit (U.S. Biochemicals).

EXAMPLE 5

Nucleotide Sequence Analysis

Nucleotide sequence analysis was performed on both strands of LIYV cDNA clones by the dideoxynucleotide chain termination method of Sanger et al. (1977) using the Sequenase kit (U.S. Biochemicals). LIYV sequences were obtained either from subclones generated by exonuclease m and nuclease S1 digestion from primary cDNA clones or from original cDNA clones by priming reactions using synthetic oligonucleotide primers. Nucleotide sequence analyses were performed using the software DNA Strider for Apple MacIntosh and Genetics Computer Group sequence analysis software from the University of Wisconsin. Nucleotide sequence analysis of LIYV virion cDNA clones revealed two clone linkage groups: RNA1 and RNA2 (FIG. 22). LIYV-infected plant RNA and LIYV virion RNA blot hybridization experiments indicated that the LIYV genome consists of two different ssRNAs.

EXAMPLE 6

Coat Protein Isolation and Analysis

Purified LIYV virions were disrupted in 30 mM Tris-HCl, pH 6.8, 1% SDS-polyacrylamide gel electrophoresis (SDS-PAGE) (Laemmli, 1970), and proteins were visualized by silver staining (Morrisey, 1981).

Purified LIYV coat protein was subjected to amino acid sequence analysis using both intact and proteolyzed protein preparations. Proteolytic fragments were generated by first separating LIYV coat protein by SDS-PAGE. Proteins were then transferred to ProBlot (Applied Biosystems) and visualized by staining with Coomassie brilliant blue, G-250. The LIYV coat protein was excised from the membrane and treated under partial proteolysis conditions with cyanogen bromide (Protein Structure Lab at University of California—Davis. The resulting peptides were separated by SDS-PAGE and transferred to ProBlot. After staining, the major cleavage product was excised and subjected to automated Edman degradation using a Beckman 890M liquid phase sequencer (Protein Structure Lab at University of California— Davis).

A partial amino acid sequence was determined for LIYV coat protein and compared with the deduced amino acid sequences for LIYV ORFs. The partial amino acid sequence is glu-lys-thr-ileu-asn-asn-ileu-arg-gln-ala-gly-ileu. This partial LIYV coat protein amino acid sequence was found in a gene located in the LIYV RNA2 (LIYV105) linkage group (FIG. 22). The coat protein gene is 747 nucleotides long and encodes a 27.7-kD protein (FIGS. 1A–1B, 3 and 4)[SEQ ID NOS:1 and 2].

EXAMPLE 7

Verification of the LIYV Coat Protein Gene

A 800 bp polymerase chain reaction (PCR) fragment containing the entire putative LIYV coat protein gene [SEQ ID NO:5] was generated using oligonucleotide primers RMM-306 (5'GAATTCGCCATGGATACAG 3', complementary to the 5' end of the coat protein ORF and including EcoR I and Nco I sites [SEQ ID NO:3]) and RMM-307 (5'GGATCCCCCATGGCTGGAGGTTAG 3' complementary to the 5' end of the coat protein ORF and including Bam HI and Nco I sites [SEQ ID NO:4])(FIGS. 1A–1B). This fragment was digested with EcoRI and Bam HI and subcloned into pGEMEX-1 (Promega) downstream and in-frame with the 5-terminal 780 nucleotides of bacteriophage T7 gene 10. Two clones with inserts of the expected size were selected and partially sequenced to confirm the orientation and identity of the putative LIYV coat protein gene.

In vitro transcription and translation analyses were used to confirm the identity of the coat protein gene. Transcripts were generated using T3 RNA Polymerase (New England Biolabs) as described by Huiet et al. (1992). Transcripts were translated in wheat germ extract (Promega) in the presence of [35S]-methionine (Amersham). Labeled proteins were analyzed by electrophoresis on 12% SDS-PAGE gels followed by autoradiography. Protein products were further analyzed by immunoprecipitation using polyclonal antibodies to purified LIYV coat protein according to the procedure of Dougherty and Hiebert (1980). Specific polyclonal antiserum was prepared to gel-purified LIYV coat protein in a New Zealand white rabbit. Equal volumes of purified LIYV coat protein and Freund's adjuvant were mixed and the rabbit was injected intramuscularly once a week for 7 weeks with a total of 550 micrograms of coat protein. Freund's complete adjuvant was used for the first injection and incomplete adjuvant was used in all subsequent injections. Immunoblot analysis shows that the LIYV antibody reacts specifically with both native LIYV coat protein and with coat protein encoded by the LIYV coat protein ORF.

The PCR fragment of the putative LIYV coat protein gene was also expressed as a fusion protein in *E. coli*. The same pGEMEX-1 clone which had been translated and transcribed in vitro was transformed into JM101 (DE3) competent *E. coli*. Several recombinant colonies were selected, grown, and protein expression induced according to the manufacturer's protocol.

Proteins were analyzed by SDS-PAGE and visualized by staining with Coomassie brilliant blue, G-250.

One culture containing a fusion protein of the correct size was further characterized by Western blot analysis (Burnette, 1981). After SDS-PAGE, proteins were transferred to nitrocellulose (Schleicher & Schuell) and probed with antisera to LIYV coat protein, LMV coat protein, and T7 gene 10 leader peptide. Positive serological reactions were detected using goat anti-rabbit IgG conjugated with alkaline phosphatase (Bio-Rad Laboratories), and nitroblue tetrazolium and 5-bromo-4-chloro-3-indoyl phosphate (Bio-Rad Laboratories).

EXAMPLE 8

Construction of a pFLAG clone containing the LIYV coat protein gene

Figure 2A:
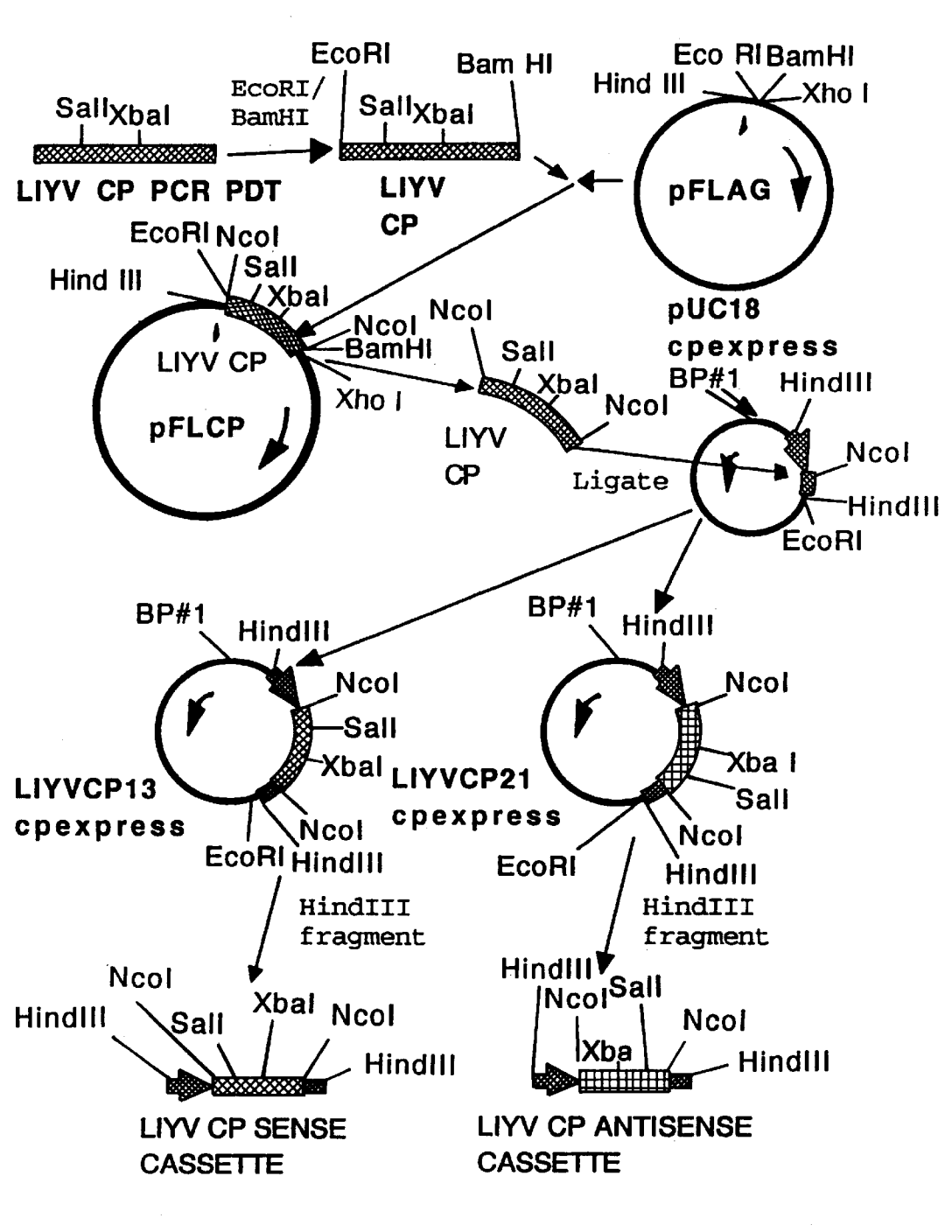
Figure 2B:
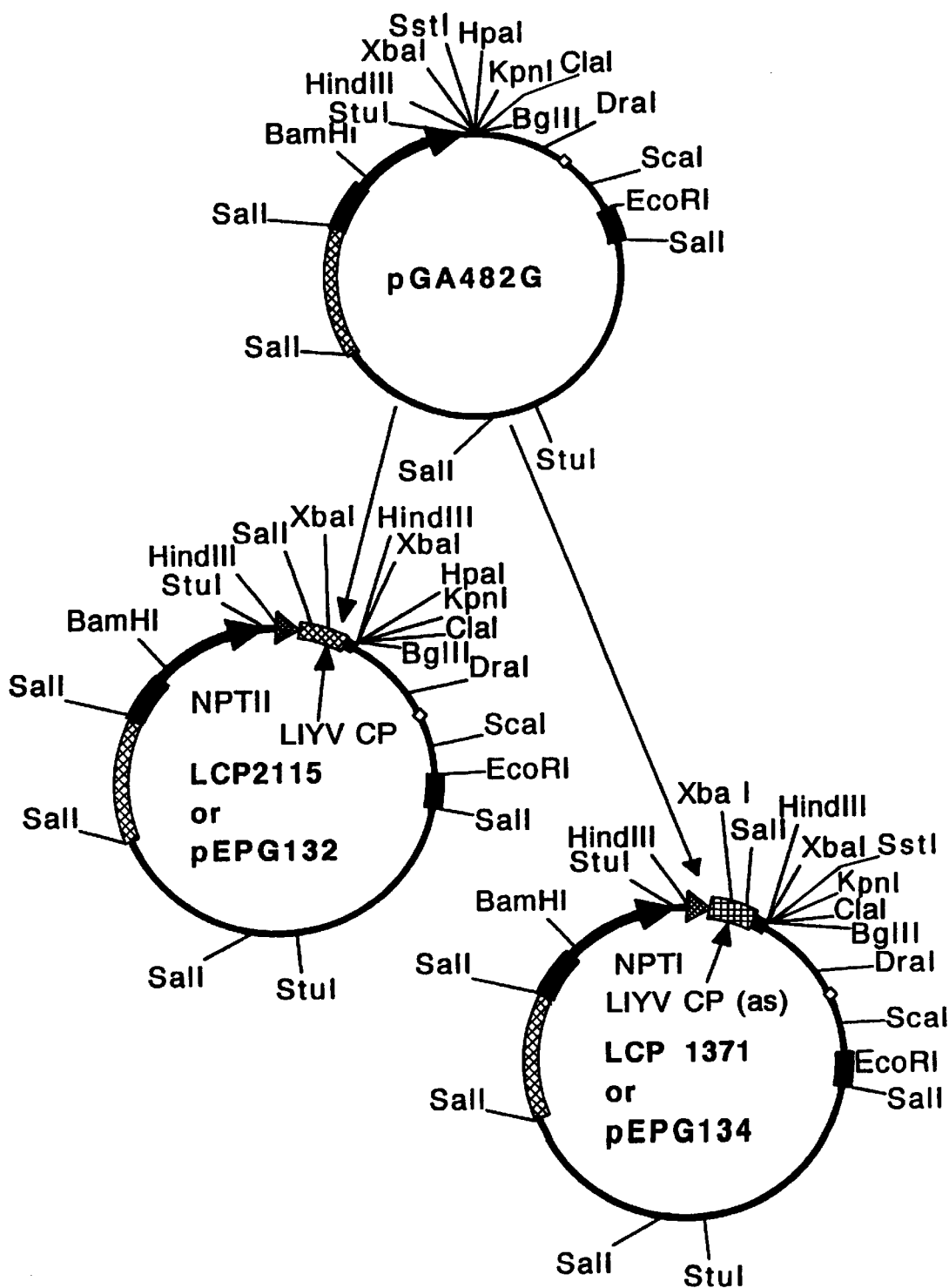

The oligonucleotides RMM 306 [SEQ ID NO:3] and RMM 307 [SEQ ID NO:4] were used to prime the polymerase chain reaction used to install restriction enzyme recognition sites for engineering the coat protein coding sequence into the bacterial expression plasmid pFLAG (Eco RI and BamHI) and into a plant expression cassette (NcoI) (FIGS. 1A–1B and 2A–2B). To begin the transfer of the LIYV coat protein gene into a plant expression cassette, the PCR-amplified coat protein gene DNA fragment was digested simultaneously with Eco RI and Barn HI to give appropriate 'sticky ends' for insertion into the plasmid vector pFLAG. This plasmid is commercially available from Kodak of Rochester, New York, and is designed to express cloned genes in *E. coli*. Using standard methods, the LIYV coat protein gene Eco RI-Bam HI fragment was directionally inserted into pFLAG that also had been digested with Barn HI and Eco RI (FIGS. 2A–2B). The resulting plasmid is called pFLCP. LIYV coat protein gene DNA inserted into pFLAG with these restriction sites codes for a translational fusion protein that includes the OmpA signal peptide and the flag peptide at the amino terminal end.

EXAMPLE 9

Binary Plasmid LIYV Coat Protein Gene Expression Cassette Construction

With reference to FIGS. 2A–2B, the plant expressible coat protein gene was then moved into a vector suitable for plant expression and Agrobacterium-mediated gene transfer. Following digestion with Nco I, the Nco I to Nco I fragment that harbors the LIYV coat protein gene was excised from pFLCP and inserted into the Nco I site of the plasmid vector pUC18cpexpress (constructed according to J. L. Slightom, 1991, *Gene*, Vol. 100, p. 251–255, "Custom PCR Engineering of a Plant Expression Vector"). Recombinant pUC18cpexpress plasmids were recovered that include the LIYV coat protein coding NcoI fragment inserted in both sense and antisense orientations. Sense orientation is designed to give sense mRNA that can be translated into LIYV coat protein in the plant. Standard recombinant methods were used to create the expression cassette in plasmid LIYV CP21cpexpress. The expression cassette includes about 330 base pairs of the CaMV 35S transcript promoter and 70 bp of the cucumber mosaic virus 5'-untranslated region. The region flanking the 3' end of the inserted gene includes 200 bp of the CaMV35S transcript poly (A) addition signal. The Nco I site maintains the AUG translation initiation site found in the LIYV coat protein gene. Nucleotide sequencing of LIYV coat protein gene DNA after insertion into pUC18cpexpress revealed that no nucleotide changes were introduced during the PCR engineering step.

The antisense orientation of the NcoI fragment in pUC18cpexpress is designed to transcribe mRNA in the plant that is complementary to the sense mRNA, and no LIYV coat protein can be translated in the plant from this construct. pUC18cpexpress plasmid that harbors the LIYV coat protein NcoI fragment in an antisense orientation is called LIYVCP13cpexpress (FIGS. 2A–2B). A HindIII fragment that harbors an LIYV coat protein AS gene expression cassette (LIYVCP13cpexpress) was excised and inserted into the unique HindIII site of pGA482G (Ling et al., 1991) to yield the plasmid LCP1371 (FIGS. 2A–2B). This binary plasmid was transformed into Agrobacterium and the resulting Agrobacterium strain was used to perform lettuce plant transformation procedures. Plants have been obtained that include the LIYV coat protein antisense gene construct. We have shown that they express NPTII protein by ELISA and that 5 of 5 tested to date by PCR contain LIYV coat protein coding sequences.

With reference to FIGS. 2A–2B, a Hind III fragment that harbors the LIYV coat protein gene expression cassette (LIYV CP21 cpexpress) was excised by Hind III digestion and inserted into the unique Hind m site of the plasmid vector pGA482G (P. Russell, 1993)(available from Gynehung An, Institute of Biological Chemistry. Washington State University in the form of pGA482 followed by the insertion of a gentamicin resistance gene) to yield LCP2115. The binary plasmid LCP2115, or its derivatives, can be transferred into *Agrobacterium tumefaciens* strains LBA4404 and Mog301, and others using transformation procedures methods known to those skilled in the art. Agrobacterium colonies were selected on kanamycin and gentamicin to obtain bacteria cells that harbor binary plasmids. Binary plasmid DNA was extracted from transformed Agrobacterium and analyzed by restriction endonuclease digestion. The analysis confirmed that binary plasmid DNA has the structure shown in FIGS. 2A–2B. Strain LBA4404 is available from ATCC, 12301 Parklawn Drive, Rockville, Md. Strain Mog 301 was obtained from Mogen International N. V., Einsteinweg 97, 2333 CB, Leiden, Netherlands.

EXAMPLE 10

Transformation of Lettuce with LIYV Coat Protein Gene

Agrobacterium-mediated transfer of the plant expressible LIYV coat protein is done using procedures known to those skilled in the art See, generally, Enomoto et al. (1990). Specifically, cotyledons are aseptically removed from germinated seeds, sliced in half, and soaked in a broth culture of engineered Agrobacterium tumefaciens. Cotyledon pieces are then transferred to Murashige and Skoog (1962) medium (MS) containing 0.1 mg/l 6-benzylaminopurine (BAP), 0.1 mg/l alpha-naphthaleneacetic acid (NAA)(MS-C) and 200 micromolar acetosyringone. Forty-eight hours later, cotyledon pieces are transferred to MS-C medium containing 100 mg/l kanamycin sulfate and 500 mg/l carbenicillin. After two to three weeks shoot buds are harvested and transferred to MS-C medium containing 0.05 mg/l NAA, 0.01 mg/l BAP, 100 mg/I kanamycin sulfate and 500 mg/l carbenicillin. Two to four weeks later elongated shoots are transferred to MS medium containing 100 mg/l kanamycin for root formation. After roots have developed on shoots, transgenic plants (Ro) are removed from agar media and potted into soil. Once the plants are established in soil, they are moved to a greenhouse and grown to sexual maturity. Flowers are self-pollinated to produce R1 transgenic seed. Transfer of this gene into plant cells can also be accomplished using other methods, such as direct DNA uptake (Paszkowski, et al., EMBO J., 1984, 3:2717), microinjection (Crossway, et al., Mol. Gen. Genet. 202:179), electroporation (Fromm et al., Proc. Natl. Acad. Sci. U.S.A. 82:5824), or high-velocity microprojectiles (Klein, et al., Nature 327:70).

DNA was extracted from leaf tissue of mature Ro transgenic plants and used for polymerase chain reaction (PCR) amplification of coat protein and NPTII gene fragments. After PCR amplification the DNA products were analyzed by agarose gel electrophoresis. This analysis revealed that 33 of 37 Ro transgenic lettuce plants tested initially were positive for the LIYV coat protein gene coding sequences. Additionally, 5 of 5 Ro lettuce plants transgenic for an antisense LIYV coat protein gene tested positive for coat protein coding sequences. All Ro transgenic lettuce plants tested positive for NPTII coding sequences by PCR analysis.

Protein in leaf tissue samples taken from Ri transgenic lettuce seedlings was extracted and analyzed for NPTII protein by enzyme-linked immunosorbant assay (ELISA). The procedure and kit supplied by 5 Prime→3 Prime, Inc., Boulder, Colo., was used to assay NPTII expression in R1 transgenic lettuce seedlings. In an initial screen of R1 transgenic seedlings for NPTII protein by ELISA, it was found that 17 of 21 independent transgenic proprietary lettuce lines expressed NPTII. The data indicated that these 17 initial lines are segregating for the NPTII marker gene.

Plant expressible LIYV coat protein also can be transferred to other plants susceptible to LIYV infection such as sugarbeets, cantaloupe, watermelon, other melons, and squash (as well as other cucurbits) using procedures known to those skilled in the art. See, for example, U.S. Pat. No. 4,940,838 to Schilperoot. In addition, see Chee and Slightom (1991) who describe inserting the CMV coat protein gene into cucumbers.

EXAMPLE 11

Expression of LIYV Coat Protein Messenger RNA

Seed harvested from five $R_0$ LIYV CP gene transgenic lettuce regenerants, which had been self-pollinated, was germinated; plants were harvested at about 4 weeks of age. 15 segregants from 5 different transgenic lines were tested for NPTII protein by ELISA. Each of these five lines appeared to be segregating for NPTII protein expression; the lines are 2115–126, 2115–80, 2115–62, 2115–57, and 2115–67. After NPTII ELISA analysis, plants were stored at minus 70° until total RNA was extracted. Total RNA from 6 randomly chosen segregants from each of the 5 families was isolated by the use of Tri Reagent (Molecular Research Center, Inc) and following the instructions provided with the reagent. Subsequently, total RNA was analyzed by Northern blots using the Northern analysis procedure described by Thomas, P. S. (1983) *Methods in Enzymology* 100:255–266; Lehrach et al. (1977) *Biochemistry* 16:4743–4751, and McMaster, G. K., and Carmichael, G. G. (1977).

Following electrophoresis of about 5–10 micrograms total RNA from 6 plants of each of five lines, the RNA was blotted and subsequently hybridized with an LIYV CP coding region DNA probe. A 1.1-kb band was identified by hybridizing with the CP probe (see FIG. 23). The signal obtained with the LIYV CP probe appeared to be present in NPTII-ELISA-positive samples and absent in NPTII-negative samples. LIYV CP Northern hybridization signals appeared to correlate with NPTII ELISA results. This result indicated that the hybridization signals correspond to transgenic coat protein messenger RNA.

FIG. 23 illustrates RNA blot hybridization results obtained with two segregating lines (2115–57 and 2115–67) of LIYV CP transgenic lettuce. Following electrophoresis RNA was electroblotted onto Hybond N (Amersham). The blot was then hybridized with about $30 \times 10^6$ cpm $^{32}$P-labelled LIYV CP coding DNA. NPm ELISA results are indicated as "+" or "−" above each lane. By ethidium-bromide staining of the gel prior to blotting, RNA molecular weight markers were visualized; the position of the hybridizing bands corresponds to 1.1 kb.

TRANSFORMATION OF LETTUCE WITH LIYV HEAT SHOCK PROTEIN

Virion purification and RNA isolation was performed as described in Example 1. Complementary DNA (cDNA) synthesis and cloning was performed as described in Example 2. Plasmid analysis was performed as described in Example 3. Confirmation of the cDNA as a copy of virion RNA was performed as described in Example 4. Nucleotide sequence analysis was performed as described in Example 5.

EXAMPLE 12

Identification of the LIYV HSP70 Gene

Computer analysis identified potential open reading frames in LIYV genomic RNA. To identify the LIYV HSP70 gene, the LIYV cDNA clones are sequenced and assembled into linked groups based on nucleotide sequence content. Open reading frames (ORFs) are identified by computer mapping programs. The identity of the proteins encoded by the various ORFs is accomplished by a FASTA search of UWGCG amino acid sequence data bases. The search reveals that one ORF in the LIYV RNA potentially codes for a HSP70 heat shock protein. Comparison of the LIYV putative HSP70 amino acid sequence with published alignments of heat shock 70 proteins reveals conservation of eight sequence motifs defined by Agranovsky et al. (1991). The presence of the eight conserved motifs in the selected LIYV RNA ORF strongly indicates that this ORF encodes a heat shock 70 protein.

EXAMPLE 13

Construction of a PFLAG clone containing the LIYV HSP70 gene

Figure 5:
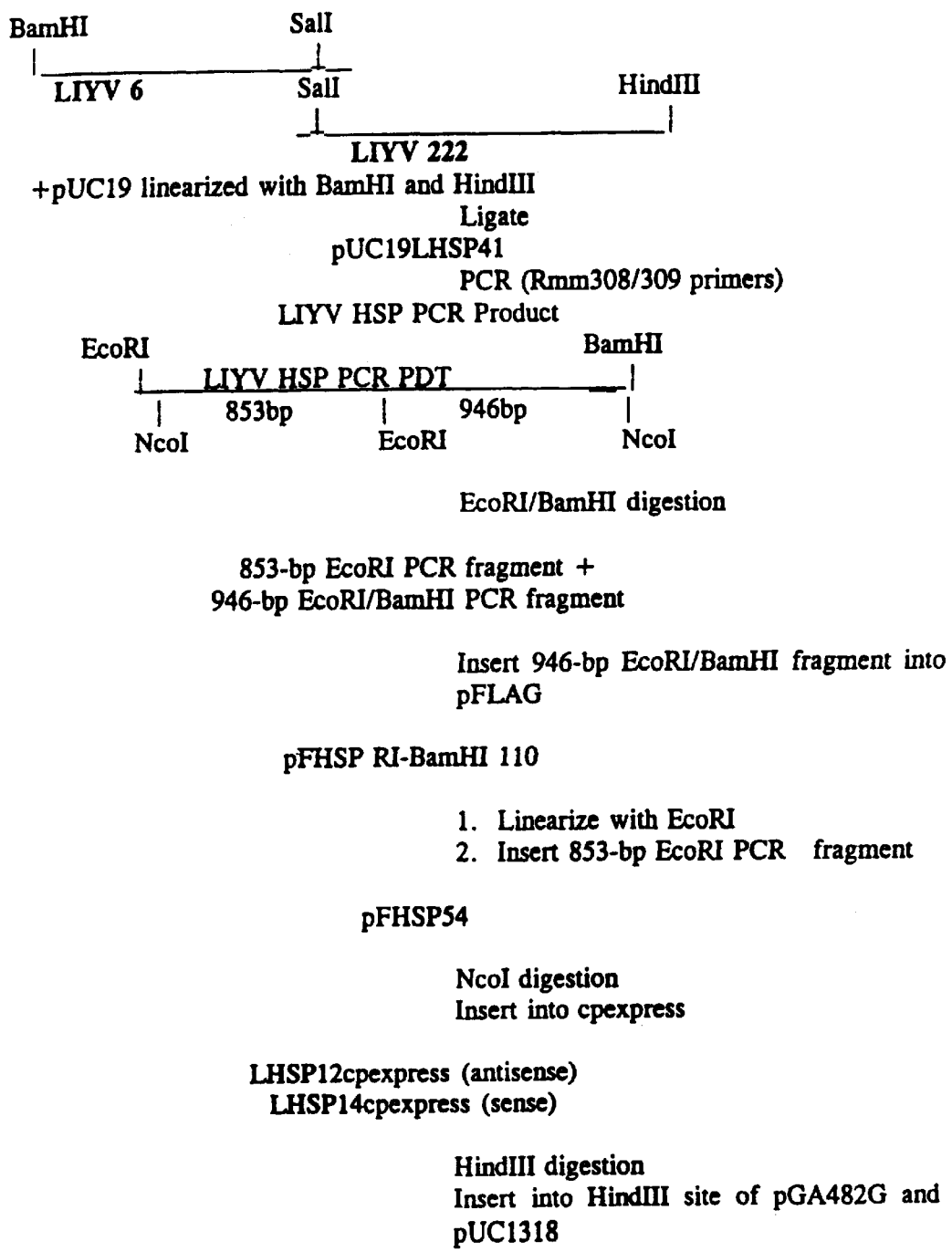
FIG. 5 illustrates a flow chart showing the engineering steps used to reconstruct the complete LIYV heat shock gene from two cDNA clones and to install the complete LIYV heat shock protein-70 gene coding sequence, both in the sense and the antisense orientation, into plant expression vectors and the subsequent insertion plasmids.

A FASTA search of the University of Wisconsin Genetics Computer Group database revealed that the HSP70 open reading frame (ORF1) in the LIYV RNA1 spanned two cDNA clones: LIYV222 and LIYV6 (FIG. 5). The two separate cloned fragments of the LIYV HSP70-cognate gene were ligated to obtain a complete LIYV HSP70 gene [SEQ ID NO: 10]. A SalI-HindIII restriction fragment isolated from LIYV cDNA clone 222 and a SalI-BamHI restriction fragment isolated from LIYV cDNA clone 6 were simultaneously inserted into pUC19 which had been linearized with HindIII and BamHI (FIG. 5). Restriction analysis confirmed that the resulting plasmid, pUC19LHSP41, included the entire LIYV HSP70 cognate ORF. Oligonucleotides RMM 308 (5'GTTTCGAATTCACCATGGGAGATTGTAAGG 3', complementary to the 5' end of the HSP70 ORF and including Eco RI and Nco I sites) [SEQ ID NO:8] and RMM 309 (5'CTGTCTTAACGACATGGTACCTAGGTTTGCG 3', complementary to the 3' end of the HSP70 ORF and including Bam HI and Nco I sites) [SEQ ID NO:9] (FIGS. 5 and 7A–7B) were used to prime a polymerase chain reaction used to install restriction enzyme recognition sites for engineering the LIYV HSP70 coding sequence (FIGS. 7A–7B and 8A–8B) [SEQ ID NO:6] into the bacterial expression plasmid pFLAG (EcoRI and BamHI) and into a plant expression cassette (NcoI) (FIG. 5).

Figure 6A:
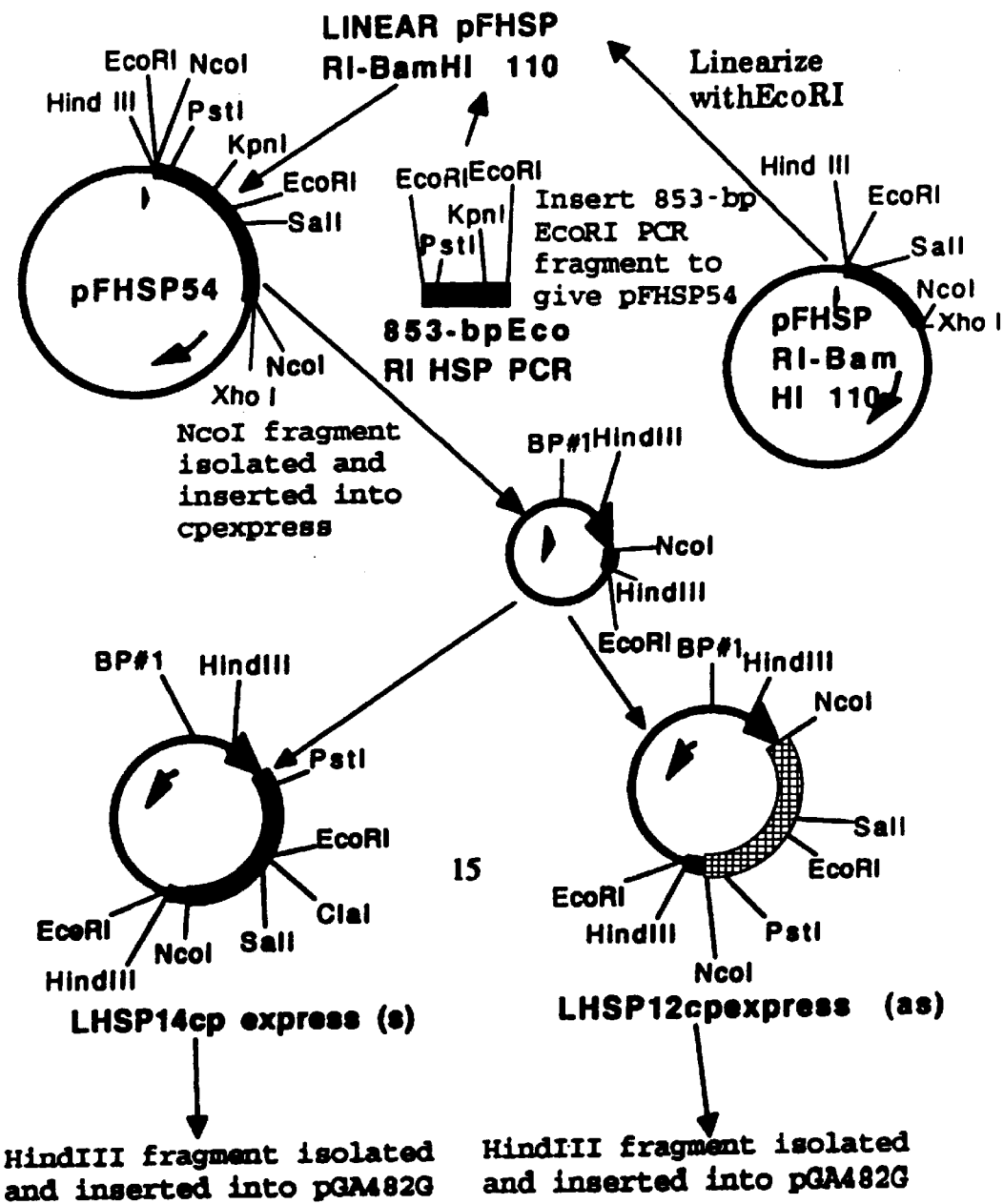

To begin the transfer of the LIYV HSP70 gene into a plant expression cassette, the PCR-amplified LIYV HSP70 gene DNA fragment was digested simultaneously with Eco RI and Bam HI to give appropriate 'sticky ends' for insertion into the plasmid vector pFLAG (FIG. 5). This plasmid is commercially available from Kodak of Rochester, N.Y., and is designed to express cloned genes in *E. coli*. Eco RI/Bam HI digestion of the LIYV HSP70 PCR product DNA resulted in an 853-bp Eco RI fragment and a 946-bp Eco RI/Bam HI fragment. Using standard methods, the 946-bp Eco RI/Bam HI fragment was directionally inserted into pFLAG that also had been digested with Bam HI and Eco RI to give pFHSP RI-BamHI 110 (FIGS. 5 and 6A–6B). Subsequently, the 853-bp Eco RI fragment was directionally inserted into pFLAG that had been digested with Eco RI (FIGS. 5 and 6A–6B). The resulting plasmid is called pFHSP54. LIYV HSP70 gene DNA inserted into pFLAG with these restriction sites codes for a translational fusion protein that includes the OmpA signal peptide and the flag peptide at the amino terminal end. The deduced amino acid sequence of LIYV HSP70 is shown in FIGS. 7A–7B and 9A–9B and in [SEQ ID NO:7].

EXAMPLE 14

Binary Plasmid LIYV HSP70 Gene Expression Cassette Construction

With reference to FIGS. 5 and 6A–6B, the plant expressible HSP70 gene was then moved into a vector suitable for plant expression and Agrobacterium-mediated gene transfer. Following digestion of pFHSP54 with Nco I, the Nco I to Nco I fragment that harbors the LIYV HSP70 gene was excised from pFHSP54 and inserted into the Nco I site of the plasmid vector pUC18cpexpress by the use of standard methods (constructed according to J. L. Slightom, 1991, *Gene*, Vol. 100, p. 251–255, "Custom PCR Engineering of a Plant Expression Vector"). This expression cassette includes about 330 base pairs of the CaMV 35S transcript promoter and 70 bp of the cucumber mosaic virus 5'-untranslated region. The region flanking the 3' end of the inserted gene includes 200 bp of the CaMV35S transcript poly (A) addition signal. The Nco I site maintains the AUG translation initiation site found in the LIYV HSP70 gene. Recombinant pUC18cpexpress plasmids were recovered that include the LIYV HSP70 coding NcoI fragment inserted in both sense (LHSP14cpexpress) and antisense (LHSP12cpexpress) orientations. Sense orientation constructs are designed to give sense mRNA that can be translated into LIYV HSP70 in the plant. The antisense orientation of the NcoI fragment in LHSP12cpexpress is designed to transcribe MRNA in the plant that is complementary to the sense mRNA; no LIYV HSP70 can be translated in the plant from this construct.

The plasmid LHSP12cpexpress harbors the LIYV HSP70 NcoI fragment in an antisense orientation (FIGS. 6A–6B). A HindIII fragment that harbors an LIYV HSP70 as gene expression cassette (LHSP12cpexpress) was excised and inserted into the unique HindIII site of pGA482G (P. Russell, 1993)(available from Gynehung An, Institute of Biological Chemistry, Washington State University in the form of pGA482 followed by the insertion of a gentamicin resistance gene) to yield the plasmid pEPG181 (LHSP54ce1211) (FIGS. 5 and 6A–6B). This binary plasmid was transformed into Agrobacterium and the resulting Agrobacterium strain was used to perform lettuce plant transformation procedures. Plants have been obtained that include the LIYV HSP70 antisense gene construct. We have shown that they express NPTII protein by ELISA and that 15 of 16 tested to date by PCR contain LIYV HSP70 coding sequences.

A Hind III fragment that harbors the LIYV HSP70 gene expression cassette (LHSP14 cpexpress) was excised from LHSP14cpexpress and inserted into the unique Hind III site of the plasmid vector pGA482G to yield pEPG182 (LHSP54ce14101) (FIGS. 2A–2B). The structures shown in FIGS. 2A–2B were verified by restriction analysis. The binary plasmid pEPG182, or its derivatives, can be transferred into *Agrobacterium tumefaciens* strains LBA4404 and Mog301, and others using transformation procedures methods known to those skilled in the art. Agrobacterium colonies were selected on kanamycin and gentamicin to obtain bacteria cells that harbor these binary plasmids. Strain LBA4404 is available from ATCC, 12301 Parklawn Drive, Rockville, Md. Strain Mog 301 was obtained from Mogen International N.V., Einsteinweg 97, 2333 CB, Leiden, Netherlands.

EXAMPLE 15

Transformation of Lettuce with LIYV HSP70 Gene

Agrobacterium-mediated transfer of the plant expressible LIYV HSP70 is done using procedures known to those skilled in the art and as described in Example 10.

DNA was extracted from leaf tissue of mature Ro transgenic plants and used for polymerase chain reaction (PCR) amplification of heat shock protein-70 and NPTII gene fragments. After PCR amplification the DNA products were analyzed by agarose gel electrophoresis. This analysis revealed that 15 of 16 Ro transgenic lettuce plants tested initially were positive for the LIYV heat shock protein-70 gene coding sequences. All Ro transgenic lettuce plants tested positive for NPTII coding sequences by PCR analysis.

Protein in leaf tissue samples taken from R1 transgenic lettuce seedlings was extracted and analyzed for NPTII protein by enzyme4inked immunosorbant assay (ELISA). The procedure and kit supplied by 5 Prime→3 Prime, Inc., Boulder, Colo., was used to assay NPTII expression in R1 transgenic lettuce seedlings. In an initial screen of R1 transgenic seedlings for NPTII protein by ELISA, it was found that all independent transgenic proprietary lettuce lines expressed NPTII. The data indicated that these 16 initial lines are segregating for the NPTII marker gene.

Plant expressible LIYV heat shock protein-70 also can be transferred to other plants susceptible to LIYV infection such as sugarbeets, cantaloupe, watermelon, other melons, and squash (as well as other cucurbits) using procedures known to those skilled in the art. See, for example, U.S. Pat. No. 4,940,838 to Schilperoot. In addition, see Chee and Slightom (1991) who describe inserting the CMV HSP70 gene into cucumbers.

TRANSFORMATION OF LETTUCE WITH LIYV RNA POLYMERASE

Virion purification and RNA isolation was performed as described in Example 1. Complementary DNA (cDNA) synthesis and cloning was performed as described in Example 2. Plasmid analysis was performed as described in Example 3. Confirmation of the cDNA as a copy of virion RNA was performed as described in Example 4. Nucleotide sequence analysis was performed as described in Example 5.

EXAMPLE 16

Identification of the LIYV RNA Polymerase Gene

Computer analysis identified potential open reading frames in LIYV genomic RNA. To identify the LIYV RNA polymerase gene, the LIYV cDNA clones are sequenced and assembled into linked groups based on nucleotide sequence content. Open reading frames (ORFs) are identified by computer mapping programs. The putative identity of the proteins encoded by the various ORFs is accomplished by a FASTA search of UWGCG amino acid sequence data bases. The search reveals that one ORF in the LIYV RNA potentially codes for a RNA polymerase protein. Comparison of LIYV putative RNA polymerase amino acid sequences with published alignments of RNA-dependent RNA polymerases shows that each of the eight conserved motifs is present in the LIYV RNA polymerase-like protein. This analysis strongly suggests that LIYV RNA polymerase is a member of Polymerase Supergroup III described by Koonin (1991). The generally accepted diagnostic motif for RNA-dependent RNA polymerases, the sequence glycine—aspartic acid—aspartic acid (GDD), is highly conserved evolutionarily. This conserved motif (Motif VI in Koonin, 1991) is found in the LIYV putative RNA polymerase.

EXAMPLE 17

Construction of a pFLAG clone containing the LIYV RNA Polymerase gene

A FASTA search of the University of Wisconsin Genetics Computer Group database revealed that the RNA polymerase open reading frame (ORF2) in the LIYV RNA1 is an RNA polymerase-like sequence. Oligonucleotides RMM 301 (5' TATGAGAGCATAGAATTCCCCATGGACATA 3', complementary to the 5' end of the RNA polymerase ORF and including Eco RI and Nco I sites) [SEQ ID NO: 13] and RMM 302 (5' CTGTTAAGGTACCTTMAAGAACTAGTC 3', complementary to the 3' end of the RNA polymerase ORF and including Eco RI and Nco I sites) [SEQ ID NO:14] (FIGS. 10A–10B) were used to prime a polymerase chain reaction used to install restriction enzyme recognition sites for engineering the LIYV RNA polymerase coding sequence (FIGS. 10A–10B and 12A–12B)[SEQ ID NO:1 11] into the bacterial expression plasmid pFLAG (EcoRI) and into a plant expression cassette (NcoI) (FIGS. 11A–11B).

Figure 11A:
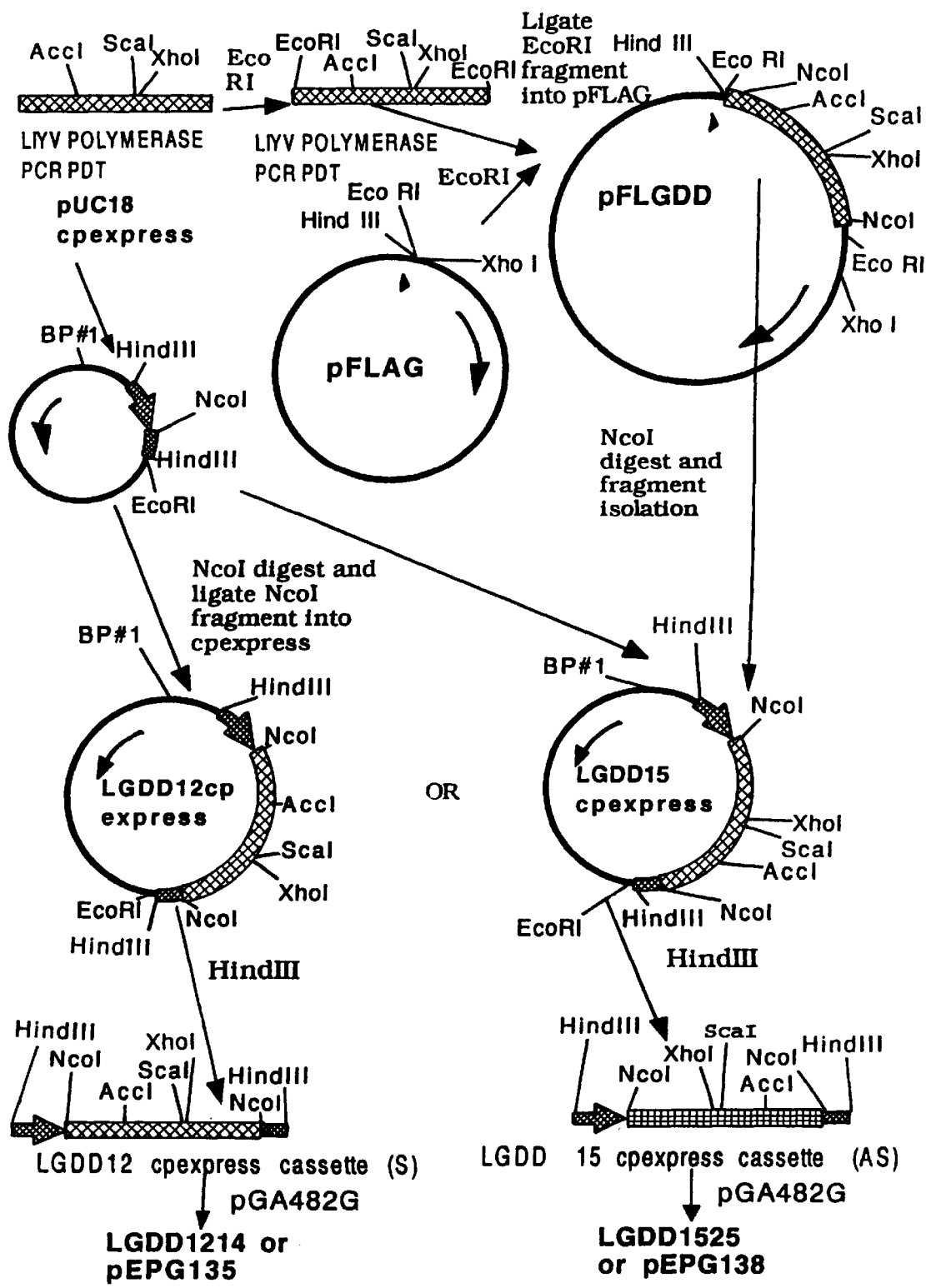
FIGS. 11A–11B illustrate a detailed flow chart showing the engineering steps used to install the complete LIYV RNA polymerase gene coding sequence, both in the sense and the antisense orientation, into plant expression vectors and the genetic maps of the subsequent insertion plasmids used to install the LIYV RNA polymerase gene coding sequences eventually into plants.
Figure 11B:
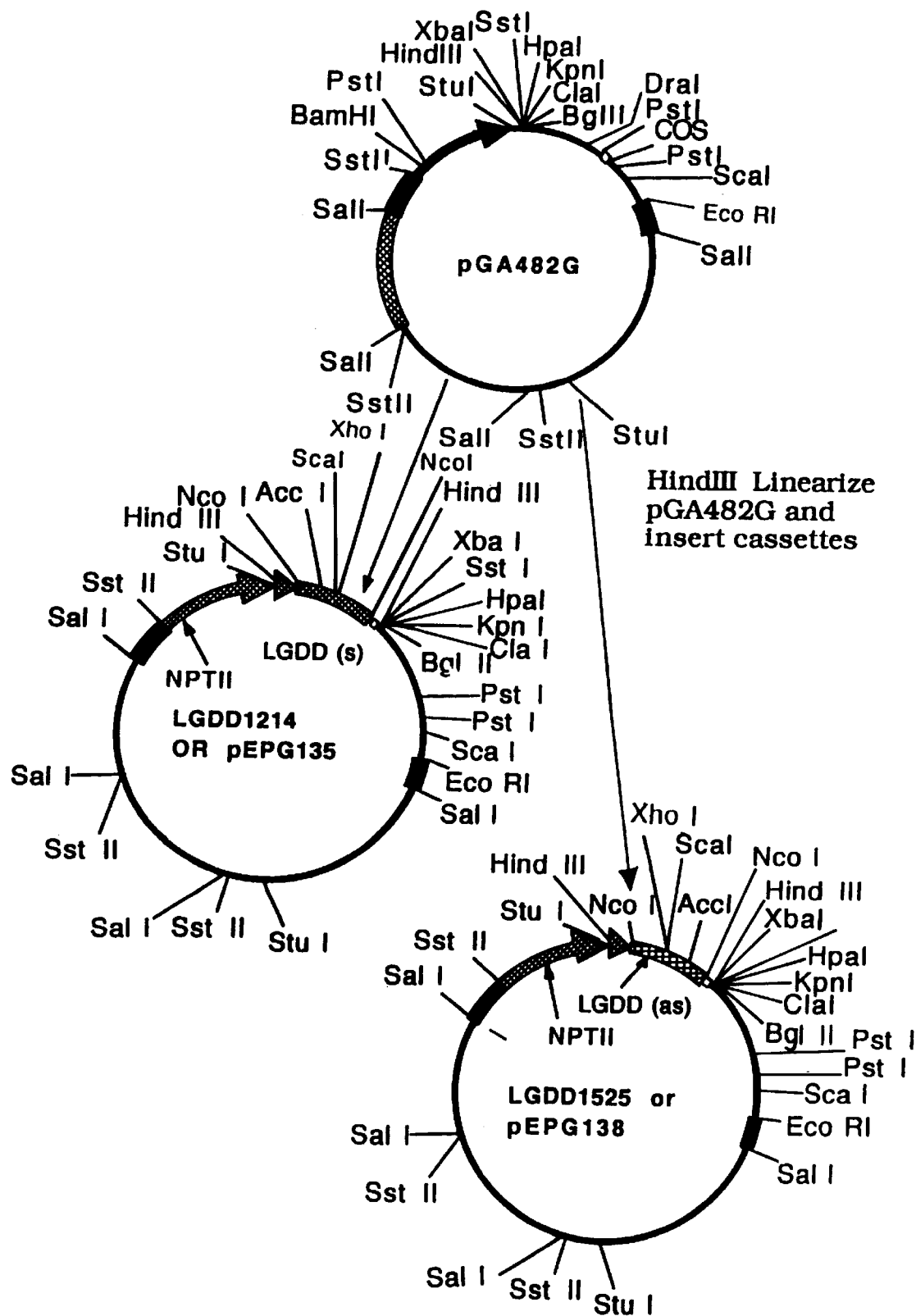
Figure 15A:
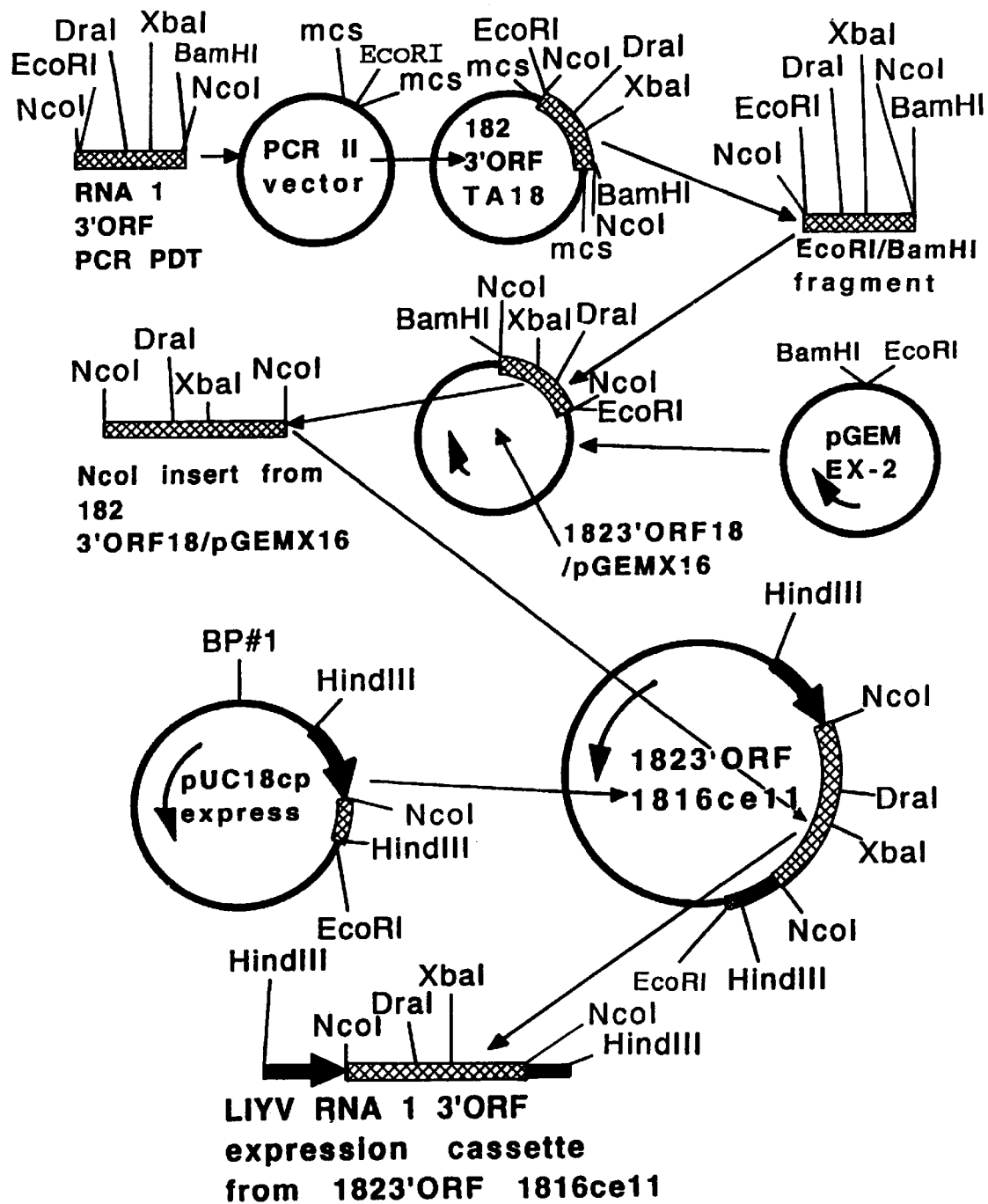
FIGS. 15A–15B illustrate a detailed flow chart showing the engineering steps used to install the complete LIYV RNA1 ORF 3 gene coding sequence, both in the sense and the antisense orientation, into plant expression vectors and the genetic maps of the subsequent insertion plasmids used to install the LIYV RNA1 ORF 3 gene coding sequences eventually into plants.
Figure 15B:
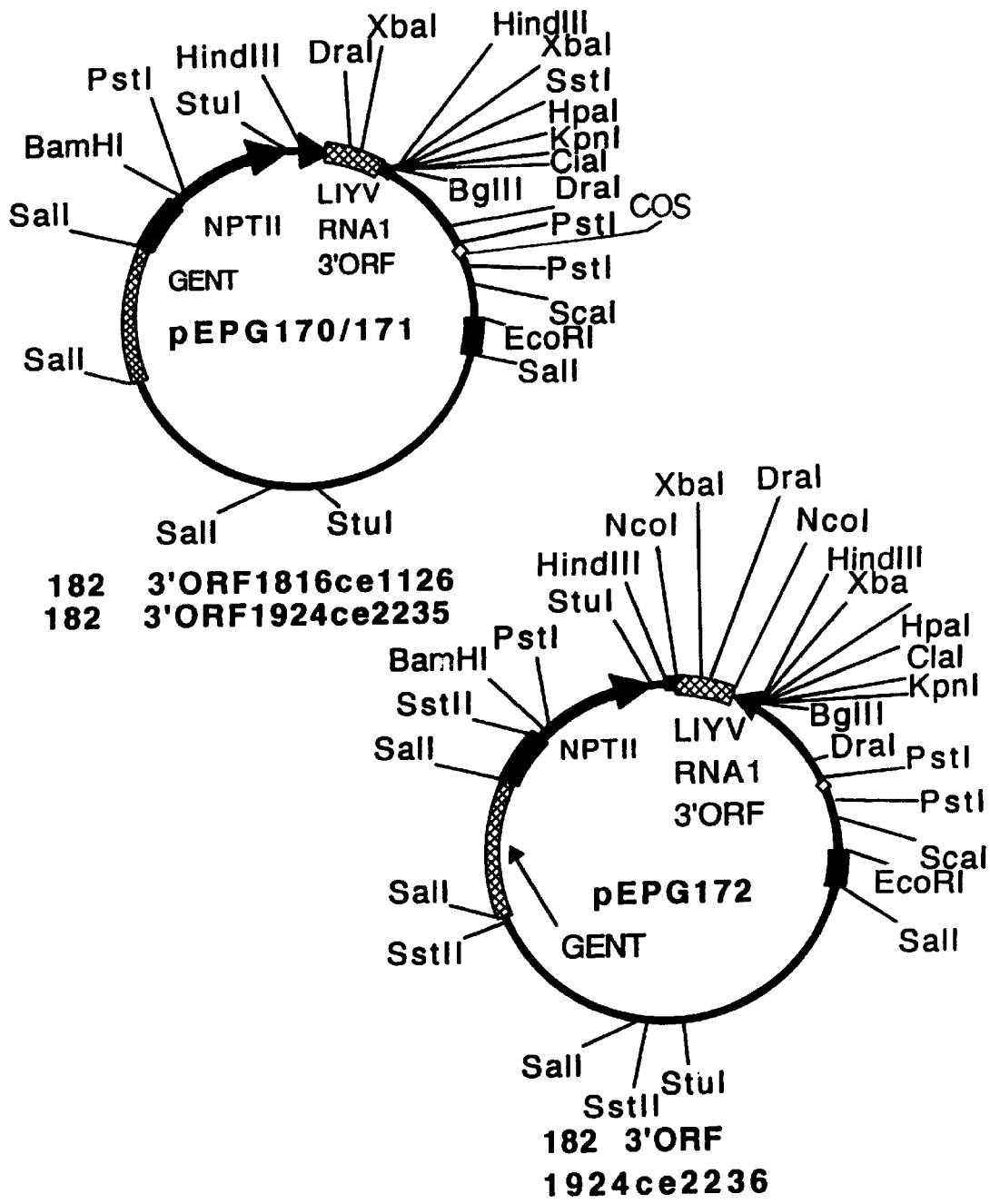
Figure 19A:
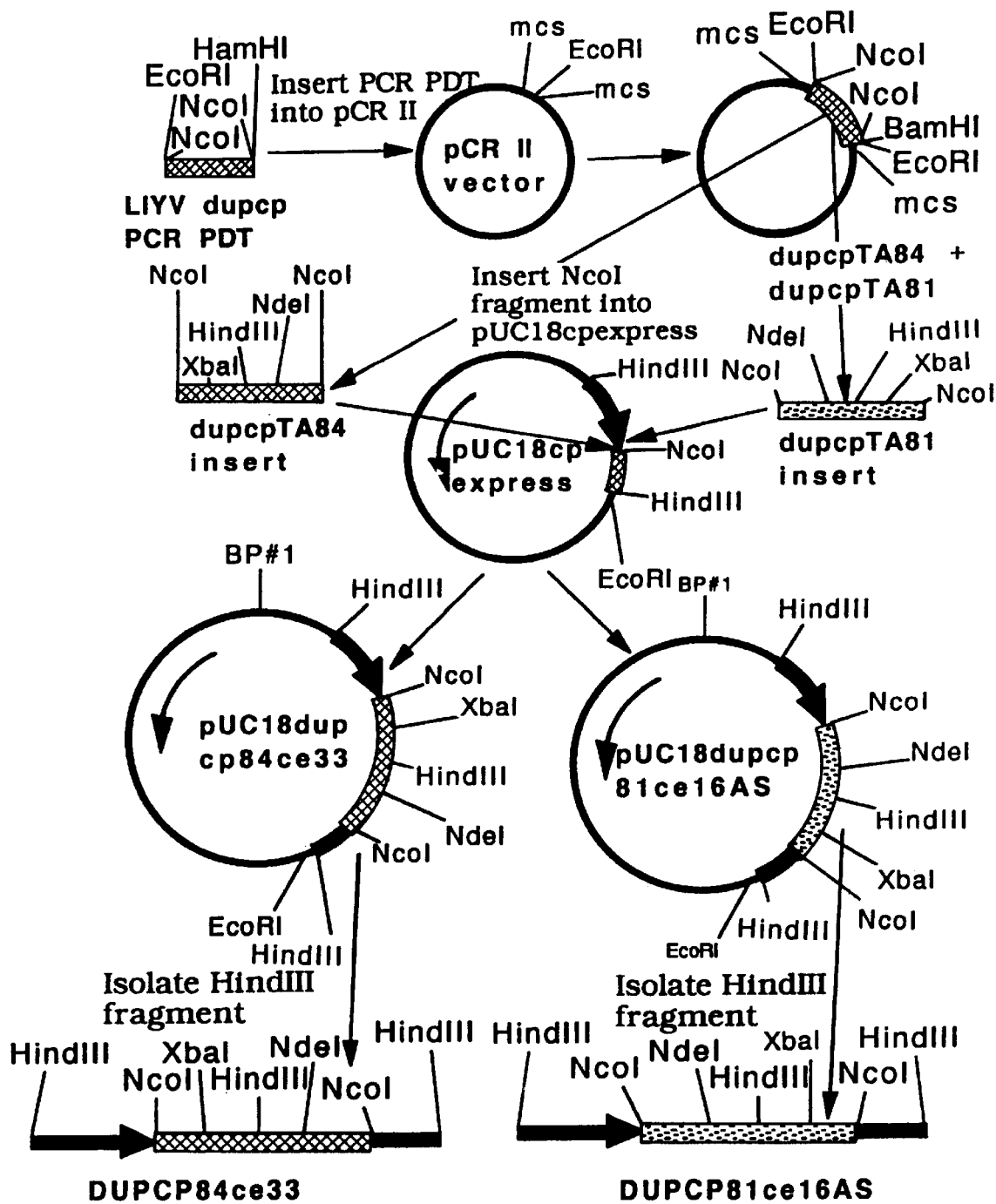
FIGS. 19A–19B illustrate a detailed flow chart showing the engineering steps used to install a portion of the LIYV RNA2 ORF 6 gene coding sequence, both in the sense and the antisense orientation, into plant expression vectors and the genetic maps of the subsequent insertion plasmids used to install the LIYV RNA2 ORF 6 gene coding sequences eventually into plants.
Figure 19B:
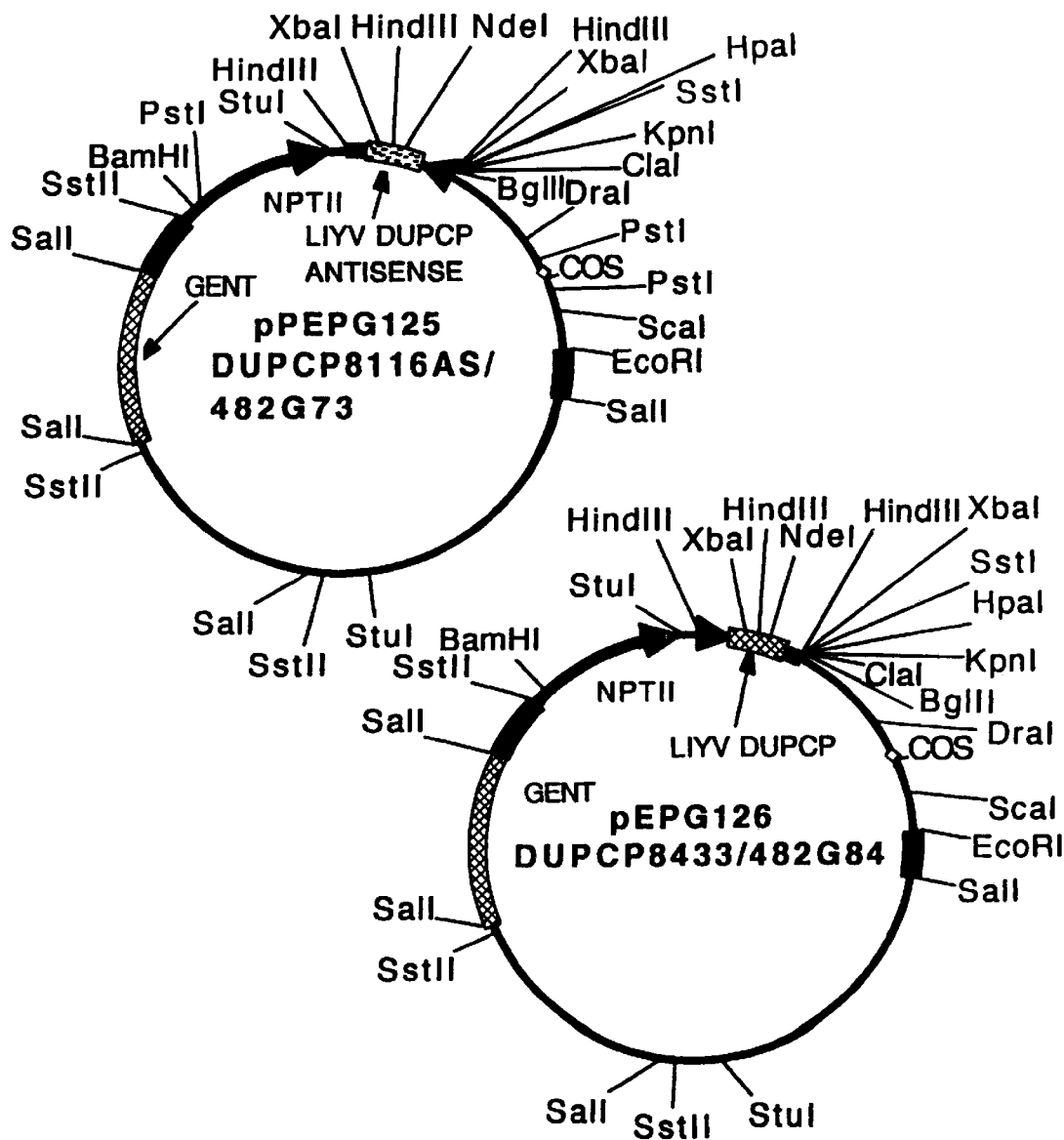

To begin the transfer of the LIYV RNA polymerase gene into a plant expression cassette, the PCR-amplified LIYV RNA polymerase gene DNA fragment was digested with Eco RI to give appropriate 'sticky ends' for insertion into the plasmid vector pFLAG (FIG. 11). This plasmid is commercially available from Kodak of Rochester, New York, and is designed to express cloned genes in *E. coli*. Using standard methods, the LIYV RNA polymerase fragment was directionally inserted into the Eco RI site of pFLAG to produce a plasmid called pFLGDD (FIGS. 11A–11B). LIYV RNA polymerase gene DNA inserted into pFLAG with these restriction sites codes for a translational fusion protein that includes the OmpA signal peptide and the flag peptide at the amino terminal end. The deduced amino acid sequence of LIYV RNA polymerase is shown in FIGS. 10 and 13 and in Sequence I.D. No. 12.

EXAMPLE 18

Binary Plasmid LIYV RNA Polymerase Gene Expression Cassette Construction and Transformation of Lettuce with LIYV RNA Polymerase Gene With reference to FIGS. 11A–11B, the plant expressible RNA polymerase gene was then moved into a vector suitable for plant expression and Agrobacterium-mediated gene transfer. Following digestion of pFLGDD with Nco I, the Nco I to Nco I fragment that harbors the LIYV RNA polymerase gene was excised from pFLGDD and inserted into the Nco I site of the plasmid vector pUC18cpexpress by the use of standard methods (constructed according to J. L. Slightom, 1991, Gene Vol. 100, p. 251–255, "Custom PCR Engineering of a Plant Expression Vector"). This expression cassette includes about 330 base pairs of the CaMV 35S transcript promoter and 70 bp of the cucumber mosaic virus 5'-untranslated region. The region flanking the 3' end of the inserted gene includes 200 bp of the CaMV3SS transcript poly (A) addition signal. The Nco I site maintains the AUG translation initiation site found in the LIYV RNA polymerase gene. Recombinant pUC18cpexpress plasmids were recovered that include the LIYV RNA polymerase coding NcoI fragment inserted in both sense (LGDD12cpexpress) and antisense (LGDD15cpexpress) orientations. Sense orientation constructs are designed to give sense mRNA that can be translated into LIYV RNA polymerase in the plant. The antisense orientation of the NcoI fragment in LGDD15cpexpress is designed to transcribe mRNA in the plant that is complementary to the sense MRNA; no LIYV RNA polymerase can be translated in the plant from this construct.

A. Antisense Construct

A HindIII fragment of LGDD15cpexpress that harbors the LIYV RNA polymerase gene in an antisense orientation was excised and inserted into the unique HindIII site of pGA482G (P. Russell, 1993)(available from Gynehung An, Institute of Biological Chemistry, Washington State University in the form of pGA482 followed by the insertion of a gentamicin resistance gene) to yield the plasmid pEPG138 (LGDD1525) (FIGS. 11A–11B). The structures shown in FIG. 11 were verified by restriction analysis. The binary plasmid pEPG138 was transformed into strains of *Agrobacterium tumefaciens*, for example, strains LBA4404 and Mog301. Strain LBA4404 is available from ATCC, 12301 Parklawn Drive, Rockville, Md. Strain Mog 301 was obtained from Mogen International N. V., Einsteinweg 97, 2333 CB, Leiden, Netherlands. The resulting Agrobacterium strain was used to perform lettuce plant transformation procedures. Agrobacterium-mediated transfer of the plant expressible LIYV RNA polymerase is done using procedures known to those skilled in the art and as described in Example 10.

DNA was extracted from leaf tissue of mature Ro transgenic plants and used for polymerase chain reaction (PCR) amplification of RNA polymerase and NPTII gene fragments. After PCR amplification the DNA products were analyzed by agarose gel electrophoresis. This analysis revealed that 5 of 6 Ro transgenic lettuce plants tested initially were positive for the LIYV RNA polymerase gene coding sequences (pEPG138 or LGDD1525). All Ro transgenic lettuce plants tested positive for NPTII coding sequences by PCR analysis.

Protein in leaf tissue samples taken from Ri transgenic lettuce seedlings was extracted and analyzed for NPTII protein by enzyme-linked immunosorbant assay (ELISA). The procedure and kit supplied by 5 Prime→3 Prime, Inc., Boulder, Colo., was used to assay NPTII expression in R1 transgenic lettuce seedlings. In an initial screen of Ri transgenic seedlings for NPTII protein by ELISA, it was found that all independent transgenic proprietary lettuce lines expressed NPTII. The data indicated that these 10 initial lines are segregating for the NPTII marker gene.

B. Sense Construct

A HindIII fragment of LGDD12cpexpress that harbors the LIYV RNA polymerase gene in a sense orientation was excised and inserted into the unique HindIII site of pGA482G to yield pEPG135(LGDD1214) (FIGS. 11A–11B). The structures shown in FIGS. 11A–11B were verified by restriction analysis. The binary plasmid pBPG135 was transformed into *Agrobacterium tumefaciens* strains LBA4404 and Mog30l. The resulting Agrobacterium strain was used to perform lettuce plant transformation procedures using transformation procedure methods known to those skilled in the art.

DNA was extracted from leaf tissue of mature Ro transgenic plants and used for polymerase chain reaction (PCR) amplification of RNA polymerase and NPTII gene fragments. After PCR amplification the DNA products were analyzed by agarose gel electrophoresis. This analysis revealed that 5 of 6 Ro transgenic lettuce plants tested initially were positive for the LIYV RNA polymerase gene coding sequences (pEPG135 or LGDD1214). All Ro transgenic lettuce plants tested positive for NPTII coding sequences by PCR analysis.

Protein in leaf tissue samples taken from R1 transgenic lettuce seedlings was extracted and analyzed for NPTII protein by enzyme-linked immunosorbant assay (ELISA). The procedure and kit supplied by 5 Prime→3 Prime, Inc., Boulder, Colo., was used to assay NPTII expression in R1 transgenic lettuce seedlings. In an initial screen of R1 transgenic seedlings for NPTII protein by ELISA, it was found that all independent transgenic proprietary lettuce lines expressed NPTII. The data indicated that these 10 initial lines are segregating for the NPTII marker gene.

Plant expressible LIYV RNA polymerase genes also can be transferred to other plants susceptible to LIYV infection such as sugarbeets, cantaloupe, watermelon, other melons, cucumbers and squash (as well as other cucurbits) using procedures known to those skilled in the art. See, for example, U.S. Pat. No. 4,940,838 to Schilperoot.

TRANSFORMATION OF LETTUCE WITH ORF 3 OF LIYV RNA1

Virion purification and RNA isolation was performed as described in Example 1. Complementary DNA (cDNA) synthesis and cloning was performed as described in Example 2. Plasmid analysis was performed as described in Example 3. Confirmation of the cDNA as a copy of virion RNA was performed as described in Example 4. Nucleotide sequence analysis was performed as described in Example 5.

EXAMPLE 19

Identification of the ORF 3 of LIYV RNA1 Gene

Computer analysis identified open reading frames in LIYV genomic RNA. In an attempt to identify the ORFS in LIYV RNA1, LIYV cDNA clones are sequenced and assembled into linked groups based on nucleotide sequence content. Open reading frames (ORFs) are identified by computer mapping programs. The putative identity of the proteins encoded by the various ORFs is accomplished by a FASTA search of UWGCG amino acid sequence data bases. Comparison of the putative amino acid sequence of ORF 3 of LIYV RNA1 with other published amino acid sequences does not reveal a possible identification of the gene.

EXAMPLE 20

Construction of a pGEMX-2 clone containing ORF 3 of LIYV RNA1 gene

Oligonucleotides RMM 398 (5' GATGGAATTCCATGGTAATGATGTCGCCG 3', complementary to the 5' end of ORF 3 of LIYV RNA1 and including Eco RI and Nco I sites [SEQ ID NO: 18]) and RMM 399 (5° CCCACAAAGGTACCACCTAGGGGGG 3', complementary to the 3' end of ORF 3 of LIYV RNA1 and including Bam HI and Nco I sites [SEQ ID NO:19]) (FIG. 14) were used to prime a polymerase chain reaction used to install restriction enzyme recognition sites for engineering the LIYV RNA1 ORF 3 coding sequence (FIGS. 14 and 16)[SEQ ID NO:16] into the bacterial expression plasmid pCR II (Invitrogen Corp., using the manufacturer's suggested protocol)(EcoRI and Bam HI) and into a plant expression cassette (NcoI) (FIGS. 15A–15B). Four clones were chosen for further analysis: these are known as 182 3'ORF TA18 (shown in FIGS. 15A–15B), 182 3'ORF TA19, 182 3'ORF TA20, and 182 3'ORF TA21. Multiple clones were chosen for further analysis because it was expected that each TA clone represented an independent PCR product DNA molecule. If a sequence change was introduced during PCR amplification, it was viewed as unlikely that all four cloned molecules included the same sequence change.

To begin the transfer of the LIYV RNA1 ORF 3 gene into a plant expression cassette, the PCR-amplified 3' ORF LIYV RNA1 gene DNA fragment of clones 182 3'ORF TA18 and 19 were digested with Eco RI and Bam HI to give appropriate 'sticky ends' for insertion into the plasmid vector pGEMX-2 (FIGS. 15A–15B). This plasmid is commercially available from Promega of Madison, Wis., and is designed to express cloned genes in *E. coli*. Using standard methods, the LIYV RNA1 ORF 3 fragment was directionally inserted into the Eco RI/Bam HI sites of pGEMX-2 to produce plasmids called 182 3'ORF19/pGEMX24 and 182 3'ORF18/pGEMX16 (FIGS. 15A–15B). The deduced amino acid sequence of the protein encoded by LIYV RNA1 ORF 3 is shown in FIGS. 14 and 17 and in Sequence I.D. No. 17.

EXAMPLE 21

Gene Expression Cassette, Binary Plasmid Construction and Transformation of Lettuce with LIYV RNA1 ORF 3 Gene With reference to FIGS. 15A–15B, the plant expressible LIYV RNA1 ORF 3 gene was then moved into a vector suitable for plant expression and Agrobacterium-mediated gene transfer. Following digestion of 182 3'ORF19/pGEMX24 and 182 3'ORF19/pGEMX16 with Nco I, the Nco I to Nco I fragment that harbors the LIYV RNA1 ORF 3 gene was excised from each of the clones and inserted into the Nco I site of the plasmid vector pUC18cpexpress by the use of standard methods (constructed according to J. L. Slightom, 1991, Gene, Vol. 100, p. 251–255, "Custom PCR Engineering of a Plant Expression Vector"). This expression cassette includes about 330 base pairs of the CaMV 35S transcript promoter and 70 bp of the cucumber mosaic virus 5'-untranslated region. The region flanking the 3' end of the inserted gene includes 200 bp of the CaMV35S transcript poly (A) addition signal. The Nco I site maintains the AUG translation initiation site found in the ORF 3 LIYV RNA1 gene. The recombinant pUC18cpexpress plasmids (182 3'ORF1816cell (shown in FIGS. 15A–15B) and 182 3'ORF1924ce22) contained the LIYV RNA1 ORF 3 coding NcoI fragment inserted in the sense orientation which give sense mRNA that can be translated into the protein encoded by LIYV RNA1 ORF 3 in the plant. Antisense orientations of the NcoI fragment are also possible.

The plasmids 182 3'ORF1816cell and 182 3'ORF1924ce22 harbors the ORF 3 LIYV RNA1 gene in a sense orientation (FIGS. 15A–15B). A HindIII fragment containing the LRYV RNA1 ORF 3 gene was excised and inserted into the unique HindIII site of the binary plasmid pGA482G (P. Russell, 1993)(available from Gynehung An, Institute of Biological Chemistry, Washington State University in the form of pGA482 followed by the insertion of a gentamicin resistance gene) to yield the plasmid pEPG170 (containing the expression cassette 182 3'ORF1816ce11) and the plasmids pEPG171 and pEPG172 (containing the expression cassette 182 3'ORF1816ce22)(FIGS. 15A–15B). The structures shown in FIG. 15 were verified by restriction analysis. The binary plasmids pEPG170, pEPG171 and pEPG170 were transformed into strains of *Agrobacterium tumefaciens,* for example, strains C58Z707 and Mog301. Strain C58Z707 is available from Angus Hepburn at Indiana University (Hepburn et al., *J. Gen. Micro.* 131:2961–2969 (1985). Strain Mog 301 was obtained from Mogen International N. V., Einsteinweg 97, 2333 CB, Leiden, Netherlands. The resulting Agrobacterium strains were used to perform lettuce plant transformation procedures.

Agrobacterium-mediated transfer of the plant expressible ORF 3 of LIYV RNA1 is done using procedures known to those skilled in the art. For example, Enomoto et al. ((1990) *Plant Cell Reports* 9:6–9) transformed lettuce cotyledon cells and regenerated transformed slants. Specifically, cotyledons are aseptically removed from germinated seeds, sliced in half, and soaked in a broth culture of engineered *Agrobacterium tumefaciens.* Cotyledon pieces are then transferred to Murashige and Skoog ((1962) *Physiol Plantarum* 15:473–497) medium (MS) containing 0.1 mg/l 6-benzylaminopurine (BAP), 0.1 mg/l alpha-naphthaleneacetic acid (NAA)(MS-C) and 200 micromolar acetosyringone. Forty-eight hours later, cotyledon pieces are transferred to MS-C medium containing 100 mg/l kanamycin sulfate and 500 mg/l carbenicillin. After two to three weeks shoot buds are harvested and transferred to MS-C medium containing 0.05 mg/l NAA, 0.01 mg/l BAP, 100 mg/l kanamycin sulfate and 500 mg/l carbenicillin. Two to four weeks later elongated shoots are transferred to MS medium containing 100 mg/l kanamycin for root formation. After roots have developed on shoots, transgenic plants (Ro) are removed from agar media and potted into soil. Once the plants are established in soil, they are moved to a greenhouse and grown to sexual maturity. Flowers are self-pollinated to produce R1 transgenic seed. Transfer of this gene into plant cells can also be accomplished using other methods, such as direct DNA uptake (Paszkowski, et al., *EMBO J.,* 1984, 3:2717), microinjection (Crossway, et al., *Mol. Gen. Genet.* 202:179), electroporation (Fromm et al., *Proc. Natl. Acad. Sci. U.S.A.* 82:5824), or high-velocity microprojectiles (Klein, et al., Nature 327:70).

DNA is extracted from leaf tissue of mature Ro transgenic plants and used for polymerase chain reaction (PCR) amplification of LIYV RNA1 ORF 3 and NPTII gene fragments. After PCR amplification the DNA products are analyzed by agarose gel electrophoresis. This analysis will reveal whether Ro transgenic lettuce plants tested are positive for the LIYV RNA1 ORF 3 gene coding sequences (pEPG138 or LGDD1525). All Ro transgenic lettuce plants test positive for NPTII coding sequences by PCR analysis.

Protein in leaf tissue samples taken from R1 transgenic lettuce seedlings is extracted and analyzed for NPTII protein by enzyme-linked immunosorbant assay (ELISA). The procedure and kit supplied by 5 Prime→3 Prime, Inc., Boulder, Colo., is used to assay NPTII expression in R1 transgenic lettuce seedlings. In an initial screen of R1 transgenic seedlings for NPTII protein by ELISA, it is found that independent transgenic proprietary lettuce lines express NPTII. The data indicates that these initial lines are segregating for the NPTII marker gene.

Plant expressible LIYV RNA1 ORF 3 genes also can be transferred to other plants susceptible to LIYV infection such as sugarbeets, cantaloupe, watermelon, other melons, cucumbers and squash (as well as other cucurbits) using procedures known to those skilled in the art. See, for example, U.S. Pat. No. 4,940,838 to Schilperoot.

TRANSFORMATION OF LETTUCE WITH ORF 6 OF LIYV RNA2

Virion purification and RNA isolation was performed as described in Example 1. Complementary DNA (cDNA) synthesis and cloning was performed as described in Example 2. Plasmid analysis was performed as described in Example 3. Confirmation of the cDNA as a copy of virion RNA was performed as described in Example 4. Nucleotide sequence analysis was performed as described in Example 5.

EXAMPLE 22

Identification of the ORF 6 of LIYV RNA2 Gene

Computer analysis identified potential open reading frames in LIYV genomic RNA. In an attempt to identify ORF 6 of LIYV RNA2, the LIYV cDNA clones are sequenced and assembled into linked groups based on nucleotide sequence content. Open reading frames (ORFs) are identified by computer mapping programs. The putative identity of the proteins encoded by the various ORFs is accomplished by a FASTA search of UWGCG amino acid sequence data bases. Comparison of the putative amino acid sequence of the ORF 6 of LIYV RNA2 with other published amino acid sequences does not reveal an identification of the gene.

EXAMPLE 23

Construction of a pCRII clone containing the LIYV RNA2 ORF 6 gene

Oligonucleotides RMM415 (5'CGGAATTCCATGGTCAAAACGAG 3', complementary to the 5' end of the ORF 6 of LIYV RNA2 and including Eco RI and Nco I sites) [SEQ ID NO:23] and RMM416 (5'CGGGCTGTATTCGTTTGGTACCC TCTTGTC-CCTAGGTATCT 3', complementary to the 3' end of ORF 6 of LIYV RNA2 and including Bam HI and Nco I sites) [SEQ ID NO:24] (FIG. 18) were used to prime a polymerase chain reaction used to install restriction enzyme recognition sites for engineering a portion of ORF 6 LIYV RNA2 coding sequence (FIG. 18)[SEQ ID NO:25] into the plasmid pCR II (Invitrogen Corp., using the manufacturer's protocol)(EcoRI and Bam HI) and into a plant expression cassette (NcoI) (FIGS. 19A–19B). Three clones were chosen for further analysis: these are known as ORF6TA81, ORF6TA83 and ORF6TA84. Clones TA84 and TA81 are shown in FIGS. 19A–19B. The entire nucleotide sequence of LIYV RNA2 ORF 6 is shown in FIG. 20 and in Sequence I.D. No. 21. The deduced amino acid sequence of LIYV RNA2 ORF 6 is shown in FIGS. 21A–21B and in Sequence I.D. No. 22.

EXAMPLE 24

Gene Expression Cassette, Binary Plasmid Construction and Transformation of Lettuce with ORF 6 LIYV RNA2 Gene To transfer ORF 6 of LIYV RNA2 into a plant expression cassette, an NcoI fragment was excised from dupcpTA84 or dupcpTA81 and inserted into pUC18cpexpress. The recombinant pUC18cpexpress plasmids (pUC18dupcp84ce33 and pUC18dupcp81ce16AS) contained the ORF 6 LIYV RNA2 coding NcoI fragment isolated from dupcpTA84 inserted in the sense and the antisense orientation which give sense MRNA that can be translated into protein. Antisense orientations of the NcoI fragment are also possible.

With reference to FIGS. 19A–19B, the plant expressible ORF 6 LIYV RNA gene was then moved into a vector suitable for plant expression and Agrobacterium-mediated gene transfer. Following digestion of ORF6TA84 with Nco I, the Nco I to Nco I fragment that harbors the ORF 6 LIYV RNA2 gene was excised from the dupcpTA84 clone and inserted into the Nco I site of the plasmid vector pUC18cpexpress by the use of standard methods (constructed according to J. L. Slightom, 1991, Gene, Vol. 100, p. 251–255, "Custom PCR Engineering of a Plant Expression Vector"). This expression cassette includes about 330 base pairs of the CaMV 35S transcript promoter and 70 bp of the cucumber mosaic virus 5'-untranslated region. The region flanking the 3' end of the inserted gene includes 200 bp of the CaMV35S transcript poly (A) addition signal. The Nco I site maintains the AUG translation initiation site found in the ORF 6 LIYV RNA2 gene. Recombinant pUC18cpexpress plasmids were recovered that include the ORF 6 LIYV RNA2 coding NcoI fragment inserted in both sense (pUC18dupcp84ce33) and antisense (pUC18dupcp81ce16AS) orientations (FIGS. 19A–19B). Sense orientation constructs are designed to give sense mRNA that can be translated into the protein encoded by ORF 6 LIYV RNA2 in the plant. The antisense orientation of the NcoI fragment in pUC18dupcp81ce16AS is designed to transcribe mRNA in the plant that is complementary to the sense mRNA.

A HindIII fragment of pUC18dupcp84ce33 that harbors the ORF 6 LIYV RNA2 gene in a sense orientation was excised and inserted into the unique HindIII site of pGA482G to yield pEPG126 (FIGS. 19A–19B). The structures shown in FIGS. 19A–19B were verified by restriction analysis. The binary plasmid pEPG126 was transformed into *Agrobacterium tumefaciens* strains LBA4404 and Mog301. The resulting Agrobacterium strain was used to perform lettuce plant transformation procedures using transformation procedure methods known to those skilled in the art.

A HindIII fragment of pUC18dupcp81cel6AS that harbors the ORF 6 LIYV RNA2 gene in an antisense orientation was excised and inserted into the unique HindIII site of pGA482G (P. Russell, 1993)(available from Gynehung An, Institute of Biological Chemistry, Washington State University in the form of pGA482 followed by the insertion of a gentamicin resistance gene) to yield the plasmid pEPG125 (FIGS. 19A–19B). The structures shown in FIG. 19 were verified by restriction analysis. The binary plasmid pEPG125 was transformed into strains of *Agrobacterium tumefaciens,* for example, strains LBA4404 and Mog301. Strain LBA4404 is available from ATCC, 12301 Parklawn Drive, Rockville, Md.. Strain Mog 301 was obtained from Mogen International N. V., Einsteinweg 97, 2333 CB, Leiden, Netherlands. The resulting Agrobacterium strain was used to perform lettuce plant transformation procedures.

Agrobacterium-mediated transfer of the plant expressible ORF 6 LIYV RNA2 is done using procedures known to those skilled in the art. For example, Enomoto et al. ((1990) *Plant Cell Reports* 9:6–9) transformed lettuce cotyledon cells and regenerated transformed slants. Specifically, cotyledons are aseptically removed from germinated seeds, sliced in half, and soaked in a broth culture of engineered *Agrobacterium tumefaciens.* Cotyledon pieces are then transferred to Murashige and Skoog ((1962) *Physiol Plantarum* 15:473497) medium (MS) containing 0.1 mg/l 6-benzylaminopurine (BAP), 0.1 mg/l alpha-naphthaleneacetic acid (NAA)(MS-C) and 200 micromolar acetosyringone. Forty-eight hours later, cotyledon pieces are transferred to MS-C medium containing 100 mg/l kanamycin sulfate and 500 mg/l carbenicillin. After two to three weeks shoot buds are harvested and transferred to MS-C medium containing 0.05 mg/l NAA, 0.01 mg/l BAP, 100 mg/l kanamycin sulfate and 500 mg/l carbenicillin. Two to four weeks later elongated shoots are transferred to MS medium containing 100 mg/l kanamycin for root formation. After roots have developed on shoots, transgenic plants (Ro) are removed from agar media and potted into soil. Once the plants are established in soil, they are moved to a greenhouse and grown to sexual maturity. Flowers are self-pollinated to produce R1 transgenic seed. Transfer of this gene into plant cells can also be accomplished using other methods, such as direct DNA uptake (Paszkowski, et al., *EMBO J.,* 1984, 3:2717), microinjection (Crossway, et al., *Mol. Gen. Genet.* 202:179), electroporation (Fromm et al., *Proc. Natl. Acad. Sci. U.S.A.* 82:5824), or high-velocity microprojectiles (Klein, et al., Nature 327:70).

DNA is extracted from leaf tissue of mature Ro transgenic plants and used for polymerase chain reaction (PCR) amplification of ORF 6 LIYV RNA2 and NPTII gene fragments. After PCR amplification the DNA products are analyzed by agarose gel electrophoresis. This analysis will reveal whether the Ro transgenic lettuce plants tested are positive for the ORF 6 LIYV RNA2 gene coding sequences (pEPG125 or pEPG126). All Ro transgenic lettuce plants test positive for NPTII coding sequences by PCR analysis.

Protein in leaf tissue samples taken from R1 transgenic lettuce seedlings is extracted and analyzed for NPTII protein by enzyme-linked immunosorbant assay (ELISA). The procedure and kit supplied by 5 Prime→3 Prime, Inc., Boulder, Colo., is used to assay NPTII expression in R1 transgenic lettuce seedlings. In an initial screen of R1 transgenic seedlings for NPTII protein by ELISA, it is found that independent transgenic proprietary lettuce lines express NPTII. The data indicated that these initial lines are segregating for the NPTII marker gene.

Plant expressible ORF 6 LIYV RNA2 genes also can be transferred to other plants susceptible to LIYV infection such as sugarbeets, cantaloupe, watermelon, other melons, cucumbers and squash (as well as other cucurbits) using procedures known to those skilled in the art. See, for example, U.S. Pat. No. 4,940,838 to Schilperoot.

While specific embodiments of the invention have been described, it should be apparent to those skilled in the art that various modifications thereof can be made without departing from the true spirit and scope of the invention. Accordingly, it is intended that the following claims cover all such modifications within the full inventive concept.

We claim:

1. An isolated nucleic acid comprising a portion of the lettuce infectious yellows virus (LIYV) genome which encodes an LIYV protein, wherein said nucleic acid comprises a nucleotide sequence selected from the group consisting of:
the nucleotide sequence as shown in SEQ ID NO:1;
a nucleotide sequence which encodes the same sequence of amino acids as encoded by the nucleotide sequence shown in SEQ ID NO: 1;
the nucleotide sequence as shown in SEQ ID NO:6;
a nucleotide sequence which encodes the same sequence of amino acids as encoded by the nucleotide sequence shown in SEQ ID NO:6;
the nucleotide sequence as shown in SEQ ID NO:11;
a nucleotide sequence which encodes the same sequence of amino acids as encoded by the nucleotide sequence shown in SEQ ID NO:11;
the nucleotide sequence as shown in SEQ ID NO:16;
a nucleotide sequence which encodes the same sequence of amino acids as encoded by the nucleotide sequence shown in SEQ ID NO:16;
the nucleotide sequence as shown in SEQ ID NO:21; and
a nucleotide sequence which encodes the same sequence of amino acids as encoded by the nucleotide sequence shown in SEQ ID NO:21.

2. An isolated nucleic acid according to claim 1 wherein said nucleic acid comprises a nucleotide sequence selected from the group consisting of:
the nucleotide sequence as shown in SEQ ID NO:1; and
a nucleotide sequence which encodes the same sequence of amino acids as encoded by the nucleotide sequence shown in SEQ ID NO:1.

3. An isolated nucleic acid according to claim 1 wherein said nucleic acid comprises a nucleotide sequence selected from the group consisting of:
the nucleotide sequence as shown in SEQ ID NO:6; and
a nucleotide sequence which encodes the same sequence of amino acids as encoded by the nucleotide sequence shown in SEQ ID NO:6.

4. An isolated nucleic acid according to claim 1 wherein said nucleic acid comprises a nucleotide sequence selected from the group consisting of:
the nucleotide sequence as shown in SEQ ID NO:11; and
a nucleotide sequence which encodes the same sequence of amino acids as encoded by the nucleotide sequence shown in SEQ ID NO:11.

5. An isolated nucleic acid according to claim 1 wherein said nucleic acid comprises a nucleotide sequence selected from the group consisting of:
the nucleotide sequence as shown in SEQ ID NO:16; and
a nucleotide sequence which encodes the same sequence of amino acids as encoded by the nucleotide sequence shown in SEQ ID NO:16.

6. An isolated nucleic acid according to claim 1 wherein said nucleic acid comprises a nucleotide sequence selected from the group consisting of:

the nucleotide sequence as shown in SEQ ID NO:21; and a nucleotide sequence which encodes the same sequence of amino acids as encoded by the nucleotide sequence shown in SEQ ID NO:21.

7. A plant transformation vector comprising a nucleotide sequence as recited in claim 1, a promoter, and a polyadenylation signal, wherein said promoter is upstream and operably linked to said nucleotide sequence, and said nucleotide sequence is upstream and operably linked to said polyadenylation signal.

8. A plant transformation vector according to claim 7 wherein said promoter is Cauliflower mosaic virus CaMV 35S promoter.

9. A plant transformation vector according to claim 8 wherein said polyadenylation signal is the polyadenylation signal of the cauliflower mosaic CaMV 35S gene.

10. A bacterial cell comprising the plant transformation vector of claim 9.

11. A bacterial cell of claim 10 in which said bacterial cell is an *Agrobacterium tumefaciens* cell.

12. A transformed plant cell comprising the plant transformation vector of claim 7.

13. A transformed plant cell of claim 12 further including the 35S promoter of cauliflower mosaic virus and the polyadenylation signal of the cauliflower mosaic 35S gene.

14. A transgenic plant selected from the family *Latuca sativa L.* comprising transformed cells of claim 13.

15. A transgenic plant selected from the family *Cucurbita pepo L.* comprising transformed cells of claim 13.

16. A transgenic plant selected from the family *Cucumis melo L.* comprising transformed cells of claim 13.

17. A transgenic plant selected from the family *Citrullus vulgaris L.* comprising transformed cells of claim 13.

18. A transformed plant seed comprising the plant transformation vector of claim 7.

19. A transformed plant seed of claim 18 further including the 35S promoter of cauliflower mosaic virus and the polyadenylation signal of the cauliflower mosaic 35S gene.

20. A transgenic plant selected from the family *Latuca sativa L.* comprising transformed cells of claim 19.

21. A transgenic plant selected from the family *Cucurbita pepo L.* comprising transformed cells of claim 19.

22. A transgenic plant selected from the family *Cucumis melo L.* comprising transformed cells of claim 19.

23. A transgenic plant selected from the family *Citrullus vulgaris L.* comprising transformed cells of claim 19.

24. An isolated nucleic acid comprising a portion of the lettuce infectious yellows virus (LIYV) genome which encodes an LIYV protein, wherein said nucleic acid comprises an antisense nucleotide sequence complementary to a nucleotide sequence selected from the group consisting of:

the nucleotide sequence as shown in SEQ ID NO:1;

a nucleotide sequence which encodes the same sequence of amino acids as encoded by the nucleotide sequence shown in SEQ ID NO:1;

the nucleotide sequence as shown in SEQ ID NO:6;

a nucleotide sequence which encodes the same sequence of amino acids as encoded by the nucleotide sequence shown in SEQ ID NO:6;

the nucleotide sequence as shown in SEQ ID NO:11;

a nucleotide sequence which encodes the same sequence of amino acids as encoded by the nucleotide sequence shown in SEQ ID NO:11;

the nucleotide sequence as shown in SEQ ID NO:16;

a nucleotide sequence which encodes the same sequence of amino acids as encoded by the nucleotide sequence shown in SEQ ID NO: 16;

the nucleotide sequence as shown in SEQ ID NO:21; and a nucleotide sequence which encodes the same sequence of amino acids as encoded by the nucleotide sequence shown in SEQ ID NO:21.

25. An isolated nucleic acid according to claim 24 wherein said nucleotide sequence is selected from the group consisting of:

the nucleotide sequence as shown in SEQ ID NO:1; and a nucleotide sequence which encodes the same sequence of amino acids as encoded by the nucleotide sequence shown in SEQ ID NO:1.

26. An isolated nucleic acid according to claim 24 wherein said nucleotide sequence is selected from the group consisting of:

the nucleotide sequence as shown in SEQ ID NO:6; and a nucleotide sequence which encodes the same sequence of amino acids as encoded by the nucleotide sequence shown in SEQ ID NO:6.

27. An isolated nucleic acid according to claim 24 wherein said nucleotide sequence is selected from the group consisting of:

the nucleotide sequence as shown in SEQ ID NO:11; and a nucleotide sequence which encodes the same sequence of amino acids as encoded by the nucleotide sequence shown in SEQ ID NO:11.

28. An isolated nucleic acid according to claim 24 wherein said nucleotide sequence is selected from the group consisting of:

the nucleotide sequence as shown in SEQ ID NO:16; and a nucleotide sequence which encodes the same sequence of amino acids as encoded by the nucleotide sequence shown in SEQ ID NO:16.

29. An isolated nucleic acid according to claim 24 wherein said nucleotide sequence is selected from the group consisting of:

the nucleotide sequence as shown in SEQ ID NO:21; and a nucleotide sequence which encodes the same sequence of amino acids as encoded by the nucleotide sequence shown in SEQ ID NO:21.

30. A plant transformation vector comprising an antisense nucleotide sequence as recited in claim 24 a promoter, and a polyadenylation signal, wherein said promoter is upstream and operably linked to said antisense nucleotide sequence, and said antisense nucleotide sequence is upstream and operably linked to said polyadenylation signal.

31. A plant transformation vector according to claim 30 wherein said promoter is Cauliflower mosaic virus CaMV 35S promoter.

32. A plant transformation vector according to claim 31 wherein said polyadenylation signal is the polyadenylation signal of the cauliflower mosaic CaMV 35S gene.

33. A bacterial cell comprising the plant transformation vector of claim 32.

34. A bacterial cell of claim 33 in which said bacterial cell is an *Agrobacterium tumefaciens* cell.

35. A transformed plant cell comprising the plant transformation vector of claim 30.

36. A transformed plant cell of claim 35 further including the 35S promoter of cauliflower mosaic virus and the polyadenylation signal of the cauliflower mosaic 35S gene.

37. A transgenic plant selected from the family *Latuca sativa L.* comprising transformed cells of claim 36.

38. A transgenic plant selected from the family *Cucurbita pepo L.* comprising transformed cells of claim 36.

39. A transgenic plant selected from the family *Cucumis melo L.* comprising transformed cells of claim 36.

40. A transgenic plant selected from the family *Citrullus vulgaris L.* comprising transformed cells of claim 36.

41. A transformed plant seed comprising the plant transformation vector of claim 30.

42. A transformed plant seed of claim 41 further including the 35S promoter of cauliflower mosaic virus and the polyadenylation signal of the cauliflower mosaic 35S gene.

43. A transgenic plant selected from the family *Latuca sativa L.* comprising transformed cells of claim 42.

44. A transgenic plant selected from the family *Cucurbita pepo L.* comprising transformed cells of claim 42.

45. A transgenic plant selected from the family *Cucumis melo L.* comprising transformed cells of claim 42.

46. A transgenic plant selected from the family *Citrullus vulgaris L.* comprising transformed cells of claim 42.

* * * * *